US011865083B2

(12) United States Patent
Ooi et al.

(10) Patent No.: US 11,865,083 B2
(45) Date of Patent: Jan. 9, 2024

(54) RAPID METHOD OF GENERATING LIVE ATTENUATED VACCINES

(71) Applicant: NATIONAL UNIVERSITY OF SINGAPORE, Singapore (SG)

(72) Inventors: Eng Eong Ooi, Singapore (SG); Kenneth Goh, Singapore (SG); Swee Sen Kwek, Singapore (SG); Choon Kit Tang, Singapore (SG)

(73) Assignee: NATIONAL UNIVERSITY OF SINGAPORE, Singapore (SG)

(*) Notice: Subject to any disclaimer, the term of this patent is extended or adjusted under 35 U.S.C. 154(b) by 288 days.

(21) Appl. No.: 17/249,329

(22) Filed: Feb. 26, 2021

(65) Prior Publication Data

US 2021/0187094 A1 Jun. 24, 2021

Related U.S. Application Data

(63) Continuation of application No. 16/093,262, filed as application No. PCT/SG2017/050211 on Apr. 13, 2017, now abandoned.

(30) Foreign Application Priority Data

Apr. 14, 2016 (SG) .......................... 10201602980W

(51) Int. Cl.
*A61K 39/12* (2006.01)
*A61K 39/00* (2006.01)

(52) U.S. Cl.
CPC ...... *A61K 39/12* (2013.01); *A61K 2039/5254* (2013.01); *C12N 2770/24121* (2013.01); *C12N 2770/24122* (2013.01); *C12N 2770/24134* (2013.01); *C12N 2770/24164* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 2002/0090608 A1 | 7/2002 | Palese et al. | |
| 2004/0002056 A1 | 1/2004 | Lorens et al. | |
| 2005/0010043 A1 | 1/2005 | Whitehead et al. | |
| 2016/0106828 A1 | 4/2016 | Toro | |
| 2019/0125855 A1 | 5/2019 | Ooi et al. | |
| 2021/0187094 A1* | 6/2021 | Ooi | A61K 39/12 |

FOREIGN PATENT DOCUMENTS

| | | |
|---|---|---|
| WO | 0104272 | 1/2001 |

OTHER PUBLICATIONS

Sequence alignments of instant SEQ ID No. 39 with GenEmbl database accession No. KJ776791 (Apr. 2014).*
Sequence alignments of instant SEQ ID No. 40 with GenEmbl database accession No. KJ776791 (Apr. 2014).*
Sequence alignments of instant SEQ ID No. 41 with GenEmbl database accession No. KJ776791 (Apr. 2014).*
Sequence alignments of instant SEQ ID No. 42 with GenEmbl database accession No. KJ776791 (Apr. 2014).*
Sequence alignments of SEQ ID No. 39 with GenEmbl database access No. MG827392 (Jan. 2018).*
Sequence alignments of SEQ ID No. 40 with GenEmbl database access No. MG827392 (Jan. 2018).*
Sequence alignments of SEQ ID No. 41 with GenEmbl database access No. MG827392 (Jan. 2018).*
Sequence alignments of SEQ ID No. 42 with GenEmbl database access No. MG827392 (Jan. 2018).*
Zwek et al. (Nature Communications. 23018; 9:1031: 1-13).*
Haddow et al. (PLoS Neglected Tropical Diseases. 2012; 6 (2): e1477).*
Borucki et al. (PLoS One. Dec. 2019; 14 (12): e0225699).*
Faye et al. (PLoS Neglected Tropical Diseases. 2014; 8(1): e2636).*
Yau et al. (EBioMedicine. 2020; 61: 103028).*
Kim et al. (Vaccines. 2022; 10: 1517).*
Pattnaik et al. (Vaccines. 2020; 8 (2): 266).*
European Application No. EP17782757.3, Office Action dated Oct. 8, 2021, 6 pages.
"Zika Virus Strain PF13/251013-18, Complete Genome", GenBank Accession No. KX369547, Jul. 5, 2016, 4 pages.
U.S. Appl. No. 16/093,262 , Non-Final Office Action, dated Nov. 3, 2020, 14 pages.
Arunachalam et al., "Phylogenetic Analysis of Pandemic Influenza A/H1N1 Virus", Biologia, vol. 67, Issue 1, 2012, pp. 14-31.
Azizi et al., "Influence of Human Papillomavirus Type 16 (HPV-16) E2 Polymorphism on Quantification of HPV-16 Episomal and Integrated DNA in Cervicovaginal Lavages from Women with Cervical Intraepithelial Neoplasia", Journal of General Virology, vol. 89, 2008, pp. 1716-1728.
Balas et al., "Different Innate Signatures Induced in Human Monocyte-derived Dendritic Cells by Wild-Type Dengue 3 Virus, Attenuated but Reactogenic Dengue 3 Vaccine Virus, or Attenuated Nonreactogenic Dengue 1-4 Vaccine Virus Strains", The Journal of Infectious Diseases, vol. 203, No. 1, Jan. 1, 2011, pp. 103-108.
Blaney Jr. et al., "Genetic Basis of Attenuation of Dengue Virus Type 4 Small Plaque Mutants with Restricted Replication in Suckling Mice and in SCID Mice Transplanted with Human Liver Cells", Virology, vol. 300, No. 1, Aug. 15, 2002, pp. 125-139.
Butrapet et al., "Attenuation Markers of a Candidate Dengue Type 2 Vaccine Virus, Strain 16681 (PDK-53), Are Defined by Mutations in the 59 Noncoding Region and Nonstructural Proteins 1 and 3", Journal of Virology, vol. 74, No. 7, Apr. 2000, pp. 3011-3019.
European Application No. 17782757.3 , Extended European Search Report, dated Dec. 2, 2019, 9 pages.
Faye et al., "Quantitative Real-time PCR Detection of Zika Virus and Evaluation with Field-caught Mosquitoes", Virology Journal, vol. 10, No. 311, Oct. 22, 2013, pp. 1-8.
Goh et al., "Molecular Determinants of Plaque Size as an Indicator of Dengue Virus Attenuation", Scientific Reports, vol. 6, No. 26100, May 17, 2016, 11 pages.

(Continued)

*Primary Examiner* — Shanon A. Foley
(74) *Attorney, Agent, or Firm* — Kilpatrick Townsend & Stockton LLP

(57) ABSTRACT

The present invention relates to a method of generating a live attenuated vaccine. The present invention also relates to a live attenuated vaccine produced according to the method of the invention.

17 Claims, 15 Drawing Sheets

Specification includes a Sequence Listing.

(56) References Cited

OTHER PUBLICATIONS

Henchal et al., "Identification of an Antigenic and Genetic Variant of Dengue-4 Virus from the Caribbean", American Journal of Tropical Medicine and Hygiene, vol. 35, No. 2, 1986, pp. 393-400.
Kinney et al., "Construction of Infectious cDNA Clones for Dengue 2 Virus: Strain 16681 and Its Attenuated Vaccine Derivative, Strain PDK-53", Virology, vol. 230, No. 2, Apr. 14, 1997, pp. 300-308.
Lauring et al., "Rationalizing the Development of Live Attenuated Virus Vaccines", Nature Biotechnology, vol. 28, No. 6, Jun. 2010, pp. 573-579.
International Application No. PCT/SG2017/050211 , International Preliminary Report on Patentability, dated Oct. 16, 2018, 11 pages.
International Application No. PCT/SG2017/050211, International Search Report, dated Jul. 7, 2017, 7 pages.
Perez-Cidoncha et al., "Generation of Replication-Proficient Influenza Virus NS1 Point Mutants with Interferon-Hyperinducer Phenotype", PLoS One, vol. 9, Issue 6, e98668, Jun. 2014, 10 pages.
Shan et al., "A Live-attenuated Zika Virus Vaccine Candidate Induces Sterilizing Immunity in Mouse Models", Nature Medicine, vol. 23, No. 6, Jun. 2017, pp. 763-767.
Talon et al., "Influenza A and B Viruses Expressing Altered NS1 Proteins: A Vaccine Approach", PNAS, vol. 97, No. 8, Apr. 11, 2000, pp. 4309-4314.
Trosemeier et al., "Genome Sequence of a Candidate World Health Organization Reference Strain of Zika Virus for Nucleic Acid Testing", Zika virus strain PF13/251013-18, complete genome, Available online at: https://mra.asm.org/content/4/5/e00917-16, Jul. 5, 2016, 6 pages.
Zust et al., "Rational Design of a Live Attenuated Dengue Vaccine: 2'-O-Methyltransferase Mutants Are Highly Attenuated and Immunogenic in Mice and Macaques", PLOS Pathogens, vol. 9, Issue 8, e1003521, Aug. 2013, 13 pages.
Indian Application No. 201817041443, "Office Action", dated Sep. 6, 2022, 12 pages.
Brazilian Application No. BR112018071176-4, "Office Action", dated Aug. 26, 2022, 10 pages.
Chinese Application No. 201780030354.2, "Office Action", dated Aug. 8, 2022, 14 pages.

* cited by examiner

C

A.

B.

| Genome Position | Plaque Size | | Lab Stock Consensus | Amino Acid Change |
|---|---|---|---|---|
| | Big | Small | | |
| 876 | C | T | T | Leucine (C) → Phenylalanine (T) |
| 2925 | G | A | A | Glutamate (G) → Lysine (A) |

C.

| Genome Position | DN-1 | DN-2 | DN-3 | DN-4 | Amino Acid Change |
|---|---|---|---|---|---|
| 876 | T | T | T | T | Phenylalanine |
| 948 | A | G | A | G | Methionine (A) → Valine (G) |
| 2914 | A | A | T | T | Glutamate (A) → Valine (T) |
| 2925 | A | A | A | A | Lysine |

E.

F.

A)

| Genome Position | DV2-3295 (EU081177) | D2-A | D2-B |
|---|---|---|---|
| 4412 | T | C | C |
| 4472 | T | T | C |

B)

| Genome Position | DV4-2270 (GQ398256) | Mutation Identified |
|---|---|---|
| 3436 | T | G |
| 4532 | C | T |
| 6642 | A | G |
| 7142 | C | T |

SEQUENCE LISTING

<160> NUMBER OF SEQ ID NOS: 58

<210> SEQ ID NO 1
<211> LENGTH: 33
<212> TYPE: DNA
<213> ORGANISM: Artificial Sequence
<220> FEATURE:
<223> OTHER INFORMATION: Primer sequence

<400> SEQUENCE: 1
agagctcgtt tagtgaaccg agttgttgat ctg 33

<210> SEQ ID NO 2
<211> LENGTH: 39
<212> TYPE: DNA
<213> ORGANISM: Artificial Sequence
<220> FEATURE:
<223> OTHER INFORMATION: Primer sequence

<400> SEQUENCE: 2
gtggatcaag ttccagcatc atcttagagt tctcagtgc 39

<210> SEQ ID NO 3
<211> LENGTH: 39
<212> TYPE: DNA

<213> ORGANISM: Artificial Sequence
<220> FEATURE:
<223> OTHER INFORMATION: Primer sequence

<400> SEQUENCE: 3
gcactgagaa ctctaagatg atgctggaac ttgatccac 39

<210> SEQ ID NO 4
<211> LENGTH: 40
<212> TYPE: DNA
<213> ORGANISM: Artificial Sequence
<220> FEATURE:
<223> OTHER INFORMATION: Primer sequence

<400> SEQUENCE: 4
cacctgctct ttcaatgtac atgtccacac tctttcctga 40

<210> SEQ ID NO 5
<211> LENGTH: 40
<212> TYPE: DNA
<213> ORGANISM: Artificial Sequence
<220> FEATURE:
<223> OTHER INFORMATION: Primer sequence

<400> SEQUENCE: 5
tcaggaaaga gtgtggacat gtacattgaa agagcaggtg 40

<210> SEQ ID NO 6
<211> LENGTH: 39
<212> TYPE: DNA
<213> ORGANISM: Artificial Sequence
<220> FEATURE:
<223> OTHER INFORMATION: Primer sequence

<400> SEQUENCE: 6
ctaagcttga actctccctc aatggctgct actttgtcg 39

<210> SEQ ID NO 7
<211> LENGTH: 39
<212> TYPE: DNA
<213> ORGANISM: Artificial Sequence
<220> FEATURE:
<223> OTHER INFORMATION: Primer sequence

<400> SEQUENCE: 7
cgacaaagta gcagccattg agggagagtt caagcttag 39

<210> SEQ ID NO 8
<211> LENGTH: 40
<212> TYPE: DNA
<213> ORGANISM: Artificial Sequence
<220> FEATURE:
<223> OTHER INFORMATION: Primer sequence

<400> SEQUENCE: 8
catacggtgt ggtgtcggtc atggctattc ctgtgactcc 40

<210> SEQ ID NO 9
<211> LENGTH: 40
<212> TYPE: DNA
<213> ORGANISM: Artificial Sequence
<220> FEATURE:
<223> OTHER INFORMATION: Primer sequence

<400> SEQUENCE: 9
ggagtcacag gaatagccat gaccgacacc acaccgtatg 40

<210> SEQ ID NO 10
<211> LENGTH: 40
<212> TYPE: DNA
<213> ORGANISM: Artificial Sequence
<220> FEATURE:
<223> OTHER INFORMATION: Primer sequence

<400> SEQUENCE: 10
atgccatgcc gacccagacc catggatttc cccacaccgg 40

<210> SEQ ID NO 11
<211> LENGTH: 40
<212> TYPE: DNA
<213> ORGANISM: Artificial Sequence
<220> FEATURE:
<223> OTHER INFORMATION: Primer sequence

<400> SEQUENCE: 11
tggggaaatc catgggtctg ggtcggcatg gcatctccac 40

<210> SEQ ID NO 12
<211> LENGTH: 38
<212> TYPE: DNA
<213> ORGANISM: Artificial Sequence
<220> FEATURE:
<223> OTHER INFORMATION: Primer sequence

<400> SEQUENCE: 12
cacagatcaa caactcggtt cactaaacga gctctgct 38

<210> SEQ ID NO 13
<211> LENGTH: 17
<212> TYPE: DNA
<213> ORGANISM: Artificial Sequence
<220> FEATURE:
<223> OTHER INFORMATION: Primer sequence

<400> SEQUENCE: 13
ycgytgccca acacaag 17

<210> SEQ ID NO 14
<211> LENGTH: 24
<212> TYPE: DNA
<213> ORGANISM: Artificial Sequence
<220> FEATURE:
<223> OTHER INFORMATION: Primer sequence

<400> SEQUENCE: 14
ccactaaygt tcttttgcag acat 24

<210> SEQ ID NO 15
<211> LENGTH: 31
<212> TYPE: DNA
<213> ORGANISM: Artificial Sequence
<220> FEATURE:
<223> OTHER INFORMATION: Primer sequence

<400> SEQUENCE: 15
agcctacctt gacaagcart cagacactca a 31

<210> SEQ ID NO 16
<211> LENGTH: 21
<212> TYPE: DNA
<213> ORGANISM: Mesocricetus auratus

<400> SEQUENCE: 16
ggaacaaugg gaguucgaat t 21

<210> SEQ ID NO 17
<211> LENGTH: 21
<212> TYPE: DNA
<213> ORGANISM: Mesocricetus auratus

<400> SEQUENCE: 17
uucgaacucc cauuguucct t 21

<210> SEQ ID NO 18
<211> LENGTH: 21
<212> TYPE: DNA
<213> ORGANISM: Mesocricetus auratus

<400> SEQUENCE: 18
ccguuuccau gaccuccuut t 21

<210> SEQ ID NO 19
<211> LENGTH: 21
<212> TYPE: DNA
<213> ORGANISM: Mesocricetus auratus

<400> SEQUENCE: 19
aaggagguca uggaaacggt t 21

<210> SEQ ID NO 20
<211> LENGTH: 21
<212> TYPE: DNA
<213> ORGANISM: Mesocricetus auratus

<400> SEQUENCE: 20
gcauccagac caacaauaat t 21

<210> SEQ ID NO 21
<211> LENGTH: 21
<212> TYPE: DNA
<213> ORGANISM: Mesocricetus auratus

<400> SEQUENCE: 21
uuauuguugg ucuggaugct t 21

<210> SEQ ID NO 22
<211> LENGTH: 21
<212> TYPE: DNA
<213> ORGANISM: Mesocricetus auratus

<400> SEQUENCE: 22
ccucauguuc accgccuuut t 21

<210> SEQ ID NO 23
<211> LENGTH: 21
<212> TYPE: DNA
<213> ORGANISM: Mesocricetus auratus

<400> SEQUENCE: 23
aaaggcggug aacaugaggt t 21

<210> SEQ ID NO 24
<211> LENGTH: 27
<212> TYPE: DNA
<213> ORGANISM: Artificial Sequence -continued
<220> FEATURE:
<223> OTHER INFORMATION: Primer sequence

<400> SEQUENCE: 24
ttgagtaaac yrtgctgcct gtagctc 27

<210> SEQ ID NO 25
<211> LENGTH: 25
<212> TYPE: DNA
<213> ORGANISM: Artificial Sequence
<220> FEATURE:
<223> OTHER INFORMATION: Primer sequence

<400> SEQUENCE: 25
gagacagcag gatctctggt ctytc 25

<210> SEQ ID NO 26
<211> LENGTH: 20
<212> TYPE: DNA
<213> ORGANISM: Artificial Sequence
<220> FEATURE:
<223> OTHER INFORMATION: Primer sequence

<400> SEQUENCE: 26
gagtcaacgg atttggtcgt 20

<210> SEQ ID NO 27
<211> LENGTH: 20
<212> TYPE: DNA
<213> ORGANISM: Artificial Sequence
<220> FEATURE:
<223> OTHER INFORMATION: Primer sequence

<400> SEQUENCE: 27
ttgattttgg agggatctcg 20

<210> SEQ ID NO 28
<211> LENGTH: 23
<212> TYPE: DNA
<213> ORGANISM: Artificial Sequence
<220> FEATURE:
<223> OTHER INFORMATION: Primer sequence

<400> SEQUENCE: 28
ggtgagaaga gatgtctgaa tcc 23

<210> SEQ ID NO 29
<211> LENGTH: 22
<212> TYPE: DNA
<213> ORGANISM: Artificial Sequence
<220> FEATURE:
<223> OTHER INFORMATION: Primer sequence

<400> SEQUENCE: 29
gtccatcctt ggaagcactg ca 22

<210> SEQ ID NO 30
<211> LENGTH: 22
<212> TYPE: DNA
<213> ORGANISM: Artificial Sequence
<220> FEATURE:
<223> OTHER INFORMATION: Primer sequence

<400> SEQUENCE: 30
acacgtccac tgacaggctg tt 22

-continued

<210> SEQ ID NO 31
<211> LENGTH: 22
<212> TYPE: DNA
<213> ORGANISM: Artificial Sequence
<220> FEATURE:
<223> OTHER INFORMATION: Primer sequence

<400> SEQUENCE: 31
atcttccacc gagctgtgtc ca 22

<210> SEQ ID NO 32
<211> LENGTH: 20
<212> TYPE: DNA
<213> ORGANISM: Artificial Sequence
<220> FEATURE:
<223> OTHER INFORMATION: Primer sequence

<400> SEQUENCE: 32
gaagaggaag atttctgaag 20

<210> SEQ ID NO 33
<211> LENGTH: 18
<212> TYPE: DNA
<213> ORGANISM: Artificial Sequence
<220> FEATURE:
<223> OTHER INFORMATION: Primer sequence

<400> SEQUENCE: 33
cattttagtt gccgtagg 18

<210> SEQ ID NO 34
<211> LENGTH: 21
<212> TYPE: DNA
<213> ORGANISM: Artificial Sequence
<220> FEATURE:
<223> OTHER INFORMATION: Primer sequence

<400> SEQUENCE: 34
gctcttgtga ccactacacc a 21

<210> SEQ ID NO 35
<211> LENGTH: 21
<212> TYPE: DNA
<213> ORGANISM: Artificial Sequence
<220> FEATURE:
<223> OTHER INFORMATION: Primer sequence

<400> SEQUENCE: 35
aagaccttct gggtcatcac g 21

<210> SEQ ID NO 36
<211> LENGTH: 22
<212> TYPE: DNA
<213> ORGANISM: Artificial Sequence
<220> FEATURE:
<223> OTHER INFORMATION: Primer sequence

<400> SEQUENCE: 36
ggatggaatg agaccactgt cg 22

<210> SEQ ID NO 37
<211> LENGTH: 22
<212> TYPE: DNA
<213> ORGANISM: Artificial Sequence
<220> FEATURE:
<223> OTHER INFORMATION: Primer sequence

<400> SEQUENCE: 37
acgtcctcca ggattatctc ca 22

<210> SEQ ID NO 38
<211> LENGTH: 10769
<212> TYPE: DNA
<213> ORGANISM: Flavivirus FSME

<400> SEQUENCE: 38
gaatcagact gcgacagttc gagtttgaag cgaaagctag caacagtatc aacaggtttt 60
atttggattt ggaaacgaga gtttctggtc atgaaaaacc caaaaaagaa atccggagga 120
ttccggattg tcaatatgct aaaacgcgga gtagcccgtg tgagcccctt tgggggcttg 180
aagaggctgc cagccggact tctgctgggt catgggccca tcaggatggt cttggcgatt 240
ctagcctttt tgagattcac ggcaatcaag ccatcactgg gtctcatcaa tagatggggt 300
tcagtgggga aaaaagaggc tatggaaata ataaagaagt tcaagaaaga tctggctgcc 360
atgctgagaa taatcaatgc taggaaggag aagaagagac gaggcgcaga tactagtgtc 420
ggaattgttg gcctcctgct gaccacagct atggcagcgg aggtcactag acgtgggagt 480
gcatactata tgtacttgga cagaaacgat gctggggagg ccatatcttt tccaaccaca 540
ttggggatga ataagtgtta tatacagatc atggatcttg gacacatgtg tgatgccacc 600
atgagctatg aatgccctat gctggatgag ggggtggaac cagatgacgt cgattgttgg 660
tgcaacacga cgtcaacttg ggttgtgtac ggaacctgcc atcacaaaaa aggtgaagca 720
cggagatcta gaagagctgt gacgctcccc tcccattcca ctagaaagct gcaaacgcgg 780
tcgcaaacct ggttggaatc aagagaatac acaaagcact tgattagagt cgaaaattgg 840
atattcagga accctggcct cgcgttagca gcagctgcca tcgcttggct tttgggaagc 900
tcaacgagcc aaaaagtcat atacttggtc atgatactgc tgattgcccc ggcatacagc 960
atcaggtgca taggagtcag caatagggac tttgtggaag gtatgtcagg tgggacttgg 1020
gttgatgttg tcttggaaca tggaggttgt gtcaccgtaa tggcacagga caaaccgact 1080
gtcgacatag agctggttac aacaacagtc agcaacatgg cggaggtaag atcctactgc 1140
tatgaggcat caatatcaga catggcttcg gacagccgct gcccaacaca aggtgaagcc 1200
taccttgaca agcaatcaga cactcaatat gtctgcaaaa gaacgttagt ggacagaggc 1260
tggggaaatg gatgtggact ttttggcaaa gggagcctgg tgacatgcgc taagtttgca 1320
tgctccaaga aaatgaccgg gaagagcatc cagccagaga atctggagta ccggataatg 1380
ctgtcagttc atggctccca gcacagtggg atgatcgtta atgacacagg acatgaaact 1440
gatgagaata gagcgaaggt tgagataacg cccaattcac caagagccga agccaccctg 1500
gggggttttg gaagcctagg acttgattgt gaaccgagga caggccttga cttttcagat 1560
ttgtattact tgactatgaa taacaagcac tggttggttc acaaggagtg gttccacgac 1620
attccattac cttggcacgc tggggcagac accggaactc cacactggaa caacaaagaa 1680
gcactggtag agttcaagga cgcacatgcc aaaaggcaaa ctgtcgtggt tctagggagt 1740
caagaaggag cagttcacac ggcccttgct ggagctctgg aggctgagat ggatggtgca 1800
aagggaaggc tgtcctctgg ccacttgaaa tgtcgcctga aaatggataa acttagattg 1860
aagggcgtgt catactcctt gtgtaccgca gcgttcacat tcaccaagat cccggctgaa 1920
acactgcacg ggacagtcac agtggaggta cagtacgcag ggacagatgg accttgcaag 1980

-continued

```
gttccagctc agatggcggt ggacatgcaa actctgaccc cagttgggag gttgataacc   2040
gctaaccccg taatcactga aagcactgag aactctaaga tgatgctgga acttgatcca   2100
ccatttgggg actcttacat tgtcatagga gtcggggaga agaagatcac ccaccactgg   2160
cacaggagtg gcagcaccat tggaaaagca tttgaagcca ctgtgagagg tgccaagaga   2220
atggcagtct tgggagacac agcctgggac tttggatcag ttggaggcgc tctcaactca   2280
ttgggcaagg gcatccatca aatttttgga gcagctttca aatcattgtt tggaggaatg   2340
tcctggttct cacaaattct cattggaacg ttgctgatgt ggttgggtct gaacacaaag   2400
aatggatcta tttcccttat gtgcttggcc ttagggggag tgttgatctt cttatccaca   2460
gccgtctctg ctgatgtggg gtgctcggtg gacttctcaa agaaggagac gagatgcggt   2520
acaggggtgt tcgtctataa cgacgttgaa gcctggaggg acaggtacaa gtaccatcct   2580
gactcccccc gtagattggc agcagcagtc aagcaagcct gggaagatgg tatctgtggg   2640
atctcctctg tttcaagaat ggaaaacatc atgtggagat cagtagaagg ggagctcaac   2700
gcaatcctgg aagagaatgg agttcaactg acggtcgttg tgggatctgt aaaaaacccc   2760
atgtggagag gtccacagag attgcccgtg cctgtgaacg agctgcccca cggctggaag   2820
gcttggggga aatcgtactt cgtcagagca gcaaagacaa ataacagctt tgtcgtggat   2880
ggtgacacac tgaaggaatg cccactcgaa catagagcat ggaacagctt tcttgtggag   2940
gatcatgggt tcggggtatt tcacactagt gtctggctca aggttagaga agattattca   3000
ttagagtgtg atccagccgt tattggaaca gctgttaagg gaaaggaggc tgtacacagt   3060
gatctaggct actggattga gagtgagaag aatgacacat ggaggctgaa gagggcccat   3120
ctgatcgaga tgaaaacatg tgaatggcca aagtcccaca cattgtggac agatggaata   3180
gaagagagtg atctgatcat acccaagtct ttagctgggc cactcagcca tcacaatacc   3240
agagagggct acaggaccca aatgaaaggg ccatggcaca gtgaagagct tgaaattcgg   3300
tttgaggaat gcccaggcac taaggtccac gtggaggaaa catgtggaac aagaggacca   3360
tctctgagat caaccactgc aagcggaagg gtgatcgagg aatggtgctg cagggagtgc   3420
acaatgcccc cactgtcgtt ccgggctaaa gatggctgtt ggtatggaat ggagataagg   3480
cccaggaaag aaccagaaag taacttagta aggtcaatgg tgactgcagg atcaactgat   3540
cacatggatc acttctccct tggagtgctt gtgattctgc tcatggtgca ggaagggctg   3600
aagaagagaa tgaccacaaa gatcatcata agcacatcaa tggcagtgct ggtagctatg   3660
atcctgggag gattttcaat gagtgacctg gctaagcttg caattttgat gggtgccacc   3720
ttcgcggaaa tgaacactgg aggagatgta gctcatctgg cgctgatagc ggcattcaaa   3780
gtcagaccag cgttgctggt atctttcatc ttcagagcta attggacacc ccgtgaaagc   3840
atgctgctgg ccttggcctc gtgtcttttg caaactgcga tctccgcctt ggaaggcgac   3900
ctgatggttc tcatcaatgg ttttgctttg gcctggttgg caatacgagc gatggttgtt   3960
ccacgcactg ataacatcac cttggcaatc ctggctgctc tgacaccact ggcccggggc   4020
acactgcttg tggcgtggag agcaggcctt gctacttgcg gggggtttat gctcctctct   4080
ctgaagggaa aaggcagtgt gaagaagaac ttaccatttg tcatggccct gggactaacc   4140
gctgtgaggc tggtcgaccc catcaacgtg gtgggactgc tgttgctcac aaggagtggg   4200
aagcggagct ggcccccctag cgaagtactc acagctgttg gcctgatatg cgcattggct   4260
ggagggttcg ccaaggcaga tatagagatg gctgggccca tggccgcggt cggtctgcta   4320
attgtcagtt acgtggtctc aggaaagagt gtggacatgt acattgaaag agcaggtgac   4380
```

-continued

```
atcacatggg aaaaagatgc ggaagtcact ggaaacagtc cccggctcga tgtggcgcta   4440
gatgagagtg gtgatttctc cctggtggag gatgacggtc cccccatgag agagatcata   4500
ctcaaggtgg tcctgatgac catctgtggc atgaacccaa tagccatacc ctttgcagct   4560
ggagcgtggt acgtatacgt gaagactgga aaaaggagtg gtgctctatg ggatgtgcct   4620
gctcccaagg aagtaaaaaa gggggagacc acagatggag tgtacagagt aatgactcgt   4680
agactgctag gttcaacaca agttggagtg ggagttatgc aagagggggt ctttcacact   4740
atgtggcacg tcacaaaagg atccgcgctg agaagcggtg aagggagact tgatccatac   4800
tggggagatg tcaagcagga tctggtgtca tactgtggtc catggaagct agatgccgcc   4860
tgggacgggc acagcgaggt gcagctcttg gccgtgcccc ccggagagag agcgaggaac   4920
atccagactc tgcccggaat atttaagaca aaggatgggg acattggagc ggttgcgctg   4980
gattacccag caggaacttc aggatctcca atcctagaca agtgtgggag agtgatagga   5040
ctttatggca atggggtcgt gatcaaaaat gggagttatg ttagtgccat cacccaaggg   5100
aggagggagg aagagactcc tgttgagtgc ttcgagcctt cgatgctgaa gaagaagcag   5160
ctaactgtct tagacttgca tcctggagct gggaaaacca ggagagttct tcctgaaata   5220
gtccgtgaag ccataaaaac aagactccgt actgtgatct tagctccaac cagggttgtc   5280
gctgctgaaa tggaggaagc ccttagaggg cttccagtgc gttatatgac aacagcagtc   5340
aatgtcaccc actctggaac agaaatcgtc gacttaatgt gccatgccac cttcacttca   5400
cgtctactac agccaatcag agtccccaac tataatctgt atattatgga tgaggcccac   5460
ttcacagatc cctcaagtat agcagcaaga ggatacattt caacaagggt tgagatgggc   5520
gaggcggctg ccatcttcat gaccgccacg ccaccaggaa cccgtgacgc atttccggac   5580
tccaactcac caattatgga caccgaagtg gaagtcccag agagagcctg gagctcaggc   5640
tttgattggg tgacggatca ttctggaaaa acagtttggt ttgttccaag cgtgaggaac   5700
ggcaatgaga tcgcagcttg tctgacaaag gctggaaaac gggtcataca gctcagcaga   5760
aagacttttg agacagagtt ccagaaaaca aaacatcaag agtgggactt tgtcgtgaca   5820
actgacattt cagagatggg cgccaacttt aaagctgacc gtgtcataga ttccaggaga   5880
tgcctaaagc cggtcatact tgatggcgag agagtcattc tggctggacc catgcctgtc   5940
acacatgcca gcgctgccca gaggaggggg cgcataggca ggaatcccaa caaacctgga   6000
gatgagtatc tgtatggagg tgggtgcgca gagactgacg aagaccatgc acactggctt   6060
gaagcaagaa tgctccttga caatatttac ctccaagatg gcctcatagc ctcgctctat   6120
cgacctgagg ccgacaaagt agcagccatt gagggagagt tcaagcttag gacggagcaa   6180
aggaagacct ttgtggaact catgaaaaga ggagatcttc ctgtttggct ggcctatcag   6240
gttgcatctg ccggaataac ctacacagat agaagatggt gctttgatgg cacgaccaac   6300
aacaccataa tggaagacag tgtgccggca gaggtgtgga ccagacacgg agagaaaaga   6360
gtgctcaaac cgaggtggat ggacgccaga gtttgttcag atcatgcggc cctgaagtca   6420
ttcaaggagt ttgccgctgg gaaaagagga gcggcttttg gagtgatgga agccctggga   6480
acactgccag gacacatgac agagagattc caggaagcca ttgacaacct cgctgtgctc   6540
atgcgggcag agactggaag caggccttac aaagccgcgg cggcccaatt gccggagacc   6600
ctagagacca ttatgctttt ggggttgctg ggaacagtct cgctgggaat ctttttcgtc   6660
ttgatgagga acaagggcat agggaagatg ggctttggaa tggtgactct tggggccagc   6720
```

-continued

```
gcatggctca tgtggctctc ggaaattgag ccagccagaa ttgcatgtgt cctcattgtt   6780
gtgttcctat tgctggtggt gctcatacct gagccagaaa agcaaagatc tccccaggac   6840
aaccaaatgg caatcatcat catggtagca gtaggtcttc tgggcttgat taccgccaat   6900
gaactcggat ggttggagag aacaaagagt gacctaagcc atctaatggg aaggagagag   6960
gagggggcaa ccataggatt ctcaatggac attgacctgc ggccagcctc agcttgggcc   7020
atctatgctg ccttgacaac tttcattacc ccagccgtcc aacatgcagt gaccacttca   7080
tacaacaact actccttaat ggcgatggcc acgcaagctg gagtgttgtt tggtatgggc   7140
aaagggatgc cattctacgc atgggacttt ggagtcccgc tgctaatgat aggttgctac   7200
tcacaattaa cacccctgac cctaatagtg gccatcattt tgctcgtggc gcactacatg   7260
tacttgatcc cagggctgca ggcagcagct gcgcgtgctg cccagaagag aacggcagct   7320
ggcatcatga agaaccctgt tgtggatgga atagtggtga ctgacattga cacaatgaca   7380
attgaccccc aagtggagaa aaagatggga caggtgctac tcatagcagt agccgtctcc   7440
agcgccatac tgtcgcggac cgcctggggg tgggggggagg ctggggccct gatcacagct   7500
gcaacttcca ctttgtggga aggctctccg aacaagtact ggaactcctc tacagccact   7560
tcactgtgta acattttttag gggaagttac ttggctggag cttctctaat ctacacagta   7620
acaagaaacg ctggcttggt caagagacgt gggggtggaa caggagagac cctgggagag   7680
aaatggaagg cccgcttgaa ccagatgtcg gccctggagt tctactccta caaaaagtca   7740
ggcatcaccg aggtgtgcag agaagaggcc cgccgcgccc tcaaggacgg tgtggcaacg   7800
ggaggccatg ctgtgtcccg aggaagtgca aagctgagat ggttggtgga gcggggatac   7860
ctgcagccct atggaaaggt cattgatctt ggatgtggca gagggggctg gagttactac   7920
gccgccacca tccgcaaagt tcaagaagtg aaaggataca caaaaggagg ccctggtcat   7980
gaagaaccca tgttggtgca aagctatggg tggaacatag tccgtcttaa gagtggggtg   8040
gacgtctttc atatggcggc tgagccgtgt gacacgttgc tgtgtgacat aggtgagtca   8100
tcatctagtc ctgaagtgga agaagcacgg acgctcagag tcctctccat ggtgggggat   8160
tggcttgaaa aaagaccagg agccttttgt ataaaagtgt tgtgcccata caccagcact   8220
atgatggaaa ccctggagcg actgcagcgt aggtatgggg gaggactggt cagagtgcca   8280
ctctcccgca actctacaca tgagatgtac tgggtctctg gagcgaaaag caacaccata   8340
aaaagtgtgt ccaccacgag ccagctcctc ttggggcgca tggacgggcc caggaggcca   8400
gtgaaatatg aggaggatgt gaatctcggc tctggcacgc gggctgtggt aagctgcgct   8460
gaagctccca acatgaagat cattggtaac cgcattgaaa ggatccgcag tgagcacgcg   8520
gaaacgtggt tctttgacga gaaccaccca tataggacat gggcttacca tggaagctat   8580
gaggccccca cacaagggtc agcgtcctct ctaataaacg ggg ttgtcag gctcctgtca   8640
aaaccctggg atgtggtgac tggagtcaca ggaatagcca tgaccgacac cacaccgtat   8700
ggtcagcaaa gagttttcaa ggaaaaagtg gacactaggg tgccagaccc ccaagaaggc   8760
actcgtcagg ttatgagcat ggtctcttcc tggttgtgga aagagctagg caaacacaaa   8820
cggccacgag tctgtaccaa agaagagttc atcaacaagg ttcgtagcaa tgcagcatta   8880
ggggcaatat ttgaagagga aaaagagtgg aagactgcag tggaagctgt gaacgatcca   8940
aggttctggg ctctagtgga caaggaaaga gagcaccacc tgagaggaga gtgccagagt   9000
tgtgtgtaca acatgatggg aaaaagagaa aagaaacaag gggaatttgg aaaggccaag   9060
ggcagccgcg ccatctggta tatgtggcta ggggctagat ttctagagtt cgaagccctt   9120
```

ggattcttga acgaggatca ctggatgggg agagagaact caggaggtgg tgttgaaggg 9180
ctgggattac aaagactcgg atatgtccta gaagagatga gtcgcatacc aggaggaagg 9240
atgtatgcag atgacactgc tggctgggac acccgcatca gcaggtttga tctggagaat 9300
gaagctctaa tcaccaacca aatggagaaa gggcacaggg ccttggcatt ggccataatc 9360
aagtacacat accaaaacaa agtggtaaag gtccttagac cagctgaaaa agggaagaca 9420
gttatggaca ttatttcgag acaagaccaa agggggagcg gacaagttgt cacttacgct 9480
cttaacacat ttaccaacct agtggtgcaa ctcattcgga atatggaggc tgaggaagtt 9540
ctagagatgc aagacttgtg gctgctgcgg aggtcagaga aagtgaccaa ctggttgcag 9600
agcaacggat gggataggct caaacgaatg gcagtcagtg gagatgattg cgttgtgaag 9660
ccaattgatg ataggtttgc acatgccctc aggttcttga atgatatggg aaaagttagg 9720
aaggacacac aagagtggaa accctcaact ggatgggaca actgggaaga agttccgttt 9780
tgctcccacc acttcaacaa gctccatctc aaggacggga ggtccattgt ggttccctgc 9840
cgccaccaag atgaactgat tggccgggcc cgcgtctctc caggggcggg atggagcatc 9900
cgggagactg cttgcctagc aaaatcatat gcgcaaatgt ggcagctcct ttatttccac 9960
agaagggacc tccgactgat ggccaatgcc atttgttcat ctgtgccagt tgactgggtt 10020
ccaactggga gaactacctg gtcaatccat ggaaagggag aatggatgac cactgaagac 10080
atgcttgtgg tgtggaacag agtgtggatt gaggagaacg accacatgga agacaagacc 10140
ccagttacga aatggacaga cattccctat ttgggaaaaa gggaagactt gtggtgtgga 10200
tctctcatag ggcacagacc gcgcaccacc tgggctgaga acattaaaaa cacagtcaac 10260
atggtgcgca ggatcatagg tgatgaagaa aagtacatgg actacctatc cacccaagtt 10320
cgctacttgg gtgaagaagg gtctacacct ggagtgctgt aagcaccaat cttagtgttg 10380
tcaggcctgc tagtcagcca cagcttgggg aaagctgtgc agcctgtgac ccccccagga 10440
gaagctggga aaccaagcct atagtcaggc cgagaacgcc atggcacgga agaagccatg 10500
ctgcctgtga gcccctcaga ggacactgag tcaaaaaacc ccacgcgctt ggaggcgcag 10560
gatgggaaaa gaaggtggcg accttcccca cccttcaatc tggggcctga actggagatc 10620
agctgtggat ctccagaaga gggactagtg gttagaggag acccccccgga aaacgcaaaa 10680 cagcatattg acgctgggaa agaccagaga ctccatgagt ttccaccacg ctggccgcca 10740
ggcacagatc gccgaatagc ggcggccgg 10769

<210> SEQ ID NO 39
<211> LENGTH: 10807
<212> TYPE: DNA
<213> ORGANISM: Flavivirus FSME

<400> SEQUENCE: 39
agttgttgat ctgtgtgaat cagactgcga cagttcgagt ttgaagcgaa agctagcaac 60
agtatcaaca ggttttattt tggatttgga aacgagagtt tctggtcatg aaaaacccaa 120
aaaagaaatc cggaggattc cggattgtca atatgctaaa acgcggagta gcccgtgtga 180
gcccctttgg gggcttgaag aggctgccag ccggacttct gctgggtcat gggcccatca 240
ggatggtctt ggcgattcta gcctttttga gattcacggc aatcaagcca tcactgggtc 300
tcatcaatag atggggttca gtggggaaaa aagaggctat ggaaataata aagaagttca 360
agaaagatct ggctgccatg ctgagaataa tcaatgctag gaaggagaag aagagacgag 420

-continued

```
gcgcagatac tagtgtcgga attgttggcc tcctgctgac cacagctatg gcagcggagg    480
tcactagacg tgggagtgca tactatatgt acttggacag aaacgatgct ggggaggcca    540
tatcttttcc aaccacattg ggatgaata agtgttatat acagatcatg gatcttggac    600
acatgtgtga tgccaccatg agctatgaat gccctatgct ggatgagggg gtggaaccag    660
atgacgtcga ttgttggtgc aacacgacgt caacttgggt tgtgtacgga acctgccatc    720
acaaaaaagg tgaagcacgg agatctagaa gagctgtgac gctcccctcc cattccacta    780
gaaagctgca aacgcggtcg caaacctggt tggaatcaag agaatacaca aagcacttga    840
ttagagtcga aaattggata ttcaggaacc ctggcttcgc gttagcagca gctgccatcg    900
cttggctttt gggaagctca acgagccaaa aagtcatata cttggtcatg atactgctga    960
ttgccccggc atacagcatc aggtgcatag gagtcagcaa tagggacttt gtggaaggta   1020
tgtcaggtgg gacttgggtt gatgttgtct tggaacatgg aggttgtgtc accgtaatgg   1080
cacaggacaa accgactgtc gacatagagc tggttacaac aacagtcagc aacatggcgg   1140
aggtaagatc ctactgctat gaggcatcaa tatcagacat ggcttcggac agccgctgcc   1200
caacacaagg tgaagcctac cttgacaagc aatcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaggttga gataacgccc aattcaccaa   1500
gagccgaagc caccctgggg ggttttggaa gcctaggact tgattgtgaa ccgaggacag   1560
gccttgactt ttcagatttg tattacttga ctatgaataa caagcactgg ttggttcaca   1620
aggagtggtt ccacgacatt ccattacctt ggcacgctgg ggcagacacc ggaactccac   1680
actggaacaa caaagaagca ctggtagagt tcaaggacgc acatgccaaa aggcaaactg   1740
tcgtggttct agggagtcaa gaaggagcag ttcacacggc ccttgctgga gctctggagg   1800
ctgagatgga tggtgcaaag ggaaggctgt cctctggcca cttgaaatgt cgcctgaaaa   1860
tggataaact tagattgaag ggcgtgtcat actccttgtg taccgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga catgcaaact ctgaccccag   2040
ttgggaggtt gataaccgct aaccccgtaa tcactgaaag cactgagaac tctaagatga   2100
tgctggaact tgatccacca tttggggact cttacattgt cataggagtc ggggagaaga   2160
agatcaccca ccactggcac aggagtggca gcaccattgg aaaagcattt gaagccactg   2220
tgagaggtgc caagagaatg gcagtcttgg gagacacagc ctgggacttt ggatcagttg   2280
gaggcgctct caactcattg ggcaagggca tccatcaaat ttttggagca gctttcaaat   2340
cattgtttgg aggaatgtcc tggttctcac aaattctcat tggaacgttg ctgatgtggt   2400
tgggtctgaa cacaaagaat ggatctattt cccttatgtg cttggcctta gggggagtgt   2460
tgatcttctt atccacagcc gtctctgctg atgtggggtg ctcggtggac ttctcaaaga   2520
aggagacgag atgcggtaca ggggtgttcg tctataacga cgttgaagcc tggagggaca   2580
ggtacaagta ccatcctgac tccccccgta gattggcagc agcagtcaag caagcctggg   2640
aagatggtat ctgtgggatc tcctctgttt caagaatgga aaacatcatg tggagatcag   2700
tagaagggga gctcaacgca atcctggaag agaatggagt tcaactgacg gtcgttgtgg   2760
gatctgtaaa aaaccccatg tggagaggtc cacagagatt gcccgtgcct gtgaacgagc   2820
```

-continued

```
tgccccacgg ctggaaggct tgggggaaat cgtacttcgt cagagcagca aagacaaata   2880
acagctttgt cgtggatggt gacacactga aggaatgccc actcaaacat agagcatgga   2940
acagctttct tgtggaggat catgggttcg ggtatttca cactagtgtc tggctcaagg   3000
ttagagaaga ttattcatta gagtgtgatc cagccgttat tggaacagct gttaagggaa   3060
aggaggctgt acacagtgat ctaggctact ggattgagag tgagaagaat gacacatgga   3120
ggctgaagag ggcccatctg atcgagatga aaacatgtga atggccaaag tcccacacat   3180
tgtggacaga tggaatagaa gagagtgatc tgatcatacc caagtcttta gctgggccac   3240
tcagccatca caataccaga gagggctaca ggacccaaat gaaagggcca tggcacagtg   3300
aagagcttga aattcggttt gaggaatgcc caggcactaa ggtccacgtg gaggaaacat   3360
gtggaacaag aggaccatct ctgagatcaa ccactgcaag cggaagggtg atcgaggaat   3420
ggtgctgcag ggagtgcaca atgcccccac tgtcgttccg ggctaaagat ggctgttggt   3480
atggaatgga gataaggccc aggaaagaac cagaaagtaa cttagtaagg tcaatggtga   3540
ctgcaggatc aactgatcac atggatcact tctcccttgg agtgcttgtg attctgctca   3600
tggtgcagga agggctgaag aagagaatga ccacaaagat catcataagc acatcaatgg   3660
cagtgctggt agctatgatc ctgggaggat tttcaatgag tgacctggct aagcttgcaa   3720
ttttgatggg tgccaccttc gcggaaatga acactggagg agatgtagct catctggcgc   3780
tgatagcggc attcaaagtc agaccagcgt tgctggtatc tttcatcttc agagctaatt   3840
ggacaccccg tgaaagcatg ctgctggcct tggcctcgtg tcttttgcaa actgcgatct   3900
ccgccttgga aggcgacctg atggttctca tcaatggttt tgctttggcc tggttggcaa   3960
tacgagcgat ggttgttcca cgcactgata acatcacctt ggcaatcctg gctgctctga   4020
caccactggc ccggggcaca ctgcttgtgg cgtggagagc aggccttgct acttgcgggg   4080
ggtttatgct cctctctctg aagggaaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc cccctagcga agtactcaca gctgttggcc   4260
tgatatgcgc attggctgga gggttcgcca aggcagatat agagatggct gggcccatgg   4320
ccgcggtcgg tctgctaatt gtcagttacg tggtctcagg aaagagtgtg gacatgtaca   4380
ttgaaagagc aggtgacatc acatgggaaa aagatgcgga agtcactgga aacagtcccc   4440
ggctcgatgt ggcgctagat gagagtggtg atttctccct ggtggaggat gacggtcccc   4500
ccatgagaga gatcatactc aaggtggtcc tgatgaccat ctgtggcatg aacccaatag   4560
ccataccctt tgcagctgga gcgtggtacg tatacgtgaa gactggaaaa aggagtggtg   4620
ctctatggga tgtgcctgct cccaaggaag taaaaaaggg ggagaccaca gatggagtgt   4680
acagagtaat gactcgtaga ctgctaggtt caacacaagt tggagtggga gttatgcaag   4740
agggggtctt tcacactatg tggcacgtca caaaaggatc cgcgctgaga agcggtgaag   4800
ggagacttga tccatactgg ggagatgtca agcaggatct ggtgtcatac tgtggtccat   4860
ggaagctaga tgccgcctgg gacgggcaca gcgaggtgca gctcttggcc gtgccccccg   4920
gagagagagc gaggaacatc cagactctgc ccggaatatt taagacaaag gatggggaca   4980
ttggagcggt tgcgctggat tacccagcag gaacttcagg atctccaatc ctagacaagt   5040
gtgggagagt gataggactt tatggcaatg gggtcgtgat caaaaatggg agttatgtta   5100
gtgccatcac ccaagggagg agggaggaag agactcctgt tgagtgcttc gagccttcga   5160
```

-continued

```
tgctgaagaa gaagcagcta actgtcttag acttgcatcc tggagctggg aaaaccagga   5220
gagttcttcc tgaaatagtc cgtgaagcca taaaaacaag actccgtact gtgatcttag   5280
ctccaaccag ggttgtcgct gctgaaatgg aggaagccct tagagggctt ccagtgcgtt   5340
atatgacaac agcagtcaat gtcacccact ctggaacaga aatcgtcgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcggctgcca tcttcatgac cgccacgcca ccaggaaccc   5580
gtgacgcatt tccggactcc aactcaccaa ttatggacac cgaagtggaa gtcccagaga   5640
gagcctggag ctcaggcttt gattgggtga cggatcattc tggaaaaaca gtttggtttg   5700
ttccaagcgt gaggaacggc aatgagatcg cagcttgtct gacaaaggct ggaaaacggg   5760
tcatacagct cagcagaaag acttttgaga cagagttcca gaaaacaaaa catcaagagt   5820
gggactttgt cgtgacaact gacatttcag agatgggcgc caactttaaa gctgaccgtg   5880
tcatagattc caggagatgc ctaaagccgg tcatacttga tggcgagaga gtcattctgg   5940
ctggacccat gcctgtcaca catgccagcg ctgcccagag gagggggcgc ataggcagga   6000
atcccaacaa acctggagat gagtatctgt atggaggtgg gtgcgcagag actgacgaag   6060
accatgcaca ctggcttgaa gcaagaatgc tccttgacaa tatttacctc caagatggcc   6120
tcatagcctc gctctatcga cctgaggccg acaaagtagc agccattgag ggagagttca   6180
agcttaggac ggagcaaagg aagacctttg tggaactcat gaaaagagga gatcttcctg   6240
tttggctggc ctatcaggtt gcatctgccg gaataaccta cacagataga agatggtgct   6300
ttgatggcac gaccaacaac accataatgg aagacagtgt gccggcagag gtgtggacca   6360
gacacggaga gaaaagagtg ctcaaaccga ggtggatgga cgccagagtt tgttcagatc   6420
atgcggccct gaagtcattc aaggagtttg ccgctgggaa aagaggagcg gcttttggag   6480
tgatggaagc cctgggaaca ctgccaggac acatgacaga gagattccag gaagccattg   6540
acaacctcgc tgtgctcatg cgggcagaga ctggaagcag gccttacaaa gccgcggcgg   6600
cccaattgcc ggagacccta gagaccatta tgcttttggg gttgctggga acagtctcgc   6660
tgggaatctt tttcgtcttg atgaggaaca agggcatagg gaagatgggc tttggaatgg   6720
tgactcttgg ggccagcgca tggctcatgt ggctctcgga aattgagcca gccagaattg   6780
catgtgtcct cattgttgtg ttcctattgc tggtggtgct catacctgag ccagaaaagc   6840
aaagatctcc ccaggacaac caaatggcaa tcatcatcat ggtagcagta ggtcttctgg   6900
gcttgattac cgccaatgaa ctcggatggt tggagagaac aaagagtgac ctaagccatc   6960
taatgggaag gagagaggag ggggcaacca taggattctc aatggacatt gacctgcggc   7020
cagcctcagc ttgggccatc tatgctgcct tgacaacttt cattacccca gccgtccaac   7080
atgcagtgac cacttcatac aacaactact ccttaatggc gatggccacg caagctggag   7140
tgttgtttgg tatgggcaaa gggatgccat tctacgcatg ggactttgga gtcccgctgc   7200
taatgatagg ttgctactca caattaacac ccctgaccct aatagtggcc atcattttgc   7260
tcgtggcgca ctacatgtac ttgatcccag ggctgcaggc agcagctgcg cgtgctgccc   7320
agaagagaac ggcagctggc atcatgaaga accctgttgt ggatggaata gtggtgactg   7380
acattgacac aatgacaatt gacccccaag tggagaaaaa gatgggacag gtgctactca   7440
tagcagtagc cgtctccagc gccatactgt cgcggaccgc ctgggggtgg ggggaggctg   7500
gggccctgat cacagctgca acttccactt tgtgggaagg ctctccgaac aagtactgga   7560
```

-continued

```
actcctctac agccacttca ctgtgtaaca tttttagggg aagttacttg gctggagctt   7620
ctctaatcta cacagtaaca agaaacgctg gcttggtcaa gagacgtggg ggtggaacag   7680
gagagaccct gggagagaaa tggaaggccc gcttgaacca gatgtcggcc ctggagttct   7740
actcctacaa aaagtcaggc atcaccgagg tgtgcagaga agaggcccgc cgcgccctca   7800
aggacggtgt ggcaacggga ggccatgctg tgtcccgagg aagtgcaaag ctgagatggt   7860
tggtggagcg gggatacctg cagccctatg gaaaggtcat tgatcttgga tgtggcagag   7920
ggggctggag ttactacgcc gccaccatcc gcaaagttca agaagtgaaa ggatacacaa   7980
aaggaggccc tggtcatgaa gaacccatgt tggtgcaaag ctatgggtgg aacatagtcc   8040
gtcttaagag tggggtggac gtctttcata tggcggctga gccgtgtgac acgttgctgt   8100
gtgacatagg tgagtcatca tctagtcctg aagtggaaga agcacggacg ctcagagtcc   8160
tctccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag agtgccactc tcccgcaact ctacacatga gatgtactgg gtctctggag   8340
cgaaaagcaa caccataaaa agtgtgtcca ccacgagcca gctcctcttg ggcgcatgg    8400
acgggcccag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagaccccca agaaggcact cgtcaggtta tgagcatggt ctcttcctgg ttgtggaaag   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagttgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttgaacg aggatcactg gatggggaga gagaactcag   9180
gaggtggtgt tgaagggctg ggattacaaa gactcggata tgtcctagaa gagatgagtc   9240
gcataccagg aggaaggatg tatgcagatg acactgctgg ctgggacacc cgcatcagca   9300
ggtttgatct ggagaatgaa gctctaatca ccaaccaaat ggagaaaggg cacagggcct   9360
tggcattggc cataatcaag tacacatacc aaaacaaagt ggtaaaggtc cttagaccag   9420
ctgaaaaagg gaagacagtt atggacatta tttcgagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa acgaatggca gtcagtggag   9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
gggaagaagt tccgttttgc tcccaccact tcaacaagct ccatctcaag gacgggaggt   9840
ccattgtggt tccctgccgc caccaagatg aactgattgg ccgggcccgc gtctctccag   9900
```

-continued gggcgggatg gagcatccgg gagactgctt gcctagcaaa atcatatgcg caaatgtggc 9960
agctccttta tttccacaga agggacctcc gactgatggc caatgccatt tgttcatctg 10020
tgccagttga ctgggttcca actgggagaa ctacctggtc aatccatgga aagggagaat 10080
ggatgaccac tgaagacatg cttgtggtgt ggaacagagt gtggattgag gagaacgacc 10140
acatggaaga caagacccca gttacgaaat ggacagacat tccctatttg ggaaaaaggg 10200
aagacttgtg gtgtggatct ctcatagggc acagaccgcg caccacctgg gctgagaaca 10260
ttaaaaacac agtcaacatg gtgcgcagga tcataggtga tgaagaaaag tacatggact 10320
acctatccac ccaagttcgc tacttgggtg aagaagggtc tacacctgga gtgctgtaag 10380
caccaatctt agtgttgtca ggcctgctag tcagccacag cttggggaaa gctgtgcagc 10440
ctgtgacccc cccaggagaa gctgggaaac caagcctata gtcaggccga gaacgccatg 10500
gcacggaaga agccatgctg cctgtgagcc cctcagagga cactgagtca aaaaacccca 10560
cgcgcttgga ggcgcaggat gggaaaagaa ggtggcgacc ttccccaccc ttcaatctgg 10620
ggcctgaact ggagatcagc tgtggatctc cagaagaggg actagtggtt agaggagacc 10680
ccccggaaaa cgcaaaacag catattgacg ctgggaaaga ccagagactc catgagtttc 10740
caccacgctg gccgccaggc acagatcgcc gaatagcggc ggccggtgtg gggaaatcca 10800
tgggtct 10807

<210> SEQ ID NO 40
<211> LENGTH: 10807
<212> TYPE: DNA
<213> ORGANISM: Flavivirus FSME

<400> SEQUENCE: 40
agttgttgat ctgtgtgaat cagactgcga cagttcgagt ttgaagcgaa agctagcaac 60
agtatcaaca ggttttattt tggatttgga aacgagagtt tctggtcatg aaaaacccaa 120
aaaagaaatc cggaggattc cggattgtca atatgctaaa acgcggagta gcccgtgtga 180
gcccctttgg gggcttgaag aggctgccag ccggacttct gctgggtcat gggcccatca 240
ggatggtctt ggcgattcta gcctttttga gattcacggc aatcaagcca tcactgggtc 300
tcatcaatag atggggttca gtggggaaaa aagaggctat ggaaataata aagaagttca 360
agaaagatct ggctgccatg ctgagaataa tcaatgctag gaaggagaag aagagacgag 420
gcgcagatac tagtgtcgga attgttggcc tcctgctgac cacagctatg gcagcggagg 480
tcactagacg tgggagtgca tactatatgt acttggacag aaacgatgct ggggaggcca 540
tatcttttcc aaccacattg gggatgaata agtgttatat acagatcatg gatcttggac 600
acatgtgtga tgccaccatg agctatgaat gccctatgct ggatgagggg gtggaaccag 660
atgacgtcga ttgttggtgc aacacgacgt caacttgggt tgtgtacgga acctgccatc 720
acaaaaaagg tgaagcacgg agatctagaa gagctgtgac gctcccctcc cattccacta 780
gaaagctgca aacgcggtcg caaacctggt tggaatcaag agaatacaca aagcacttga 840
ttagagtcga aaattggata ttcaggaacc ctggcttcgc gttagcagca gctgccatcg 900
cttggctttt gggaagctca acgagccaaa aagtcatata cttggtcgtg atactgctga 960
ttgccccggc atacagcatc aggtgcatag gagtcagcaa tagggacttt gtggaaggta 1020
tgtcaggtgg gacttgggtt gatgttgtct tggaacatgg aggttgtgtc accgtaatgg 1080
cacaggacaa accgactgtc gacatagagc tggttacaac aacagtcagc aacatggcgg 1140
aggtaagatc ctactgctat gaggcatcaa tatcagacat ggcttcggac agccgctgcc 1200

-continued

```
caacacaagg tgaagcctac cttgacaagc aatcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaggttga gataacgccc aattcaccaa   1500
gagccgaagc caccctgggg ggttttggaa gcctaggact tgattgtgaa ccgaggacag   1560
gccttgactt ttcagatttg tattacttga ctatgaataa caagcactgg ttggttcaca   1620
aggagtggtt ccacgacatt ccattacctt ggcacgctgg ggcagacacc ggaactccac   1680
actggaacaa caaagaagca ctggtagagt tcaaggacgc acatgccaaa aggcaaactg   1740
tcgtggttct agggagtcaa gaaggagcag ttcacacggc ccttgctgga gctctggagg   1800
ctgagatgga tggtgcaaag ggaaggctgt cctctggcca cttgaaatgt cgcctgaaaa   1860
tggataaact tagattgaag ggcgtgtcat actccttgtg taccgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga catgcaaact ctgaccccag   2040
ttgggaggtt gataaccgct aaccccgtaa tcactgaaag cactgagaac tctaagatga   2100
tgctggaact tgatccacca tttggggact cttacattgt cataggagtc ggggagaaga   2160
agatcaccca ccactggcac aggagtggca gcaccattgg aaaagcattt gaagccactg   2220
tgagaggtgc caagagaatg gcagtcttgg gagacacagc ctgggacttt ggatcagttg   2280
gaggcgctct caactcattg ggcaagggca tccatcaaat ttttggagca gctttcaaat   2340
cattgtttgg aggaatgtcc tggttctcac aaattctcat tggaacgttg ctgatgtggt   2400
tgggtctgaa cacaaagaat ggatctattt cccttatgtg cttggcctta gggggagtgt   2460
tgatcttctt atccacagcc gtctctgctg atgtggggtg ctcggtggac ttctcaaaga   2520
aggagacgag atgcggtaca ggggtgttcg tctataacga cgttgaagcc tggagggaca   2580
ggtacaagta ccatcctgac tccccccgta gattggcagc agcagtcaag caagcctggg   2640
aagatggtat ctgtgggatc tcctctgttt caagaatgga aaacatcatg tggagatcag   2700
tagaagggga gctcaacgca atcctggaag agaatggagt tcaactgacg gtcgttgtgg   2760
gatctgtaaa aaaccccatg tggagaggtc cacagagatt gcccgtgcct gtgaacgagc   2820
tgccccacgg ctggaaggct tgggggaaat cgtacttcgt cagagcagca aagacaaata   2880
acagctttgt cgtggatggt gacacactga aggaatgccc actcaaacat agagcatgga   2940
acagctttct tgtggaggat catgggttcg ggtatttca cactagtgtc tggctcaagg   3000
ttagagaaga ttattcatta gagtgtgatc cagccgttat tggaacagct gttaagggaa   3060
aggaggctgt acacagtgat ctaggctact ggattgagag tgagaagaat gacacatgga   3120
ggctgaagag ggcccatctg atcgagatga aaacatgtga atggccaaag tcccacacat   3180
tgtggacaga tggaatagaa gagagtgatc tgatcatacc caagtcttta gctgggccac   3240
tcagccatca caataccaga gagggctaca ggacccaaat gaaagggcca tggcacagtg   3300
aagagcttga aattcggttt gaggaatgcc caggcactaa ggtccacgtg gaggaaacat   3360
gtggaacaag aggaccatct ctgagatcaa ccactgcaag cggaagggtg atcgaggaat   3420
ggtgctgcag ggagtgcaca atgcccccac tgtcgttccg ggctaaagat ggctgttggt   3480
atggaatgga gataaggccc aggaaagaac cagaaagtaa cttagtaagg tcaatggtga   3540
```

-continued

```
ctgcaggatc aactgatcac atggatcact tctcccttgg agtgcttgtg attctgctca   3600
tggtgcagga agggctgaag aagagaatga ccacaaagat catcataagc acatcaatgg   3660
cagtgctggt agctatgatc ctgggaggat tttcaatgag tgacctggct aagcttgcaa   3720
ttttgatggg tgccaccttc gcggaaatga acactggagg agatgtagct catctggcgc   3780
tgatagcggc attcaaagtc agaccagcgt tgctggtatc tttcatcttc agagctaatt   3840
ggacaccccg tgaaagcatg ctgctggcct tggcctcgtg tcttttgcaa actgcgatct   3900
ccgccttgga aggcgacctg atggttctca tcaatggttt tgctttggcc tggttggcaa   3960
tacgagcgat ggttgttcca cgcactgata acatcacctt ggcaatcctg gctgctctga   4020
caccactggc ccggggcaca ctgcttgtgg cgtggagagc aggccttgct acttgcgggg   4080
ggtttatgct cctctctctg aagggaaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc cccctagcga agtactcaca gctgttggcc   4260
tgatatgcgc attggctgga gggttcgcca aggcagatat agagatggct gggcccatgg   4320
ccgcggtcgg tctgctaatt gtcagttacg tggtctcagg aaagagtgtg gacatgtaca   4380
ttgaaagagc aggtgacatc acatgggaaa aagatgcgga agtcactgga aacagtcccc   4440
ggctcgatgt ggcgctagat gagagtggtg atttctccct ggtggaggat gacggtcccc   4500
ccatgagaga gatcatactc aaggtggtcc tgatgaccat ctgtggcatg aacccaatag   4560
ccataccctt tgcagctgga gcgtggtacg tatacgtgaa gactggaaaa aggagtggtg   4620
ctctatggga tgtgcctgct cccaaggaag taaaaaaggg ggagaccaca gatggagtgt   4680
acagagtaat gactcgtaga ctgctaggtt caacacaagt tggagtggga gttatgcaag   4740
agggggtctt tcacactatg tggcacgtca caaaaggatc cgcgctgaga agcggtgaag   4800
ggagacttga tccatactgg ggagatgtca agcaggatct ggtgtcatac tgtggtccat   4860
ggaagctaga tgccgcctgg gacgggcaca gcgaggtgca gctcttggcc gtgccccccg   4920
gagagagagc gaggaacatc cagactctgc ccggaatatt taagacaaag gatggggaca   4980
ttggagcggt tgcgctggat tacccagcag gaacttcagg atctccaatc ctagacaagt   5040
gtgggagagt gataggactt tatggcaatg gggtcgtgat caaaaatggg agttatgtta   5100
gtgccatcac ccaagggagg agggaggaag agactcctgt tgagtgcttc gagccttcga   5160
tgctgaagaa gaagcagcta actgtcttag acttgcatcc tggagctggg aaaaccagga   5220
gagttcttcc tgaaatagtc cgtgaagcca taaaaacaag actccgtact gtgatcttag   5280
ctccaaccag ggttgtcgct gctgaaatgg aggaagccct tagagggctt ccagtgcgtt   5340
atatgacaac agcagtcaat gtcacccact ctggaacaga aatcgtcgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcggctgcca tcttcatgac cgccacgcca ccaggaaccc   5580
gtgacgcatt tccggactcc aactcaccaa ttatggacac cgaagtggaa gtcccagaga   5640
gagcctggag ctcaggcttt gattgggtga cggatcattc tggaaaaaca gtttggtttg   5700
ttccaagcgt gaggaacggc aatgagatcg cagcttgtct gacaaaggct ggaaaacggg   5760
tcatacagct cagcagaaag acttttgaga cagagttcca gaaaacaaaa catcaagagt   5820
gggactttgt cgtgacaact gacatttcag agatgggcgc caactttaaa gctgaccgtg   5880
tcatagattc caggagatgc ctaaagccgg tcatacttga tggcgagaga gtcattctgg   5940
```

-continued ctggacccat gcctgtcaca catgccagcg ctgcccagag gagggggcgc ataggcagga 6000
atcccaacaa acctggagat gagtatctgt atggaggtgg gtgcgcagag actgacgaag 6060
accatgcaca ctggcttgaa gcaagaatgc tccttgacaa tatttacctc caagatggcc 6120
tcatagcctc gctctatcga cctgaggccg acaaagtagc agccattgag ggagagttca 6180
agcttaggac ggagcaaagg aagacctttg tggaactcat gaaaagagga gatcttcctg 6240
tttggctggc ctatcaggtt gcatctgccg gaataaccta cacagataga agatggtgct 6300
ttgatggcac gaccaacaac accataatgg aagacagtgt gccggcagag gtgtggacca 6360
gacacggaga gaaaagagtg ctcaaaccga ggtggatgga cgccagagtt tgttcagatc 6420
atgcggccct gaagtcattc aaggagtttg ccgctgggaa aagaggagcg gcttttggag 6480
tgatggaagc cctgggaaca ctgccaggac acatgacaga gagattccag gaagccattg 6540
acaacctcgc tgtgctcatg cgggcagaga ctggaagcag gccttacaaa gccgcggcgg 6600
cccaattgcc ggagaccct a gagaccatta tgcttttggg gttgctggga acagtctcgc 6660
tgggaatctt tttcgtcttg atgaggaaca agggcatagg gaagatgggc tttggaatgg 6720
tgactcttgg ggccagcgca tggctcatgt ggctctcgga aattgagcca gccagaattg 6780
catgtgtcct cattgttgtg ttcctattgc tggtggtgct catacctgag ccagaaaagc 6840
aaagatctcc ccaggacaac caaatggcaa tcatcatcat ggtagcagta ggtcttctgg 6900
gcttgattac cgccaatgaa ctcggatggt tggagagaac aaagagtgac ctaagccatc 6960
taatgggaag gagagaggag gggcaacca taggattctc aatggacatt gacctgcggc 7020
cagcctcagc ttgggccatc tatgctgcct tgacaacttt cattacccca gccgtccaac 7080
atgcagtgac cacttcatac aacaactact ccttaatggc gatggccacg caagctggag 7140
tgttgtttgg tatgggcaaa gggatgccat tctacgcatg ggactttgga gtcccgctgc 7200
taatgatagg ttgctactca caattaacac ccctgaccct aatagtggcc atcattttgc 7260
tcgtggcgca ctacatgtac ttgatcccag ggctgcaggc agcagctgcg cgtgctgccc 7320
agaagagaac ggcagctggc atcatgaaga accctgttgt ggatggaata gtggtgactg 7380
acattgacac aatgacaatt gacccccaag tggagaaaaa gatgggacag gtgctactca 7440
tagcagtagc cgtctccagc gccatactgt cgcggaccgc ctgggggtgg ggggaggctg 7500
gggccctgat cacagctgca acttccactt tgtgggaagg ctctccgaac aagtactgga 7560
actcctctac agccacttca ctgtgtaaca tttttagggg aagttacttg gctggagctt 7620
ctctaatcta cacagtaaca agaaacgctg gcttggtcaa gagacgtggg ggtggaacag 7680
gagagaccct gggagagaaa tggaaggccc gcttgaacca gatgtcggcc ctggagttct 7740
actcctacaa aaagtcaggc atcaccgagg tgtgcagaga agaggcccgc cgcgccctca 7800
aggacggtgt ggcaacggga ggccatgctg tgtcccgagg aagtgcaaag ctgagatggt 7860
tggtggagcg gggatacctg cagccctatg gaaaggtcat tgatcttgga tgtggcagag 7920
gggctggag ttactacgcc gccaccatcc gcaaagttca agaagtgaaa ggatacacaa 7980
aaggaggccc tggtcatgaa gaacccatgt tggtgcaaag ctatgggtgg aacatagtcc 8040
gtcttaagag tggggtggac gtctttcata tggcggctga gccgtgtgac acgttgctgt 8100
gtgacatagg tgagtcatca tctagtcctg aagtggaaga agcacggacg ctcagagtcc 8160
tctccatggt gggggattgg cttgaaaaaa gaccaggagc cttttgtata aaagtgttgt 8220
gcccatacac cagcactatg atggaaaccc tggagcgact gcagcgtagg tatgggggag 8280

-continued

```
gactggtcag agtgccactc tcccgcaact ctacacatga gatgtactgg gtctctggag   8340
cgaaaagcaa caccataaaa agtgtgtcca ccacgagcca gctcctcttg gggcgcatgg   8400
acgggcccag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagaccccca agaaggcact cgtcaggtta tgagcatggt ctcttcctgg ttgtggaaag   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagttgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttgaacg aggatcactg gatggggaga gagaactcag   9180
gaggtggtgt tgaagggctg ggattacaaa gactcggata tgtcctagaa gagatgagtc   9240
gcataccagg aggaaggatg tatgcagatg acactgctgg ctgggacacc cgcatcagca   9300
ggtttgatct ggagaatgaa gctctaatca ccaaccaaat ggagaaaggg cacagggcct   9360
tggcattggc cataatcaag tacacatacc aaaacaaagt ggtaaaggtc cttagaccag   9420
ctgaaaaagg gaagacagtt atggacatta tttcgagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa acgaatggca gtcagtggag   9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
gggaagaagt tccgttttgc tcccaccact tcaacaagct ccatctcaag gacgggaggt   9840
ccattgtggt tccctgccgc caccaagatg aactgattgg ccgggcccgc gtctctccag   9900
gggcgggatg gagcatccgg gagactgctt gcctagcaaa atcatatgcg caaatgtggc   9960
agctccttta tttccacaga agggacctcc gactgatggc caatgccatt tgttcatctg  10020
tgccagttga ctgggttcca actgggagaa ctacctggtc aatccatgga aagggagaat  10080
ggatgaccac tgaagacatg cttgtggtgt ggaacagagt gtggattgag gagaacgacc  10140
acatggaaga caagacccca gttacgaaat ggacagacat tccctatttg ggaaaaaggg  10200
aagacttgtg gtgtggatct ctcatagggc acagaccgcg caccacctgg gctgagaaca  10260
ttaaaaacac agtcaacatg gtgcgcagga tcataggtga tgaagaaaag tacatggact  10320
acctatccac ccaagttcgc tacttgggtg aagaagggtc tacacctgga gtgctgtaag  10380
caccaatctt agtgttgtca ggcctgctag tcagccacag cttggggaaa gctgtgcagc  10440
ctgtgacccc cccaggagaa gctgggaaac caagcctata gtcaggccga gaacgccatg  10500
gcacggaaga agccatgctg cctgtgagcc cctcagagga cactgagtca aaaaacccca  10560
cgcgcttgga ggcgcaggat gggaaaagaa ggtggcgacc ttccccaccc ttcaatctgg  10620
ggcctgaact ggagatcagc tgtggatctc cagaagaggg actagtggtt agaggagacc  10680
```

ccccggaaaa cgcaaaacag catattgacg ctgggaaaga ccagagactc catgagtttc 10740
caccacgctg gccgccaggc acagatcgcc gaatagcggc ggccggtgtg gggaaatcca 10800
tgggtct 10807

<210> SEQ ID NO 41
<211> LENGTH: 10807
<212> TYPE: DNA
<213> ORGANISM: Flavivirus FSME

<400> SEQUENCE: 41
agttgttgat ctgtgtgaat cagactgcga cagttcgagt ttgaagcgaa agctagcaac 60
agtatcaaca ggttttattt tggatttgga aacgagagtt tctggtcatg aaaaacccaa 120
aaaagaaatc cggaggattc cggattgtca atatgctaaa acgcggagta gcccgtgtga 180 gccccttttgg gggcttgaag aggctgccag ccggacttct gctgggtcat gggcccatca 240
ggatggtctt ggcgattcta gcctttttga gattcacggc aatcaagcca tcactgggtc 300
tcatcaatag atggggttca gtggggaaaa aagaggctat ggaaataata aagaagttca 360
agaaagatct ggctgccatg ctgagaataa tcaatgctag gaaggagaag aagagacgag 420
gcgcagatac tagtgtcgga attgttggcc tcctgctgac cacagctatg gcagcggagg 480
tcactagacg tgggagtgca tactatatgt acttggacag aaacgatgct ggggaggcca 540
tatcttttcc aaccacattg ggatgaata agtgttatat acagatcatg gatcttggac 600
acatgtgtga tgccaccatg agctatgaat gccctatgct ggatgagggg gtggaaccag 660
atgacgtcga ttgttggtgc aacacgacgt caacttgggt tgtgtacgga acctgccatc 720
acaaaaaagg tgaagcacgg agatctagaa gagctgtgac gctcccctcc cattccacta 780
gaaagctgca aacgcggtcg caaacctggt tggaatcaag agaatacaca aagcacttga 840
ttagagtcga aaattggata ttcaggaacc ctggcttcgc gttagcagca gctgccatcg 900
cttggctttt gggaagctca acgagccaaa aagtcatata cttggtcatg atactgctga 960
ttgccccggc atacagcatc aggtgcatag gagtcagcaa tagggacttt gtggaaggta 1020
tgtcaggtgg gacttgggtt gatgttgtct tggaacatgg aggttgtgtc accgtaatgg 1080
cacaggacaa accgactgtc gacatagagc tggttacaac aacagtcagc aacatggcgg 1140
aggtaagatc ctactgctat gaggcatcaa tatcagacat ggcttcggac agccgctgcc 1200
caacacaagg tgaagcctac cttgacaagc aatcagacac tcaatatgtc tgcaaaagaa 1260
cgttagtgga cagaggctgg ggaaatggat gtggactttt tggcaaaggg agcctggtga 1320
catgcgctaa gtttgcatgc tccaagaaaa tgaccgggaa gagcatccag ccagagaatc 1380
tggagtaccg gataatgctg tcagttcatg gctcccagca cagtgggatg atcgttaatg 1440
acacaggaca tgaaactgat gagaatagag cgaaggttga gataacgccc aattcaccaa 1500
gagccgaagc caccctgggg ggttttggaa gcctaggact tgattgtgaa ccgaggacag 1560
gccttgactt ttcagatttg tattacttga ctatgaataa caagcactgg ttggttcaca 1620
aggagtggtt ccacgacatt ccattacctt ggcacgctgg ggcagacacc ggaactccac 1680
actggaacaa caaagaagca ctggtagagt tcaaggacgc acatgccaaa aggcaaactg 1740
tcgtggttct agggagtcaa gaaggagcag ttcacacggc ccttgctgga gctctggagg 1800
ctgagatgga tggtgcaaag ggaaggctgt cctctggcca cttgaaatgt cgcctgaaaa 1860
tggataaact tagattgaag ggcgtgtcat actccttgtg taccgcagcg ttcacattca 1920

-continued

```
ccaagatccc ggctgaaaca ctgcacggga cagtcacagt ggaggtacag tacgcaggga   1980
cagatggacc ttgcaaggtt ccagctcaga tggcggtgga catgcaaact ctgaccccag   2040
ttgggaggtt gataaccgct aaccccgtaa tcactgaaag cactgagaac tctaagatga   2100
tgctggaact tgatccacca tttggggact cttacattgt cataggagtc ggggagaaga   2160
agatcaccca ccactggcac aggagtggca gcaccattgg aaaagcattt gaagccactg   2220
tgagaggtgc caagagaatg gcagtcttgg gagacacagc ctgggacttt ggatcagttg   2280
gaggcgctct caactcattg ggcaagggca tccatcaaat tttggagca gctttcaaat    2340
cattgtttgg aggaatgtcc tggttctcac aaattctcat tggaacgttg ctgatgtggt   2400
tgggtctgaa cacaaagaat ggatctattt cccttatgtg cttggcctta gggggagtgt   2460
tgatcttctt atccacagcc gtctctgctg atgtggggtg ctcggtggac ttctcaaaga   2520
aggagacgag atgcggtaca ggggtgttcg tctataacga cgttgaagcc tggagggaca   2580
ggtacaagta ccatcctgac tccccccgta gattggcagc agcagtcaag caagcctggg   2640
aagatggtat ctgtgggatc tcctctgttt caagaatgga aaacatcatg tggagatcag   2700
tagaagggga gctcaacgca atcctggaag agaatggagt tcaactgacg gtcgttgtgg   2760
gatctgtaaa aaaccccatg tggagaggtc cacagagatt gcccgtgcct gtgaacgagc   2820
tgccccacgg ctggaaggct tgggggaaat cgtacttcgt cagagcagca aagacaaata   2880
acagctttgt cgtggatggt gacacactga aggtatgccc actcaaacat agagcatgga   2940
acagctttct tgtggaggat catgggttcg ggtatttca cactagtgtc tggctcaagg    3000
ttagagaaga ttattcatta gagtgtgatc cagccgttat tggaacagct gttaagggaa   3060
aggaggctgt acacagtgat ctaggctact ggattgagag tgagaagaat gacacatgga   3120
ggctgaagag ggcccatctg atcgagatga aaacatgtga atggccaaag tcccacacat   3180
tgtggacaga tggaatagaa gagagtgatc tgatcatacc caagtcttta gctgggccac   3240
tcagccatca caataccaga gagggctaca ggacccaaat gaaagggcca tggcacagtg   3300
aagagcttga aattcggttt gaggaatgcc caggcactaa ggtccacgtg gaggaaacat   3360
gtggaacaag aggaccatct ctgagatcaa ccactgcaag cggaagggtg atcgaggaat   3420
ggtgctgcag ggagtgcaca atgcccccac tgtcgttccg ggctaaagat ggctgttggt   3480
atggaatgga gataaggccc aggaaagaac cagaaagtaa cttagtaagg tcaatggtga   3540
ctgcaggatc aactgatcac atggatcact tctcccttgg agtgcttgtg attctgctca   3600
tggtgcagga agggctgaag aagagaatga ccacaaagat catcataagc acatcaatgg   3660
cagtgctggt agctatgatc ctgggaggat tttcaatgag tgacctggct aagcttgcaa   3720
ttttgatggg tgccaccttc gcggaaatga acactggagg agatgtagct catctggcgc   3780
tgatagcggc attcaaagtc agaccagcgt tgctggtatc tttcatcttc agagctaatt   3840
ggacaccccg tgaaagcatg ctgctggcct tggcctcgtg tcttttgcaa actgcgatct   3900
ccgccttgga aggcgacctg atggttctca tcaatggttt tgctttggcc tggttggcaa   3960
tacgagcgat ggttgttcca cgcactgata acatcacctt ggcaatcctg gctgctctga   4020
caccactggc ccggggcaca ctgcttgtgg cgtggagagc aggccttgct acttgcgggg   4080
ggtttatgct cctctctctg aagggaaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc cccctagcga agtactcaca gctgttggcc   4260
tgatatgcgc attggctgga gggttcgcca aggcagatat agagatggct gggcccatgg   4320
```

```
ccgcggtcgg tctgctaatt gtcagttacg tggtctcagg aaagagtgtg gacatgtaca   4380
ttgaaagagc aggtgacatc acatgggaaa aagatgcgga agtcactgga aacagtcccc   4440
ggctcgatgt ggcgctagat gagagtggtg atttctccct ggtggaggat gacggtcccc   4500
ccatgagaga gatcatactc aaggtggtcc tgatgaccat ctgtggcatg aacccaatag   4560
ccataccctt tgcagctgga gcgtggtacg tatacgtgaa gactggaaaa aggagtggtg   4620
ctctatggga tgtgcctgct cccaaggaag taaaaaaggg ggagaccaca gatggagtgt   4680
acagagtaat gactcgtaga ctgctaggtt caacacaagt tggagtggga gttatgcaag   4740
agggggtctt tcacactatg tggcacgtca caaaaggatc cgcgctgaga agcggtgaag   4800
ggagacttga tccatactgg ggagatgtca agcaggatct ggtgtcatac tgtggtccat   4860
ggaagctaga tgccgcctgg gacgggcaca gcgaggtgca gctcttggcc gtgccccccg   4920
gagagagagc gaggaacatc cagactctgc ccggaatatt taagacaaag gatggggaca   4980
ttggagcggt tgcgctggat tacccagcag gaacttcagg atctccaatc ctagacaagt   5040
gtgggagagt gataggactt tatggcaatg ggtcgtgat caaaaatggg agttatgtta   5100
gtgccatcac ccaagggagg agggaggaag agactcctgt tgagtgcttc gagccttcga   5160
tgctgaagaa gaagcagcta actgtcttag acttgcatcc tggagctggg aaaaccagga   5220
gagttcttcc tgaaatagtc cgtgaagcca taaaaacaag actccgtact gtgatcttag   5280
ctccaaccag ggttgtcgct gctgaaatgg aggaagccct tagagggctt ccagtgcgtt   5340
atatgacaac agcagtcaat gtcacccact ctggaacaga aatcgtcgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcggctgcca tcttcatgac cgccacgcca ccaggaaccc   5580
gtgacgcatt tccggactcc aactcaccaa ttatggacac cgaagtggaa gtcccagaga   5640
gagcctggag ctcaggcttt gattgggtga cggatcattc tggaaaaaca gtttggtttg   5700
ttccaagcgt gaggaacggc aatgagatcg cagcttgtct gacaaaggct ggaaaacggg   5760
tcatacagct cagcagaaag acttttgaga cagagttcca gaaaacaaaa catcaagagt   5820
gggactttgt cgtgacaact gacatttcag agatgggcgc caactttaaa gctgaccgtg   5880
tcatagattc caggagatgc ctaaagccgg tcatacttga tggcgagaga gtcattctgg   5940
ctggacccat gcctgtcaca catgccagcg ctgcccagag gagggggcgc ataggcagga   6000
atcccaacaa acctggagat gagtatctgt atggaggtgg gtgcgcagag actgacgaag   6060
accatgcaca ctggcttgaa gcaagaatgc tccttgacaa tatttacctc caagatggcc   6120
tcatagcctc gctctatcga cctgaggccg acaaagtagc agccattgag ggagagttca   6180
agcttaggac ggagcaaagg aagacctttg tggaactcat gaaaagagga gatcttcctg   6240
tttggctggc ctatcaggtt gcatctgccg gaataaccta cacagataga agatggtgct   6300
ttgatggcac gaccaacaac accataatgg aagacagtgt gccggcagag gtgtggacca   6360
gacacggaga gaaaagagtg ctcaaaccga ggtggatgga cgccagagtt tgttcagatc   6420
atgcggccct gaagtcattc aaggagtttg ccgctgggaa aagaggagcg gcttttggag   6480
tgatggaagc cctgggaaca ctgccaggac acatgacaga gagattccag gaagccattg   6540
acaacctcgc tgtgctcatg cgggcagaga ctggaagcag gccttacaaa gccgcggcgg   6600
cccaattgcc ggagacccta gagaccatta tgcttttggg gttgctggga acagtctcgc   6660
```

-continued

```
tgggaatctt tttcgtcttg atgaggaaca agggcatagg gaagatgggc tttggaatgg   6720
tgactcttgg ggccagcgca tggctcatgt ggctctcgga aattgagcca gccagaattg   6780
catgtgtcct cattgttgtg ttcctattgc tggtggtgct catacctgag ccagaaaagc   6840
aaagatctcc ccaggacaac caaatggcaa tcatcatcat ggtagcagta ggtcttctgg   6900
gcttgattac cgccaatgaa ctcggatggt tggagagaac aaagagtgac ctaagccatc   6960
taatgggaag gagagaggag gggcaacca taggattctc aatggacatt gacctgcggc   7020
cagcctcagc ttgggccatc tatgctgcct tgacaacttt cattacccca gccgtccaac   7080
atgcagtgac cacttcatac aacaactact ccttaatggc gatggccacg caagctggag   7140
tgttgtttgg tatgggcaaa gggatgccat tctacgcatg ggactttgga gtcccgctgc   7200
taatgatagg ttgctactca caattaacac ccctgaccct aatagtggcc atcattttgc   7260
tcgtggcgca ctacatgtac ttgatcccag ggctgcaggc agcagctgcg cgtgctgccc   7320
agaagagaac ggcagctggc atcatgaaga accctgttgt ggatggaata gtggtgactg   7380
acattgacac aatgacaatt gacccccaag tggagaaaaa gatgggacag gtgctactca   7440
tagcagtagc cgtctccagc gccatactgt cgcggaccgc ctgggggtgg ggggaggctg   7500
gggccctgat cacagctgca acttccactt tgtgggaagg ctctccgaac aagtactgga   7560
actcctctac agccacttca ctgtgtaaca tttttagggg aagttacttg gctggagctt   7620
ctctaatcta cacagtaaca agaaacgctg gcttggtcaa gagacgtggg ggtggaacag   7680
gagagaccct gggagagaaa tggaaggccc gcttgaacca gatgtcggcc ctggagttct   7740
actcctacaa aaagtcaggc atcaccgagg tgtgcagaga agaggcccgc cgcgccctca   7800
aggacggtgt ggcaacggga ggccatgctg tgtcccgagg aagtgcaaag ctgagatggt   7860
tggtggagcg gggatacctg cagccctatg gaaaggtcat tgatcttgga tgtggcagag   7920
ggggctggag ttactacgcc gccaccatcc gcaaagttca agaagtgaaa ggatacacaa   7980
aaggaggccc tggtcatgaa gaacccatgt tggtgcaaag ctatgggtgg aacatagtcc   8040
gtcttaagag tggggtggac gtctttcata tggcggctga gccgtgtgac acgttgctgt   8100
gtgacatagg tgagtcatca tctagtcctg aagtggaaga agcacggacg ctcagagtcc   8160
tctccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag agtgccactc tcccgcaact ctacacatga gatgtactgg gtctctggag   8340
cgaaaagcaa caccataaaa agtgtgtcca ccacgagcca gctcctcttg ggcgcatgg    8400
acgggcccag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagaccccca agaaggcact cgtcaggtta tgagcatggt ctcttcctgg ttgtggaaag   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagttgt gtgtacaaca tgatgggaaa aagagaaaag aaacaagggg   9060
```

-continued aatttggaaa ggccaagggc agccgcgcca tctggtatat gtggctaggg gctagatttc 9120
tagagttcga agcccttgga ttcttgaacg aggatcactg gatggggaga gagaactcag 9180
gaggtggtgt tgaagggctg ggattacaaa gactcggata tgtcctagaa gagatgagtc 9240
gcataccagg aggaaggatg tatgcagatg acactgctgg ctgggacacc cgcatcagca 9300
ggtttgatct ggagaatgaa gctctaatca ccaaccaaat ggagaaaggg cacagggcct 9360
tggcattggc cataatcaag tacacatacc aaaacaaagt ggtaaaggtc cttagaccag 9420
ctgaaaaagg gaagacagtt atggacatta tttcgagaca agaccaaagg gggagcggac 9480
aagttgtcac ttacgctctt aacacattta ccaacctagt ggtgcaactc attcggaata 9540
tggaggctga ggaagttcta gagatgcaag acttgtggct gctgcggagg tcagagaaag 9600
tgaccaactg gttgcagagc aacggatggg ataggctcaa acgaatggca gtcagtggag 9660
atgattgcgt tgtgaagcca attgatgata ggtttgcaca tgccctcagg ttcttgaatg 9720
atatgggaaa agttaggaag gacacacaag agtggaaacc ctcaactgga tgggacaact 9780
gggaagaagt tccgttttgc tcccaccact tcaacaagct ccatctcaag gacgggaggt 9840
ccattgtggt tccctgccgc caccaagatg aactgattgg ccgggcccgc gtctctccag 9900
gggcgggatg gagcatccgg gagactgctt gcctagcaaa atcatatgcg caaatgtggc 9960
agctccttta tttccacaga agggacctcc gactgatggc caatgccatt tgttcatctg 10020
tgccagttga ctgggttcca actgggagaa ctacctggtc aatccatgga aagggagaat 10080
ggatgaccac tgaagacatg cttgtggtgt ggaacagagt gtggattgag gagaacgacc 10140
acatggaaga caagacccca gttacgaaat ggacagacat tccctatttg ggaaaaaggg 10200
aagacttgtg gtgtggatct ctcatagggc acagaccgcg caccacctgg gctgagaaca 10260
ttaaaaacac agtcaacatg gtgcgcagga tcataggtga tgaagaaaag tacatggact 10320
acctatccac ccaagttcgc tacttgggtg aagaagggtc tacacctgga gtgctgtaag 10380
caccaatctt agtgttgtca ggcctgctag tcagccacag cttggggaaa gctgtgcagc 10440
ctgtgacccc cccaggagaa gctgggaaac caagcctata gtcaggccga gaacgccatg 10500
gcacggaaga agccatgctg cctgtgagcc cctcagagga cactgagtca aaaaacccca 10560
cgcgcttgga ggcgcaggat gggaaaagaa ggtggcgacc ttccccaccc ttcaatctgg 10620
ggcctgaact ggagatcagc tgtggatctc cagaagaggg actagtggtt agaggagacc 10680
ccccggaaaa cgcaaaacag catattgacg ctgggaaaga ccagagactc catgagtttc 10740
caccacgctg gccgccaggc acagatcgcc gaatagcggc ggccggtgtg gggaaatcca 10800
tgggtct 10807

<210> SEQ ID NO 42
<211> LENGTH: 10807
<212> TYPE: DNA
<213> ORGANISM: Flavivirus FSME

<400> SEQUENCE: 42
agttgttgat ctgtgtgaat cagactgcga cagttcgagt ttgaagcgaa agctagcaac 60
agtatcaaca ggttttattt tggatttgga aacgagagtt tctggtcatg aaaaacccaa 120
aaaagaaatc cggaggattc cggattgtca atatgctaaa acgcggagta gcccgtgtga 180
gcccctttgg gggcttgaag aggctgccag ccggacttct gctgggtcat gggcccatca 240
ggatggtctt ggcgattcta gcctttttga gattcacggc aatcaagcca tcactgggtc 300

-continued

```
tcatcaatag atggggttca gtggggaaaa aagaggctat ggaaataata aagaagttca    360
agaaagatct ggctgccatg ctgagaataa tcaatgctag gaaggagaag aagagacgag    420
gcgcagatac tagtgtcgga attgttggcc tcctgctgac cacagctatg gcagcggagg    480
tcactagacg tgggagtgca tactatatgt acttggacag aaacgatgct ggggaggcca    540
tatcttttcc aaccacattg gggatgaata agtgttatat acagatcatg gatcttggac    600
acatgtgtga tgccaccatg agctatgaat gccctatgct ggatgagggg gtggaaccag    660
atgacgtcga ttgttggtgc aacacgacgt caacttgggt tgtgtacgga acctgccatc    720
acaaaaaagg tgaagcacgg agatctagaa gagctgtgac gctcccctcc cattccacta    780
gaaagctgca aacgcggtcg caaacctggt tggaatcaag agaatacaca aagcacttga    840
ttagagtcga aaattggata ttcaggaacc ctggcttcgc gttagcagca gctgccatcg    900
cttggctttt gggaagctca acgagccaaa aagtcatata cttggtcgtg atactgctga    960
ttgccccggc atacagcatc aggtgcatag gagtcagcaa tagggacttt gtggaaggta   1020
tgtcaggtgg gacttgggtt gatgttgtct tggaacatgg aggttgtgtc accgtaatgg   1080
cacaggacaa accgactgtc gacatagagc tggttacaac aacagtcagc aacatggcgg   1140
aggtaagatc ctactgctat gaggcatcaa tatcagacat ggcttcggac agccgctgcc   1200
caacacaagg tgaagcctac cttgacaagc aatcagacac tcaatatgtc tgcaaaagaa   1260
cgttagtgga cagaggctgg ggaaatggat gtggactttt tggcaaaggg agcctggtga   1320
catgcgctaa gtttgcatgc tccaagaaaa tgaccgggaa gagcatccag ccagagaatc   1380
tggagtaccg gataatgctg tcagttcatg gctcccagca cagtgggatg atcgttaatg   1440
acacaggaca tgaaactgat gagaatagag cgaaggttga gataacgccc aattcaccaa   1500
gagccgaagc caccctgggg ggttttggaa gcctaggact tgattgtgaa ccgaggacag   1560
gccttgactt ttcagatttg tattacttga ctatgaataa caagcactgg ttggttcaca   1620
aggagtggtt ccacgacatt ccattacctt ggcacgctgg ggcagacacc ggaactccac   1680
actggaacaa caaagaagca ctggtagagt tcaaggacgc acatgccaaa aggcaaactg   1740
tcgtggttct agggagtcaa gaaggagcag ttcacacggc ccttgctgga gctctggagg   1800
ctgagatgga tggtgcaaag ggaaggctgt cctctggcca cttgaaatgt cgcctgaaaa   1860
tggataaact tagattgaag ggcgtgtcat actccttgtg taccgcagcg ttcacattca   1920
ccaagatccc ggctgaaaca ctgcacggga cagtcacagt ggaggtacag tacgcaggga   1980
cagatggacc ttgcaaggtt ccagctcaga tggcggtgga catgcaaact ctgaccccag   2040
ttgggaggtt gataaccgct aaccccgtaa tcactgaaag cactgagaac tctaagatga   2100
tgctggaact tgatccacca tttggggact cttacattgt cataggagtc ggggagaaga   2160
agatcaccca ccactggcac aggagtggca gcaccattgg aaaagcattt gaagccactg   2220
tgagaggtgc caagagaatg gcagtcttgg gagacacagc ctgggacttt ggatcagttg   2280
gaggcgctct caactcattg ggcaagggca tccatcaaat ttttggagca gctttcaaat   2340
cattgtttgg aggaatgtcc tggttctcac aaattctcat tggaacgttg ctgatgtggt   2400
tgggtctgaa cacaaagaat ggatctattt cccttatgtg cttggcctta gggggagtgt   2460
tgatcttctt atccacagcc gtctctgctg atgtggggtg ctcggtggac ttctcaaaga   2520
aggagacgag atgcggtaca ggggtgttcg tctataacga cgttgaagcc tggagggaca   2580
ggtacaagta ccatcctgac tccccccgta gattggcagc agcagtcaag caagcctggg   2640
aagatggtat ctgtgggatc tcctctgttt caagaatgga aaacatcatg tggagatcag   2700
```

```
tagaaggggga gctcaacgca atcctggaag agaatggagt tcaactgacg gtcgttgtgg   2760
gatctgtaaa aaaccccatg tggagaggtc cacagagatt gcccgtgcct gtgaacgagc   2820
tgccccacgg ctggaaggct tgggggaaat cgtacttcgt cagagcagca aagacaaata   2880
acagctttgt cgtggatggt gacacactga aggtatgccc actcaaacat agagcatgga   2940
acagctttct tgtggaggat catgggttcg ggtatttca cactagtgtc tggctcaagg   3000
ttagagaaga ttattcatta gagtgtgatc cagccgttat tggaacagct gttaagggaa   3060
aggaggctgt acacagtgat ctaggctact ggattgagag tgagaagaat gacacatgga   3120
ggctgaagag ggcccatctg atcgagatga aaacatgtga atggccaaag tcccacacat   3180
tgtggacaga tggaatagaa gagagtgatc tgatcatacc caagtcttta gctgggccac   3240
tcagccatca caataccaga gagggctaca ggacccaaat gaaagggcca tggcacagtg   3300
aagagcttga aattcggttt gaggaatgcc caggcactaa ggtccacgtg gaggaaacat   3360
gtggaacaag aggaccatct ctgagatcaa ccactgcaag cggaagggtg atcgaggaat   3420
ggtgctgcag ggagtgcaca atgcccccac tgtcgttccg ggctaaagat ggctgttggt   3480
atggaatgga gataaggccc aggaaagaac cagaaagtaa cttagtaagg tcaatggtga   3540
ctgcaggatc aactgatcac atggatcact tctcccttgg agtgcttgtg attctgctca   3600
tggtgcagga agggctgaag aagagaatga ccacaaagat catcataagc acatcaatgg   3660
cagtgctggt agctatgatc ctgggaggat tttcaatgag tgacctggct aagcttgcaa   3720
ttttgatggg tgccaccttc gcggaaatga acactggagg agatgtagct catctggcgc   3780
tgatagcggc attcaaagtc agaccagcgt tgctggtatc tttcatcttc agagctaatt   3840
ggacaccccg tgaaagcatg ctgctggcct tggcctcgtg tcttttgcaa actgcgatct   3900
ccgccttgga aggcgacctg atggttctca tcaatggttt tgctttggcc tggttggcaa   3960
tacgagcgat ggttgttcca cgcactgata acatcacctt ggcaatcctg gctgctctga   4020
caccactggc ccggggcaca ctgcttgtgg cgtggagagc aggccttgct acttgcgggg   4080
ggtttatgct cctctctctg aagggaaaag gcagtgtgaa gaagaactta ccatttgtca   4140
tggccctggg actaaccgct gtgaggctgg tcgaccccat caacgtggtg ggactgctgt   4200
tgctcacaag gagtgggaag cggagctggc cccctagcga agtactcaca gctgttggcc   4260
tgatatgcgc attggctgga gggttcgcca aggcagatat agagatggct gggcccatgg   4320
ccgcggtcgg tctgctaatt gtcagttacg tggtctcagg aaagagtgtg gacatgtaca   4380
ttgaaagagc aggtgacatc acatgggaaa aagatgcgga agtcactgga aacagtcccc   4440
ggctcgatgt ggcgctagat gagagtggtg atttctccct ggtggaggat gacggtcccc   4500
ccatgagaga gatcatactc aaggtggtcc tgatgaccat ctgtggcatg aacccaatag   4560
ccataccctt tgcagctgga gcgtggtacg tatacgtgaa gactggaaaa aggagtggtg   4620
ctctatggga tgtgcctgct cccaaggaag taaaaaaggg ggagaccaca gatggagtgt   4680
acagagtaat gactcgtaga ctgctaggtt caacacaagt tggagtggga gttatgcaag   4740
agggggtctt tcacactatg tggcacgtca caaaaggatc cgcgctgaga agcggtgaag   4800
ggagacttga tccatactgg ggagatgtca agcaggatct ggtgtcatac tgtggtccat   4860
ggaagctaga tgccgcctgg gacgggcaca gcgaggtgca gctcttggcc gtgccccccg   4920
gagagagagc gaggaacatc cagactctgc ccggaatatt taagacaaag gatggggaca   4980
ttggagcggt tgcgctggat tacccagcag gaacttcagg atctccaatc ctagacaagt   5040
```

-continued

```
gtgggagagt gataggactt tatggcaatg ggtcgtgat caaaaatggg agttatgtta   5100
gtgccatcac ccaagggagg agggaggaag agactcctgt tgagtgcttc gagccttcga   5160
tgctgaagaa gaagcagcta actgtcttag acttgcatcc tggagctggg aaaaccagga   5220
gagttcttcc tgaaatagtc cgtgaagcca taaaaacaag actccgtact gtgatcttag   5280
ctccaaccag ggttgtcgct gctgaaatgg aggaagccct tagagggctt ccagtgcgtt   5340
atatgacaac agcagtcaat gtcacccact ctggaacaga aatcgtcgac ttaatgtgcc   5400
atgccacctt cacttcacgt ctactacagc caatcagagt ccccaactat aatctgtata   5460
ttatggatga ggcccacttc acagatccct caagtatagc agcaagagga tacatttcaa   5520
caagggttga gatgggcgag gcggctgcca tcttcatgac cgccacgcca ccaggaaccc   5580
gtgacgcatt tccggactcc aactcaccaa ttatggacac cgaagtggaa gtcccagaga   5640
gagcctggag ctcaggcttt gattgggtga cggatcattc tggaaaaaca gtttggtttg   5700
ttccaagcgt gaggaacggc aatgagatcg cagcttgtct gacaaaggct ggaaaacggg   5760
tcatacagct cagcagaaag acttttgaga cagagttcca gaaaacaaaa catcaagagt   5820
gggactttgt cgtgacaact gacatttcag agatgggcgc caactttaaa gctgaccgtg   5880
tcatagattc caggagatgc ctaaagccgg tcatacttga tggcgagaga gtcattctgg   5940
ctggacccat gcctgtcaca catgccagcg ctgcccagag gagggggcgc ataggcagga   6000
atcccaacaa acctggagat gagtatctgt atggaggtgg gtgcgcagag actgacgaag   6060
accatgcaca ctggcttgaa gcaagaatgc tccttgacaa tatttacctc caagatggcc   6120
tcatagcctc gctctatcga cctgaggccg acaaagtagc agccattgag ggagagttca   6180
agcttaggac ggagcaaagg aagacctttg tggaactcat gaaaagagga gatcttcctg   6240
tttggctggc ctatcaggtt gcatctgccg gaataaccta cacagataga agatggtgct   6300
ttgatggcac gaccaacaac accataatgg aagacagtgt gccggcagag gtgtggacca   6360
gacacggaga gaaaagagtg ctcaaaccga ggtggatgga cgccagagtt tgttcagatc   6420
atgcggccct gaagtcattc aaggagtttg ccgctgggaa aagaggagcg gcttttggag   6480
tgatggaagc cctgggaaca ctgccaggac acatgacaga gagattccag gaagccattg   6540
acaacctcgc tgtgctcatg cgggcagaga ctggaagcag gccttacaaa gccgcggcgg   6600
cccaattgcc ggagacccta gagaccatta tgcttttggg gttgctggga acagtctcgc   6660
tgggaatctt tttcgtcttg atgaggaaca agggcatagg gaagatgggc tttggaatgg   6720
tgactcttgg ggccagcgca tggctcatgt ggctctcgga aattgagcca gccagaattg   6780
catgtgtcct cattgttgtg ttcctattgc tggtggtgct catacctgag ccagaaaagc   6840
aaagatctcc ccaggacaac caaatggcaa tcatcatcat ggtagcagta ggtcttctgg   6900
gcttgattac cgccaatgaa ctcggatggt tggagagaac aaagagtgac ctaagccatc   6960
taatgggaag gagagaggag ggggcaacca taggattctc aatggacatt gacctgcggc   7020
cagcctcagc ttgggccatc tatgctgcct tgacaacttt cattacccca gccgtccaac   7080
atgcagtgac cacttcatac aacaactact ccttaatggc gatggccacg caagctggag   7140
tgttgtttgg tatgggcaaa gggatgccat tctacgcatg ggactttgga gtcccgctgc   7200
taatgatagg ttgctactca caattaacac ccctgaccct aatagtggcc atcattttgc   7260
tcgtggcgca ctacatgtac ttgatcccag ggctgcaggc agcagctgcg cgtgctgccc   7320
agaagagaac ggcagctggc atcatgaaga accctgttgt ggatggaata gtggtgactg   7380
acattgacac aatgacaatt gacccccaag tggagaaaaa gatgggacag gtgctactca   7440
```

```
tagcagtagc cgtctccagc gccatactgt cgcggaccgc ctgggggtgg ggggaggctg   7500
gggccctgat cacagctgca acttccactt tgtgggaagg ctctccgaac aagtactgga   7560
actcctctac agccacttca ctgtgtaaca tttttagggg aagttacttg gctggagctt   7620
ctctaatcta cacagtaaca agaaacgctg gcttggtcaa gagacgtggg ggtggaacag   7680
gagagaccct gggagagaaa tggaaggccc gcttgaacca gatgtcggcc ctggagttct   7740
actcctacaa aaagtcaggc atcaccgagg tgtgcagaga agaggcccgc cgcgccctca   7800
aggacggtgt ggcaacggga ggccatgctg tgtcccgagg aagtgcaaag ctgagatggt   7860
tggtggagcg gggatacctg cagccctatg gaaaggtcat tgatcttgga tgtggcagag   7920
ggggctggag ttactacgcc gccaccatcc gcaaagttca agaagtgaaa ggatacacaa   7980
aaggaggccc tggtcatgaa gaacccatgt tggtgcaaag ctatgggtgg aacatagtcc   8040
gtcttaagag tggggtggac gtctttcata tggcggctga gccgtgtgac acgttgctgt   8100
gtgacatagg tgagtcatca tctagtcctg aagtggaaga agcacggacg ctcagagtcc   8160
tctccatggt gggggattgg cttgaaaaaa gaccaggagc cttttgtata aaagtgttgt   8220
gcccatacac cagcactatg atggaaaccc tggagcgact gcagcgtagg tatgggggag   8280
gactggtcag agtgccactc tcccgcaact ctacacatga gatgtactgg gtctctggag   8340
cgaaaagcaa caccataaaa agtgtgtcca ccacgagcca gctcctcttg gggcgcatgg   8400
acgggcccag gaggccagtg aaatatgagg aggatgtgaa tctcggctct ggcacgcggg   8460
ctgtggtaag ctgcgctgaa gctcccaaca tgaagatcat tggtaaccgc attgaaagga   8520
tccgcagtga gcacgcggaa acgtggttct ttgacgagaa ccacccatat aggacatggg   8580
cttaccatgg aagctatgag gcccccacac aagggtcagc gtcctctcta ataaacgggg   8640
ttgtcaggct cctgtcaaaa ccctgggatg tggtgactgg agtcacagga atagccatga   8700
ccgacaccac accgtatggt cagcaaagag ttttcaagga aaaagtggac actagggtgc   8760
cagaccccca agaaggcact cgtcaggtta tgagcatggt ctcttcctgg ttgtggaaag   8820
agctaggcaa acacaaacgg ccacgagtct gtaccaaaga agagttcatc aacaaggttc   8880
gtagcaatgc agcattaggg gcaatatttg aagaggaaaa agagtggaag actgcagtgg   8940
aagctgtgaa cgatccaagg ttctgggctc tagtggacaa ggaaagagag caccacctga   9000
gaggagagtg ccagagttgt gtgtacaaca tgatgggaaa aagagaaaag aaacaagggg   9060
aatttggaaa ggccaagggc agccgcgcca tctggtatat gtggctaggg gctagatttc   9120
tagagttcga agcccttgga ttcttgaacg aggatcactg gatggggaga gagaactcag   9180
gaggtggtgt tgaagggctg ggattacaaa gactcggata tgtcctagaa gagatgagtc   9240
gcataccagg aggaaggatg tatgcagatg acactgctgg ctgggacacc cgcatcagca   9300
ggtttgatct ggagaatgaa gctctaatca ccaaccaaat ggagaaaggg cacagggcct   9360
tggcattggc cataatcaag tacacatacc aaaacaaagt ggtaaaggtc cttagaccag   9420
ctgaaaaagg gaagacagtt atggacatta tttcgagaca agaccaaagg gggagcggac   9480
aagttgtcac ttacgctctt aacacattta ccaacctagt ggtgcaactc attcggaata   9540
tggaggctga ggaagttcta gagatgcaag acttgtggct gctgcggagg tcagagaaag   9600
tgaccaactg gttgcagagc aacggatggg ataggctcaa acgaatggca gtcagtggag   9660
atgattgcgt tgtgaagcca attgatgata ggtttgcaca tgccctcagg ttcttgaatg   9720
atatgggaaa agttaggaag gacacacaag agtggaaacc ctcaactgga tgggacaact   9780
```

-continued

```
gggaagaagt tccgttttgc tcccaccact tcaacaagct ccatctcaag gacgggaggt   9840

ccattgtggt tccctgccgc caccaagatg aactgattgg ccgggcccgc gtctctccag   9900

gggcgggatg gagcatccgg gagactgctt gcctagcaaa atcatatgcg caaatgtggc   9960

agctccttta tttccacaga agggacctcc gactgatggc caatgccatt tgttcatctg  10020

tgccagttga ctgggttcca actgggagaa ctacctggtc aatccatgga aagggagaat  10080

ggatgaccac tgaagacatg cttgtggtgt ggaacagagt gtggattgag gagaacgacc  10140

acatggaaga caagacccca gttacgaaat ggacagacat tccctatttg ggaaaaaggg  10200

aagacttgtg gtgtggatct ctcatagggc acagaccgcg caccacctgg gctgagaaca  10260

ttaaaaacac agtcaacatg gtgcgcagga tcataggtga tgaagaaaag tacatggact  10320

acctatccac ccaagttcgc tacttgggtg aagaagggtc tacacctgga gtgctgtaag  10380

caccaatctt agtgttgtca ggcctgctag tcagccacag cttggggaaa gctgtgcagc  10440

ctgtgacccc cccaggagaa gctgggaaac caagcctata gtcaggccga gaacgccatg  10500

gcacggaaga agccatgctg cctgtgagcc cctcagagga cactgagtca aaaaacccca  10560

cgcgcttgga ggcgcaggat gggaaaagaa ggtggcgacc ttccccaccc ttcaatctgg  10620

ggcctgaact ggagatcagc tgtggatctc cagaagaggg actagtggtt agaggagacc  10680

ccccggaaaa cgcaaaacag catattgacg ctgggaaaga ccagagactc catgagtttc  10740

caccacgctg gccgccaggc acagatcgcc gaatagcggc ggccggtgtg gggaaatcca  10800

tgggtct                                                            10807
```

```
<210> SEQ ID NO 43
<211> LENGTH: 44
<212> TYPE: DNA
<213> ORGANISM: Artificial Sequence
<220> FEATURE:
<223> OTHER INFORMATION: Primer sequence

<400> SEQUENCE: 43

agagctcgtt tagtgaaccg agttgttagt ctacgtggac cgac                      44


<210> SEQ ID NO 44
<211> LENGTH: 30
<212> TYPE: DNA
<213> ORGANISM: Artificial Sequence
<220> FEATURE:
<223> OTHER INFORMATION: Primer sequence

<400> SEQUENCE: 44

gctgtgtcac ctaaaatggc cattctcttc                                      30


<210> SEQ ID NO 45
<211> LENGTH: 30
<212> TYPE: DNA
<213> ORGANISM: Artificial Sequence
<220> FEATURE:
<223> OTHER INFORMATION: Primer sequence

<400> SEQUENCE: 45

gaagagaatg gccattttag gtgacacagc                                      30


<210> SEQ ID NO 46
<211> LENGTH: 30
<212> TYPE: DNA
<213> ORGANISM: Artificial Sequence
<220> FEATURE:
<223> OTHER INFORMATION: Primer sequence
```

<400> SEQUENCE: 46
ggaacaatgc cattcccaag actcctagtg 30

<210> SEQ ID NO 47
<211> LENGTH: 30
<212> TYPE: DNA
<213> ORGANISM: Artificial Sequence
<220> FEATURE:
<223> OTHER INFORMATION: Primer sequence

<400> SEQUENCE: 47
cactaggagt cttgggaatg gcattgttcc 30

<210> SEQ ID NO 48
<211> LENGTH: 30
<212> TYPE: DNA
<213> ORGANISM: Artificial Sequence
<220> FEATURE:
<223> OTHER INFORMATION: Primer sequence

<400> SEQUENCE: 48
ggagatcctg acgttccagg agaaaagtcc 30

<210> SEQ ID NO 49
<211> LENGTH: 30
<212> TYPE: DNA
<213> ORGANISM: Artificial Sequence
<220> FEATURE:
<223> OTHER INFORMATION: Primer sequence

<400> SEQUENCE: 49
ggacttttct cctggaacgt caggatctcc 30

<210> SEQ ID NO 50
<211> LENGTH: 32
<212> TYPE: DNA
<213> ORGANISM: Artificial Sequence
<220> FEATURE:
<223> OTHER INFORMATION: Primer sequence

<400> SEQUENCE: 50
ggaattttca atgctatgtc tcaacattgg tg 32

<210> SEQ ID NO 51
<211> LENGTH: 32
<212> TYPE: DNA
<213> ORGANISM: Artificial Sequence
<220> FEATURE:
<223> OTHER INFORMATION: Primer sequence

<400> SEQUENCE: 51
caccaatgtt gagacatagc attgaaaatt cc 32

<210> SEQ ID NO 52
<211> LENGTH: 28
<212> TYPE: DNA
<213> ORGANISM: Artificial Sequence
<220> FEATURE:
<223> OTHER INFORMATION: Primer sequence

<400> SEQUENCE: 52
ctgtcattgc catctgtgtc accatggg 28

<210> SEQ ID NO 53

<211> LENGTH: 28
<212> TYPE: DNA
<213> ORGANISM: Artificial Sequence
<220> FEATURE:
<223> OTHER INFORMATION: Primer sequence
<400> SEQUENCE: 53
cccatggtga cacagatggc aatgacag 28

<210> SEQ ID NO 54
<211> LENGTH: 40
<212> TYPE: DNA
<213> ORGANISM: Artificial Sequence
<220> FEATURE:
<223> OTHER INFORMATION: Primer sequence
<400> SEQUENCE: 54
gatgccatgc cgacccagaa cctgttgatt caacagcacc 40

<210> SEQ ID NO 55
<211> LENGTH: 45
<212> TYPE: DNA
<213> ORGANISM: Artificial Sequence
<220> FEATURE:
<223> OTHER INFORMATION: Primer sequence
<400> SEQUENCE: 55
ggtgctgttg aatcaacagg ttctgggtcg gcatggcatc tccac 45

<210> SEQ ID NO 56
<211> LENGTH: 44
<212> TYPE: DNA
<213> ORGANISM: Artificial Sequence
<220> FEATURE:
<223> OTHER INFORMATION: Primer sequence
<400> SEQUENCE: 56
gtcggtccac gtagactaac aactcggttc actaaacgag ctct 44

<210> SEQ ID NO 57
<211> LENGTH: 10723
<212> TYPE: DNA
<213> ORGANISM: Dengue virus
<400> SEQUENCE: 57
agttgttagt ctacgtggac cgacaaagac agattctttg aggaagctaa gcttaacgta 60
gttctaacag ttttttaatt agagagcaga tctctgatga ataaccaacg gaaaaaggcg 120
agaaatacgc ctttcaatat gctgaaacgc gagagaaacc gcgtgtcaac tgtgcagcag 180
ctgacaaaga gattctcact tggaatgcta cagggacgag gaccattgaa actgttcatg 240
gccctggtgg catttcttcg tttcctaaca atcccgccaa cagcagggat attaaaaaga 300
tggggaacaa tcaaaaaatc aaaggctatc aatgtcttga gagggttcag gaaagagatt 360
ggaaggatgc tgaacatctt gaacaggaga cgcagaaccg caggtataat tattatgatg 420
attccaacag tgatggcgtt ccatttaacc acacgcaacg gagaaccaca catgatcgtc 480
agtagacaag agaaaggaaa aagtcttctg tttaaaacag agaacggtgt gaacatgtgc 540
accctcatgg ccatggacct tggtgaactg tgtgaagaca caatcactta taattgtcct 600
cttctcaagc agaatgaacc agaagacata gactgttggt gcaactctac gtctacatgg 660
gtaacttatg ggacatgcac cgccacagga gaacacagaa gggaaaaaag atcagtggca 720
ctcgttccac atgtgggaat gggactggag acacgaactg aaacatggat gtcatcagaa 780

```
ggggcctgga aacacgccca gagaattgaa acttgggtct tgagacatcc aggcttcacc    840
gtaatggcag caatcctggc atacaccata ggaacgacat atttccaaag agtcctgatt    900
ttcatcttgc tgacagctgt cgctccttca atgacaatgc gttgtatagg aatatcaaat    960
agagactttg tggaaggggt ttcaggagga agctgggttg acatagtctt ggaacatgga   1020
agctgtgtga cgacgatggc gaagaataaa ccaacattgg attttgaact gataaaaaca   1080
gaagccaaac atcccgccac tctaaggaag tattgtatag aggcaaagct gaccaacaca   1140
acaacagcat ctcgctgccc aacacaagga gaacctagcc taaatgaaga acaggacaaa   1200
agatttgtct gcaaacactc catggtagac agaggatggg gaaatggatg cggattattt   1260
ggaaaaggag gcatcgtgac ctgtgcaatg ttcacatgta aaaagaacat ggaaggaaaa   1320
gtcgtgcaac cagaaaattt ggagtacacc attgtgataa cacctcactc aggggaagag   1380
aatgcagtcg gaaatgacac aggaaaacac ggcaaggaaa ttaaagtaac accacagagt   1440
tccatcacag aagcagaact aacaggctat ggcactgtca cgatggaatg ctctccgaga   1500
acgggtctcg acttcaatga gatggtgttg ctgcaaatgg aaaacaaagc ttggctggtg   1560
cacaggcaat ggttcttaga cctgccgtta ccatggctgc ccggagcaga cacacaagga   1620
tcaaactgga tacagaagga gacattggtc actttcaaaa atccccatgc aaagaaacag   1680
gatgttgttg ttttaggatc ccaagaaggg gctatgcata cagcactcac aggggccacg   1740
gaaatccaga tgtcgtcagg aaacttactg ttcacaggac atcttaagtg caggttgaga   1800
atggacaaac tacagctcaa aggaatgtca tattccatgt gtacaggaaa gtttaaagtt   1860
gtgaaggaaa tagcagaaac acaacatgga acaatagtta tcagagtaca atatgaaggg   1920
gacggttctc cgtgcaagat cccttttgaa ataatggact tggaaaaaag acatgtctta   1980
ggtcgcctga ttacagtcaa cccaattgtc acagaaaaag acagcccagt caacatagaa   2040
gcagaacctc cattcggaga cagctatatc attataggag tagaaccggg acaactgaag   2100
ctcagctggt ttaagaaagg aagttctatt ggccaaatgt ttgagacaac aatgagagga   2160
gcgaagagaa tggccatttt aggtgacaca gcttgggatt ttggatccct gggaggagtg   2220
ttcacatcta taggaaaggc cctccaccaa gtctttggag caatctatgg ggctgccttc   2280
agtggggttt catggactat gaaaatcctc ataggagtcg tcatcacatg gataggaatg   2340
aattcacgta gcacctcact gtctgtgtca ttagtattag tgggggtcgt gacactgtat   2400
ttgggagtta tggtgcaggc cgatagtggt tgtgttgtga gttggaaaaa caaagaactg   2460
aaatgtggca gtgggatttt tattacagac aacgtgcaca catggacaga acaatacaaa   2520
ttccaaccag aatccccttc aaagctggct tcagctattc agaaggctca tgaagaaggc   2580
atttgtggaa tccgctcagt aacaagactg gagaatctga tgtggaaaca aataacacca   2640
gaactgaatc acattctatc agaaaatgag gtaaagatga ctatcatgac aggagacatt   2700
aaaggaatta tgcaggcagg aaaacgatcc ctgcggcctc aacccactga gctgaagtac   2760
tcttggaaag catggggcaa agcgaaaatg ctctccacag aacttcataa ccacaccttt   2820
ctcattgatg gccccgaaac agcagaatgt cccaacacaa acagagcttg gaactcacta   2880
gaagttgaag actatggctt tggagtattc accactaaca tatggctgaa attgaaagaa   2940
aggcaggatg tatcttgtga ctcaaaactc atgtcagcag ccataaagga caacagagcc   3000
gtccacgccg acatgggtta ttggatagaa agcgcactca atgacacatg gaagattgag   3060
aaagcctctt tcattgaagt taaaagctgc cactggccaa agtcacacac cctctggagt   3120
```

-continued

```
aatggagtgc tagaaagtga gatgataatt ccaaagaatt ttgcaggacc agtatcacaa   3180
cacaattata gaccaggcta tcatacacaa acggcaggac cctggcatct aggtaggctt   3240
gagatggact ttgatttctg cgaaggaacc acagtggtgg tgactgagga ctgtggaaat   3300
agaggaccct ctttaagaac aaccactgct tctggaaaac tcataacaga gtggtgctgc   3360
cgatcttgca cattaccacc actaaggtac agaggtgagg atggatgctg gtatggaatg   3420
gaaatcagac cattgaaaga gaaagaagag aacttggtca actctttggt cacagccgga   3480
catggacaga ttgacaactt ctcactagga gtcttgggaa tggcattgtt cctggaagag   3540
atgctcagga cccgagtagg aacgaaacat gcaatattac tagttgcagt ttctttcgtg   3600
acattgatca cagggaacat gtcctttcga gatttgggga gagtgatggt catggtgggc   3660
gctaccatga cggatgacat aggcatgggc gtgacttatc ttgccctatt agcagccttc   3720
aaagtcagac caacttttgc agctggacta ctcttaagaa agctgacctc caaggaattg   3780
atgatgacca ccataggaat cgtactcctc tcccagagca ccataccaga gactatactt   3840
gaactgactg acgcgttggc tttagggatg atggttctta aagtagtgag aaacatggaa   3900
aagtaccaac tagcagtgac tatcatggcc atcttgtgcg tcccaaatgc agtgatatta   3960
caaaacgcat ggaaagtgag ctgcacaaca ctggcagtgg tgtccgtttc cccactgctt   4020
ttaacatcct cacagcagaa agcggattgg ataccactgg cgttgacgat caaaggcctc   4080
aatccaacag ccattttctt aacaaccctc tcaagaacta gcaagaaaag gagctggcca   4140
ctaaacgagg ctattatggc agtcgggatg gtgagcattt tagccagttc tctcttaaaa   4200
aatgatattc ccatgacagg accattagtg gctggagggc ttctcactgt gtgttacgtg   4260
ctcactggaa gatcggctga tttggaactg gagagagctg ctgacgtaag atgggaagaa   4320
caagcagaga tatcaggaag tagtccaatt ctgtcgataa caatatcgga agatggtagc   4380
atgtcgataa aaaatgaaga agaagaacaa acactgacca tactcattag aacaggactg   4440
ctggtgatat caggactttt tcccgtgtca ataccaatca cggcagctgc atggtacctg   4500
tgggaagtga aaaaacaacg agcaggagta ttgtgggatg tcccttcacc cccacctgtg   4560
ggaaaggctg aactggaaga tggagcctat agaatcaagc agaaagggat tctaggatac   4620
tcgcagatcg gagccggagt ttacaaagaa ggaacattcc acacaatgtg gcatgtcaca   4680
cgtggtgctg tcctaatgca taaagggaag agaattgaac catcatgggc ggacgtcaag   4740
aaagacctaa tatcgtatgg aggaggctgg aagctagaag gagaatggaa ggaaggagaa   4800
gaagtccagg tcctggcatt agagcctgga aagaatccaa gagccgtcca aacaaaaccc   4860
ggtcttttta aaactaacac tggaaccata ggcgccgtgt ctctggactt ttctcctgga   4920
acgtcaggat ctccaatcgt cgacaaaaaa ggaaaagttg tgggccttta tggtaacggt   4980
gtcgtcacaa ggagtggaac atatgtgagt gccatagccc agactgaaaa aagcatcgaa   5040
gacaatccag agattgaaga tgacatcttt cgaaagaaaa gattgaccat catggacctt   5100
cacccaggag caggaaaaac aaagagatac cttccagcaa tagtcagaga agccataaaa   5160
cgaggcttga gaacactaat cctggccccc actagagttg tggcggctga aatggaagaa   5220
gctctcagag gacttccaat aagataccaa accccagcta tcagagctga gcacactggg   5280
cgggagattg tggatctaat gtgtcacgcc acatttacca tgaggctact atcaccaatt   5340
agagtgccaa attacaacct gattatcatg gatgaagccc atttcacaga cccagcaagc   5400
atagcagcta gaggatacat ttcaactcga gtagagatgg gtgaagcagc tgggattttt   5460
atgacagcta cccccccagg aagcagagac ccatttcctc agagcaatgc accaatcatg   5520
```

-continued

```
gatgaagaaa gggaaatccc tgagcgttcg tggaactctg gacatgagtg ggtcacggat   5580
tttaaaggga agactgtttg gtttgttcca agtataaaag cagggaatga tatagcagct   5640
tgcctgagaa agaatggaaa gaaagtgata caactcagca ggaagacctt tgattctgaa   5700
tatatcaaga ctaggaccaa tgattgggac tttgtggtca cgacagacat ttcagaaatg   5760
ggtgctaact tcaaggccga gagggttata gaccccagac gctgcatgaa accagtaata   5820
ctaacagatg gtgaagagcg ggtaatcttg gcaggaccca tgccagtgac ccactctagt   5880
gcagcacaaa gaagagggag agtaggaaga aatccaaaaa atgaaagtga ccagtacata   5940
tacatggggg aacctctgga aaatgatgaa gactgtgcac actggaaaga agctaagatg   6000
cttctagata acatcaacac gcctgaagga atcattccca gcatgttcga accagagcgt   6060
gaaaaggtgg acgccattga tggtgaatac cgcttgagag gagaagcgag gaaaactttc   6120
gtggacctaa tgagaagagg agacctacca gtctggctag cctacagagt ggcagctgaa   6180
ggtatcaact acgcagacag aaggtggtgc tttgatggag tcaagaacaa ccaaatcttg   6240
gaagaaaatg tggaagtgga aatttggaca aaagaaggag aaaggaagaa attaaaaccc   6300
agatggttgg atgctaggat ctattctgac ccactggcgc tcaaagaatt caaggaattc   6360
gcagctggaa gaaagtccct gaccctgaat ctaatcacag agatgggtag gctcccaacc   6420
ttcatgaccc agaaagcaag gaatgcactg gacaacttag cagtcttgca cacggctgaa   6480
gcaggcggaa gggcgtacaa tcatgctctt agtgaactgc cggagactct ggagacattg   6540
cttttactga cacttttggc cacagtcacg ggcggaatct tcctgttctt gatgagcgga   6600
aagggtatag ggaagatgac cctgggaatg tgttgcataa tcacggccag tattctccta   6660
tggtatgcac aaatacagcc acactggata gcagcttcaa taatactgga gtttttctc    6720
atagtcttgc tcattccaga accagaaaag cagagaacac cccaagataa ccaattaact   6780
tatgttgtca tagccatcct tacagtggta gctgcaacca tggcaaacga gatgggtttc   6840
ctggaaaaaa caaagaaaga ttttggattg ggaagcagta caacccagca acatgagagc   6900
aacatcctgg acatagatct acgtcctgca tcagcttgga ctctatatgc cgtggcaaca   6960
actttcatca caccaatgtt gagacatagc attgaaaatt cctcagtgaa tgtgtctcta   7020
acagccattg ccaaccaagc cacagtgtta atgggtcttg ggaaaggatg gccattgtca   7080
aaaatggaca tcggagttcc ccttctcgcc atcgggtgct attcacaagt caaccccata   7140
actctcacag cagcccttct ctcattggta gcacattatg ccatcatagg gccaggactc   7200
caagcgaaag caactagaga ggctcagaaa agagcagcag cgggcatcat gaaaaaccca   7260
actgtggatg gaataacagt gattgaccta gatccaatac cctatgatcc aaagtttgaa   7320
aagcagctgg gacaagtaat gctcttagtc ctctgcgtga ctcaagtgtt gatgatgagg   7380
actacatggg ctttatgtga agctctaacc ttagcaaccg ggcccatctc tacactgtgg   7440
gaaggaaatc cagggagatt ttggaataca actattgcag tgtcaatggc taacattttt   7500
agagggagtt acctggccgg agccggactt ctcttctcta tcatgaagaa cacggccaac   7560
acaagaaggg gaactggcaa cacaggagag acgcttggag agaaatggaa aaaccggttg   7620
aatgcattgg ggaagagtga attccagatc tataagaaaa gtggaatcca ggaagtggat   7680
agaaccttag caaaagaagg catcaaaaga ggagaaacgg accatcacgc tgtgtcgcga   7740
ggctcggcga aactgagatg gttcgtcgag agaaacctgg tcacaccaga agggaaagta   7800
gtggaccttg gctgcggcag ggggggctgg tcatactatt gtgggggact aaagaatgta   7860
```

-continued

```
aaagaagtca aaggcctaac aaaaggagga ccaggacacg aagaacctat tcccatgtca   7920
acatacggtt ggaatctggt gcgtcttcaa agtggagttg atgttttttt tactccgcca   7980
gaaaagtgtg acacattgct gtgtgacata ggggagtcat caccaaaccc cacggttgag   8040
gcaggaagaa cactcagagt tctaaactta gtggaaaatt ggctgaacaa caacacccaa   8100
ttttgcataa aggttctcaa cccatatatg ccctcagtta tagaaaaaat ggaagcgcta   8160
caaaggaaat acggaggagc tttggtgaga aatccactct cacgaaattc cacacacgag   8220
atgtactggg tatccaatgc ttccgggaac atagtgtcat cagtgaacat gatttcaaga   8280
atgttaatta acagattcac aatgagacac aagaaggcca catacgagcc agatgttgac   8340
ctcggaagtg gaactcgcaa tatcggaatt gaaagtgaga caccaaattt agacataatt   8400
gggaaaagaa tagaaaaaat aaaacaagag catgaaacat catggcacta tgaccaagac   8460
cacccataca aaacgtgggc ctaccatggc agctacgaaa caaaacagac tggatcagca   8520
tcatccatgg tgaacggagt ggttaggctg ctaacaaaac cttgggatgt catccccatg   8580
gtgacacaga tggcaatgac agacacgact ccatttggac aacagcgcgt tttcaaagag   8640
aaggtggaca cgagaaccca agaaccgaaa gaaggcacga aaaagctaat gaaaatcacg   8700
gcagaatggc tctggaaaga actaggaaag aaaaagacac ctaggatgtg caccagagaa   8760
gaattcacaa gaaaggtgag aagcaatgca gccttaggtg ccatattcac tgatgagaac   8820
aagtggaagt cggcacgtga ggctgttgaa gacagtggat tttgggagtt ggttgacaag   8880
gaaaggaatc tccatcttga aggaaagtgt gagacatgtg tgtacaacat gatgggaaag   8940
agagagaaga agctagggga gttcggcaaa gcaaaaggca gcagagccat atggtacatg   9000
tggcttggag cacgcttctt agagtttgaa gccctaggat tcttgaatga agatcactgg   9060
ttttccagag agaactccct gagtggagtg gaaggagaag ggctgcacaa actaggctac   9120
attttaagag acgtgagtaa gaaagaagga ggagcaatgt acgccgatga caccgcagga   9180
tgggacacaa gaatcacact agaggactta aaaaatgaag aaatggtgac aaaccacatg   9240
gaaggagaac acaagaaact tgctgaagcc attttcaaat taacgtacca aaacaaggtg   9300
gtgcgtgtac aaagaccaac accaagaggc acagtaatgg acattatatc gagaagagac   9360
caaagaggta gtggacaagt cgtcacttat ggcctcaata ctttcaccaa catggaagcc   9420
caactgatca gacagatgga gggagaagga gtcttcaaaa gcatccagca actgacagcc   9480
acagaagaaa ttgcagtgaa aaactggtta gtaagagtgg ggcgtgagag gttatcaaga   9540
atggccatca gtggagatga ttgtgttgtg aaacccttag atgacaggtt tgcaagcgct   9600
ctaacagctc taaatgacat gggaaaggtt aggaaagaca tacagcaatg ggaaccttca   9660
agaggatgga acgattggac acaagtgccc ttttgttcac accatttcca tgagttaatc   9720
atgaaggacg gtcgtgtact cgtagttcca tgcagaaacc aagatgaact gattggtagg   9780
gcccgaattt cccagggagc cgggtggtcc ttgcgggaaa cagcctgttt ggggaagtct   9840
tacgcccaaa tgtggagcct gatgtacttc cacagacgcg atcttaggct ggcggcaaat   9900
gccatttgct cggcagtccc atcacactgg gttccaacaa gtcgaacaac ctggtccata   9960
cacgccacac atgagtggat gacaacagaa gacatgctga cagtctggaa cagggtgtgg  10020
atccaagaaa acccatggat ggaagacaag actccagtag aatcatggga ggaaatcccg  10080
tatttgggga aaagagaaga ccaatggtgc ggctcattga ttgggctaac aagcagggcc  10140
acctgggcaa agaacatcca aacagcaata aatcaagtta gatccctaat aggcaatgag  10200
gaatacacag actacatgcc atccatgaaa agatttagaa gagaagagga agaggcagga  10260
```

gtcttgtggt agaaagcaga aacatcatga gacaaagtca gaagtcaggt cggattaagc 10320
catagtacgg aaaaaactgt gctacctgtg agccccgtcc aaggacgtta aaagaggtca 10380
ggccactaca agtgccatag cttgagtaaa ctgtgcagcc tgtagctcca cctgagaagg 10440
tgtaaaaaat ctgggaggcc acaaaccatg gaagctgtac gcatggcgta gtggactagc 10500
ggttagagga gacccctccc ttacaaatcg cagcaacaat gggggcccaa ggtgagatga 10560
agctgtagtc tcactgaaag gactagaggt tagaggagac ccccccgaaa taaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 58
<211> LENGTH: 10723
<212> TYPE: DNA
<213> ORGANISM: Dengue virus

<400> SEQUENCE: 58
agttgttagt ctacgtggac cgacaaagac agattctttg aggaagctaa gcttaacgta 60
gttctaacag tttttaatt agagagcaga tctctgatga ataaccaacg gaaaaaggcg 120
agaaatacgc ctttcaatat gctgaaacgc gagagaaacc gcgtgtcaac tgtgcagcag 180
ctgacaaaga gattctcact tggaatgcta cagggacgag gaccattgaa actgttcatg 240
gccctggtgg catttcttcg tttcctaaca atcccgccaa cagcagggat attaaaaaga 300
tggggaacaa tcaaaaaatc aaaggctatc aatgtcttga gagggttcag gaaagagatt 360
ggaaggatgc tgaacatctt gaacaggaga cgcagaaccg caggtataat tattatgatg 420
attccaacag tgatggcgtt ccatttaacc acacgcaacg gagaaccaca catgatcgtc 480
agtagacaag agaaaggaaa aagtcttctg tttaaaacag agaacggtgt gaacatgtgc 540
accctcatgg ccatggacct tggtgaactg tgtgaagaca caatcactta taattgtcct 600
cttctcaagc agaatgaacc agaagacata gactgttggt gcaactctac gtctacatgg 660
gtaacttatg ggacatgcac cgccacagga gaacacagaa gggaaaaaag atcagtggca 720
ctcgttccac atgtgggaat gggactggag acacgaactg aaacatggat gtcatcagaa 780
ggggcctgga aacacgccca gagaattgaa acttgggtct tgagacatcc aggcttcacc 840
gtaatggcag caatcctggc atacaccata ggaacgacat atttccaaag agtcctgatt 900
ttcatcttgc tgacagctgt cgctccttca atgacaatgc gttgtatagg aatatcaaat 960
agagactttg tggaaggggt ttcaggagga agctgggttg acatagtctt ggaacatgga 1020
agctgtgtga cgacgatggc gaagaataaa ccaacattgg attttgaact gataaaaaca 1080
gaagccaaac atcccgccac tctaaggaag tattgtatag aggcaaagct gaccaacaca 1140
acaacagcat ctcgctgccc aacacaagga gaacctagcc taaatgaaga acaggacaaa 1200
agatttgtct gcaaacactc catggtagac agaggatggg gaaatggatg cggattattt 1260
ggaaaaggag gcatcgtgac ctgtgcaatg ttcacatgta aaaagaacat ggaaggaaaa 1320
gtcgtgcaac cagaaaattt ggagtacacc attgtgataa cacctcactc aggggaagag 1380
aatgcagtcg gaaatgacac aggaaaacac ggcaaggaaa ttaaagtaac accacagagt 1440
tccatcacag aagcagaact aacaggctat ggcactgtca cgatggaatg ctctccgaga 1500
acgggtctcg acttcaatga gatggtgttg ctgcaaatgg aaaacaaagc ttggctggtg 1560
cacaggcaat ggttcttaga cctgccgtta ccatggctgc ccggagcaga cacacaagga 1620

-continued

```
tcaaactgga tacagaagga gacattggtc actttcaaaa atccccatgc aaagaaacag   1680
gatgttgttg ttttaggatc ccaagaaggg gctatgcata cagcactcac aggggccacg   1740
gaaatccaga tgtcgtcagg aaacttactg ttcacaggac atcttaagtg caggttgaga   1800
atggacaaac tacagctcaa aggaatgtca tattccatgt gtacaggaaa gtttaaagtt   1860
gtgaaggaaa tagcagaaac acaacatgga acaatagtta tcagagtaca atatgaaggg   1920
gacggttctc cgtgcaagat cccttttgaa ataatggact tggaaaaaag acatgtctta   1980
ggtcgcctga ttacagtcaa cccaattgtc acagaaaaag acagcccagt caacatagaa   2040
gcagaacctc cattcggaga cagctatatc attataggag tagaaccggg acaactgaag   2100
ctcagctggt ttaagaaagg aagttctatt ggccaaatgt ttgagacaac aatgagagga   2160
gcgaagagaa tggccatttt aggtgacaca gcttgggatt ttggatccct gggaggagtg   2220
ttcacatcta taggaaaggc cctccaccaa gtctttggag caatctatgg ggctgccttc   2280
agtggggttt catggactat gaaaatcctc ataggagtcg tcatcacatg gataggaatg   2340
aattcacgta gcacctcact gtctgtgtca ttagtattag tgggggtcgt gacactgtat   2400
ttgggagtta tggtgcaggc cgatagtggt tgtgttgtga gttggaaaaa caaagaactg   2460
aaatgtggca gtgggatttt tattacagac aacgtgcaca catggacaga acaatacaaa   2520
ttccaaccag aatccccttc aaagctggct tcagctattc agaaggctca tgaagaaggc   2580
atttgtggaa tccgctcagt aacaagactg gagaatctga tgtggaaaca aataacacca   2640
gaactgaatc acattctatc agaaaatgag gtaaagatga ctatcatgac aggagacatt   2700
aaaggaatta tgcaggcagg aaaacgatcc ctgcggcctc aacccactga gctgaagtac   2760
tcttggaaag catggggcaa agcgaaaatg ctctccacag aacttcataa ccacaccttt   2820
ctcattgatg gccccgaaac agcagaatgt cccaacacaa acagagcttg gaactcacta   2880
gaagttgaag actatggctt tggagtattc accactaaca tatggctgaa attgaaagaa   2940
aggcaggatg tatcttgtga ctcaaaactc atgtcagcag ccataaagga caacagagcc   3000
gtccacgccg acatgggtta ttggatagaa agcgcactca atgacacatg gaagattgag   3060
aaagcctctt tcattgaagt taaaagctgc cactggccaa agtcacacac cctctggagt   3120
aatggagtgc tagaaagtga gatgataatt ccaaagaatt ttgcaggacc agtatcacaa   3180
cacaattata gaccaggcta tcatacacaa acggcaggac cctggcatct aggtaggctt   3240
gagatggact ttgatttctg cgaaggaacc acagtggtgg tgactgagga ctgtggaaat   3300
agaggaccct ctttaagaac aaccactgct tctggaaaac tcataacaga gtggtgctgc   3360
cgatcttgca cattaccacc actaaggtac agaggtgagg atggatgctg gtatggaatg   3420
gaaatcagac cattgaaaga gaaagaagag aacttggtca actctttggt cacagccgga   3480
catggacaga ttgacaactt ctcactagga gtcttgggaa tggcattgtt cctggaagag   3540
atgctcagga cccgagtagg aacgaaacat gcaatattac tagttgcagt ttctttcgtg   3600
acattgatca cagggaacat gtcctttcga gatttgggga gagtgatggt catggtgggc   3660
gctaccatga cggatgacat aggcatgggc gtgacttatc ttgccctatt agcagccttc   3720
aaagtcagac caacttttgc agctggacta ctcttaagaa agctgacctc caaggaattg   3780
atgatgacca ccataggaat cgtactcctc tcccagagca ccataccaga gactatactt   3840
gaactgactg acgcgttggc tttagggatg atggttctta aagtagtgag aaacatggaa   3900
aagtaccaac tagcagtgac tatcatggcc atcttgtgcg tcccaaatgc agtgatatta   3960
caaaacgcat ggaaagtgag ctgcacaaca ctggcagtgg tgtccgtttc cccactgctt   4020
```

ttaacatcct cacagcagaa agcggattgg ataccactgg cgttgacgat caaaggcctc 4080
aatccaacag ccattttctt aacaaccctc tcaagaacta gcaagaaaag gagctggcca 4140
ctaaacgagg ctattatggc agtcgggatg gtgagcattt tagccagttc tctcttaaaa 4200
aatgatattc ccatgacagg accattagtg gctggagggc ttctcactgt gtgttacgtg 4260
ctcactggaa gatcggctga tttggaactg gagagagctg ctgacgtaag atgggaagaa 4320
caagcagaga tatcaggaag tagtccaatt ctgtcgataa caatatcgga agatggtagc 4380
atgtcgataa aaaatgaaga agaagaacaa acactgacca tactcattag aacaggactg 4440
ctggtgatat caggactttt tcccgtgtca acaccaatca cggcagctgc atggtacctg 4500
tgggaagtga aaaaacaacg agcaggagta ttgtgggatg tcccttcacc cccacctgtg 4560
ggaaaggctg aactggaaga tggagcctat agaatcaagc agaaagggat tctaggatac 4620
tcgcagatcg gagccggagt ttacaaagaa ggaacattcc acacaatgtg gcatgtcaca 4680
cgtggtgctg tcctaatgca taaagggaag agaattgaac catcatgggc ggacgtcaag 4740
aaagacctaa tatcgtatgg aggaggctgg aagctagaag gagaatggaa ggaaggagaa 4800
gaagtccagg tcctggcatt agagcctgga aagaatccaa gagccgtcca aacaaaaccc 4860
ggtcttttta aaactaacac tggaaccata ggcgccgtgt ctctggactt ttctcctgga 4920
acgtcaggat ctccaatcgt cgacaaaaaa ggaaaagttg tgggccttta tggtaacggt 4980
gtcgtcacaa ggagtggaac atatgtgagt gccatagccc agactgaaaa aagcatcgaa 5040
gacaatccag agattgaaga tgacatcttt cgaaagaaaa gattgaccat catggacctt 5100
cacccaggag caggaaaaac aaagagatac cttccagcaa tagtcagaga agccataaaa 5160
cgaggcttga gaacactaat cctggccccc actagagttg tggcggctga aatggaagaa 5220
gctctcagag gacttccaat aagataccaa accccagcta tcagagctga gcacactggg 5280
cgggagattg tggatctaat gtgtcacgcc acatttacca tgaggctact atcaccaatt 5340
agagtgccaa attacaacct gattatcatg gatgaagccc atttcacaga cccagcaagc 5400
atagcagcta gaggatacat ttcaactcga gtagagatgg gtgaagcagc tgggattttt 5460
atgacagcta ccccccccagg aagcagagac ccatttcctc agagcaatgc accaatcatg 5520
gatgaagaaa gggaaatccc tgagcgttcg tggaactctg gacatgagtg ggtcacggat 5580
tttaaaggga agactgtttg gtttgttcca agtataaaag cagggaatga tatagcagct 5640
tgcctgagaa agaatggaaa gaaagtgata caactcagca ggaagacctt tgattctgaa 5700
tatatcaaga ctaggaccaa tgattgggac tttgtggtca cgacagacat ttcagaaatg 5760
ggtgctaact tcaaggccga gagggttata gaccccagac gctgcatgaa accagtaata 5820
ctaacagatg gtgaagagcg ggtaatcttg gcaggaccca tgccagtgac ccactctagt 5880
gcagcacaaa gaagagggag agtaggaaga aatccaaaaa atgaaagtga ccagtacata 5940
tacatggggg aacctctgga aaatgatgaa gactgtgcac actggaaaga agctaagatg 6000
cttctagata acatcaacac gcctgaagga atcattccca gcatgttcga accagagcgt 6060
gaaaaggtgg acgccattga tggtgaatac cgcttgagag gagaagcgag gaaaactttc 6120
gtggacctaa tgagaagagg agacctacca gtctggctag cctacagagt ggcagctgaa 6180
ggtatcaact acgcagacag aaggtggtgc tttgatggag tcaagaacaa ccaaatcttg 6240
gaagaaaatg tggaagtgga aatttggaca aaagaaggag aaaggaagaa attaaaaccc 6300
agatggttgg atgctaggat ctattctgac ccactggcgc tcaaagaatt caaggaattc 6360

-continued

```
gcagctggaa gaaagtccct gaccctgaat ctaatcacag agatgggtag gctcccaacc   6420
ttcatgaccc agaaagcaag gaatgcactg gacaacttag cagtcttgca cacggctgaa   6480
gcaggcggaa gggcgtacaa tcatgctctt agtgaactgc cggagactct ggagacattg   6540
cttttactga cacttttggc cacagtcacg ggcggaatct tcctgttctt gatgagcgga   6600
aagggtatag ggaagatgac cctgggaatg tgttgcataa tcacggccag tattctccta   6660
tggtatgcac aaatacagcc acactggata gcagcttcaa taatactgga gtttttctc    6720
atagtcttgc tcattccaga accagaaaag cagagaacac cccaagataa ccaattaact   6780
tatgttgtca tagccatcct tacagtggta gctgcaacca tggcaaacga gatgggtttc   6840
ctggaaaaaa caaagaaaga ttttggattg ggaagcagta caacccagca acatgagagc   6900
aacatcctgg acatagatct acgtcctgca tcagcttgga ctctatatgc cgtggcaaca   6960
actttcatca caccaatgtt gagacatagc attgaaaatt cctcagtgaa tgtgtctcta   7020
acagccattg ccaaccaagc cacagtgtta atgggtcttg ggaaaggatg gccattgtca   7080
aaaatggaca tcggagttcc ccttctcgcc atcgggtgct attcacaagt caaccccata   7140
actctcacag cagcccttct ctcattggta gcacattatg ccatcatagg gccaggactc   7200
caagcgaaag caactagaga ggctcagaaa agagcagcag cgggcatcat gaaaaaccca   7260
actgtggatg gaataacagt gattgaccta gatccaatac cctatgatcc aaagtttgaa   7320
aagcagctgg gacaagtaat gctcttagtc ctctgcgtga ctcaagtgtt gatgatgagg   7380
actacatggg ctttatgtga agctctaacc ttagcaaccg ggcccatctc tacactgtgg   7440
gaaggaaatc cagggagatt ttggaataca actattgcag tgtcaatggc taacattttt   7500
agagggagtt acctggccgg agccggactt ctcttctcta tcatgaagaa cacggccaac   7560
acaagaaggg gaactggcaa cacaggagag acgcttggag agaaatggaa aaaccggttg   7620
aatgcattgg ggaagagtga attccagatc tataagaaaa gtggaatcca ggaagtggat   7680
agaaccttag caaaagaagg catcaaaaga ggagaaacgg accatcacgc tgtgtcgcga   7740
ggctcggcga aactgagatg gttcgtcgag agaaacctgg tcacaccaga agggaaagta   7800
gtggaccttg gctgcggcag gggggctgg tcatactatt gtgggggact aaagaatgta    7860
aaagaagtca aaggcctaac aaaaggagga ccaggacacg aagaacctat tcccatgtca   7920
acatacggtt ggaatctggt gcgtcttcaa agtggagttg atgtttttt tactccgcca    7980
gaaaagtgtg acacattgct gtgtgacata ggggagtcat caccaaaccc cacggttgag   8040
gcaggaagaa cactcagagt tctaaactta gtggaaaatt ggctgaacaa caacacccaa   8100
ttttgcataa aggttctcaa cccatatatg ccctcagtta tagaaaaaat ggaagcgcta   8160
caaaggaaat acggaggagc tttggtgaga aatccactct cacgaaattc cacacacgag   8220
atgtactggg tatccaatgc ttccgggaac atagtgtcat cagtgaacat gatttcaaga   8280
atgttaatta acagattcac aatgagacac aagaaggcca catacgagcc agatgttgac   8340
ctcggaagtg gaactcgcaa tatcggaatt gaaagtgaga caccaaattt agacataatt   8400
gggaaaagaa tagaaaaaat aaaacaagag catgaaacat catggcacta tgaccaagac   8460
cacccataca aaacgtgggc ctaccatggc agctacgaaa caaaacagac tggatcagca   8520
tcatccatgg tgaacggagt ggttaggctg ctaacaaaac cttgggatgt catccccatg   8580
gtgacacaga tggcaatgac agacacgact ccatttggac aacagcgcgt tttcaaagag   8640
aaggtggaca cgagaaccca agaaccgaaa gaaggcacga aaaagctaat gaaaatcacg   8700
gcagaatggc tctggaaaga actaggaaag aaaaagacac ctaggatgtg caccagagaa   8760
```

-continued

```
gaattcacaa gaaaggtgag aagcaatgca gccttaggtg ccatattcac tgatgagaac   8820
aagtggaagt cggcacgtga ggctgttgaa gacagtggat tttgggagtt ggttgacaag   8880
gaaaggaatc tccatcttga aggaaagtgt gagacatgtg tgtacaacat gatgggaaag   8940
agagagaaga agctagggga gttcggcaaa gcaaaaggca gcagagccat atggtacatg   9000
tggcttggag cacgcttctt agagtttgaa gccctaggat tcttgaatga agatcactgg   9060
ttttccagag agaactccct gagtggagtg gaaggagaag ggctgcacaa actaggctac   9120
attttaagag acgtgagtaa gaaagaagga ggagcaatgt acgccgatga caccgcagga   9180
tgggacacaa gaatcacact agaggactta aaaaatgaag aaatggtgac aaaccacatg   9240
gaaggagaac acaagaaact tgctgaagcc attttcaaat taacgtacca aaacaaggtg   9300
gtgcgtgtac aaagaccaac accaagaggc acagtaatgg acattatatc gagaagagac   9360
caaagaggta gtggacaagt cgtcacttat ggcctcaata ctttcaccaa catggaagcc   9420
caactgatca gacagatgga gggagaagga gtcttcaaaa gcatccagca actgacagcc   9480
acagaagaaa ttgcagtgaa aaactggtta gtaagagtgg ggcgtgagag gttatcaaga   9540
atggccatca gtggagatga ttgtgttgtg aaacccttag atgacaggtt tgcaagcgct   9600
ctaacagctc taaatgacat gggaaaggtt aggaaagaca tacagcaatg ggaaccttca   9660
agaggatgga acgattggac acaagtgccc ttttgttcac accatttcca tgagttaatc   9720
atgaaggacg gtcgtgtact cgtagttcca tgcagaaacc aagatgaact gattggtagg   9780
gcccgaattt cccagggagc cgggtggtcc ttgcgggaaa cagcctgttt ggggaagtct   9840
tacgcccaaa tgtggagcct gatgtacttc cacagacgcg atcttaggct ggcggcaaat   9900
gccatttgct cggcagtccc atcacactgg gttccaacaa gtcgaacaac ctggtccata   9960
cacgccacac atgagtggat gacaacagaa gacatgctga cagtctggaa cagggtgtgg  10020
atccaagaaa acccatggat ggaagacaag actccagtag aatcatggga ggaaatcccg  10080
tatttgggga aaagagaaga ccaatggtgc ggctcattga ttgggctaac aagcagggcc  10140
acctgggcaa agaacatcca aacagcaata aatcaagtta gatccctaat aggcaatgag  10200
gaatacacag actacatgcc atccatgaaa agatttagaa gagaagagga agaggcagga  10260
gtcttgtggt agaaagcaga aacatcatga gacaaagtca gaagtcaggt cggattaagc  10320
catagtacgg aaaaaactgt gctacctgtg agccccgtcc aaggacgtta aaagaggtca  10380
ggccactaca agtgccatag cttgagtaaa ctgtgcagcc tgtagctcca cctgagaagg  10440
tgtaaaaaat ctgggaggcc acaaaccatg gaagctgtac gcatggcgta gtggactagc  10500
ggttagagga gacccctccc ttacaaatcg cagcaacaat gggggcccaa ggtgagatga  10560
agctgtagtc tcactgaaag gactagaggt tagaggagac ccccccgaaa taaaaaacag  10620
catattgacg ctgggaaaga ccagagatcc tgctgtctcc tcagcatcat tccaggcaca  10680
gaacgccaga aaatggaatg gtgctgttga atcaacaggt tct                    10723
```

RAPID METHOD OF GENERATING LIVE ATTENUATED VACCINES

CROSS-REFERENCE TO RELATED APPLICATIONS

This application is a continuation of U.S. application Ser. No. 16/093,262, filed Oct. 12, 2018, which is a national phase application of International Application No. PCT/SG2017/050211, filed Apr. 13, 2017, which claims the benefit of priority of Singapore application no. 10201602980W, filed on Apr. 14, 2016, the contents of each being hereby incorporated by reference in their entireties for all purposes.

FIELD OF THE INVENTION

The invention relates to a method of generating a live attenuated vaccine, in particular, a live attenuated viral vaccine.

BACKGROUND OF THE INVENTION

Live attenuated vaccines (LAVs) are vaccines that contain pathogens, including viruses that are viable but have reduced virulence. LAVs are typically more effective than inactivated vaccines and have been successful in preventing many viral diseases, including smallpox, chickenpox, measles, mumps, rubella and yellow fever.

Conventionally, LAV development has mostly relied on chance discovery of attenuated strains of pathogens upon serial passage in cell lines or animals. More recently, targeted site-directed mutagenesis has been employed to develop "attenuated" strains of pathogens although these candidates have yet to be translated into vaccines for use in humans. Consequently, identifying suitably attenuated strains of pathogens for further development into vaccines remains a lengthy process, typically involving years, with a hit or miss outcome. In addition to unreliable outcomes, current methods of vaccine development involve significant costs.

Therefore, there is a need to provide a rapid and reliable method to generate LAVs that overcome, or at least ameliorate the disadvantages described above.

SUMMARY OF THE INVENTION

In one aspect, there is provided a method of generating a live attenuated vaccine (LAV) comprising the steps of:

a) modifying an original virus to generate at least one genetically distinct maladapted virus;
b) infecting a host cell with said at least one maladapted virus;
c) selecting a host cell that displays a preselected phenotype in response to said infection with said at least one maladapted virus and isolating the viral nucleic acid of said maladapted virus from the host cell;
d) sequencing the isolated viral nucleic acid of said maladapted virus and comparing this to the nucleic acid sequence of the original virus;
e) reconstructing the maladapted virus from the original virus to produce a candidate live attenuated vaccine; and
f) screening said candidate live attenuated vaccine for a predetermined phenotype.

In another aspect, there is provided a live attenuated vaccine produced according to the method as described herein.

Definitions

The following words and terms used herein shall have the meaning indicated:

"Vaccine" refers to a biological preparation that provides acquired immunity to a particular disease. A vaccine comprises an agent that stimulates the immune response to give rise to acquired immunity. The agent in a vaccine may include but is not limited to one or more of an inactivated pathogen, an attenuated pathogen, an inactivated toxin (toxoid), a protein subunit or a conjugate of an antigen and a carrier.

"Live attenuated vaccine" or "LAV" refers to a vaccine that comprises an attenuated virus that is viable but has a reduced virulence.

The terms "modifying" and "modification" with respect to an original virus refer to the generation of one or more genetically distinct maladapted viruses from an original virus. A maladapted virus is one which is maladapted to the intended host to prevent adaptation of the virus to the host's innate immunity. Modification also allows the generation of a population of genetically diverse viruses for selection of a variety of diverse viruses for downstream applications. Maladapted viruses may be generated by any means that introduces genetic changes into the genome of a virus.

"Host cell" refers to a cell that is to be, or is, infected with a virus of interest. Similarly, a "host organism" refers to an organism that is to be, or is, infected with a virus of interest.

"Inducible reporter" refers to a reporter gene whose expression is under the control of a promoter element. Activation of the promoter element by, for example a transcription factor, induces the expression of the reporter gene. Expression of the reporter gene can then be detected by suitable detection means.

"Innate immunity" will be generally understood to those skilled in the art to refer to the non-specific defense mechanism that is activated immediately or shortly after exposure to an antigen. Mechanisms involved in the innate immune response may include physical barriers such as epithelial surfaces, activation of inflammatory responses, phagocytosis, complement activation, activation of Toll-like receptors and secretion of cytokines such as interferons.

"Site directed mutagenesis" refers to the introduction of one or more specific mutations at one or more predetermined locations within a nucleic acid sequence.

"Reconstructed virus" refers to a virus that has been generated by altering the genome of an original virus to replicate the genome of a maladapted virus. In particular, the sequence of the original virus is altered to conform to the sequence of the maladapted virus.

Alteration of the genome of the original virus may be by mutagenesis, such as site directed mutagenesis, of one or more infectious clones generated from the virus and/or by excision or insertion of sections of nucleic acids. "Reconstructed virus" may also refer to a viral genome that has been synthesized chemically, in the absence of cells. Chemical synthesis of a viral genome may involve the chemical synthesis of short fragments of nucleic acids and assembly of the fragments together to form a synthetic viral genome. A reconstructed virus may also be replicated in a host cell to scale up production of the reconstructed virus for downstream applications.

"Infectious clone" refers to a plasmid comprising viral genetic material that has been introduced into the plasmid. Infectious clones may be generated using routine methods well known to those skilled in the art.

"Operably linked" or "operatively linked" refers to the relationship between two or more nucleotide sequences that interact physically or functionally. For example, a promoter or regulatory nucleotide sequence is said to be operably linked to a nucleotide sequence that codes for a RNA or a protein if the two sequences are situated such that the regulatory nucleotide sequence will affect the expression level of the coding or structural nucleotide sequence. A 5' portion of a gene is operatively or operably linked with a 3' portion of a gene if the two portions are situated to form a functional gene.

"Nucleic acid" means any single or double-stranded RNA or DNA molecule, such as mRNA, cDNA, genomic DNA and xeno DNA.

It will be generally understood that the term "growth rate" of a virus refers to the replication rate of the virus within a host cell or host organism. It will also be generally understood that a host cell or host organism may be infected with a virus for a predetermined period of time. Growth or replication rate of a virus may be determined by measuring the percentage of host cells infected with a specific viral nucleic acid or protein at predetermined time intervals.

"Virus" refers broadly to an infectious agent that replicates within the cells of other organisms. Viruses may be classified based on their nucleic acid (RNA or DNA), whether the nucleic acid is single stranded or double stranded, whether reverse transcriptase is utilized, and if their nucleic acid is single stranded RNA, whether it is sense (+) or antisense (−).

"Serotype" means an immunologically distinguishable variant of a virus antigen such that one serotype may be distinguished by an immune system from a different serotype. For example, dengue virus serotype 1 is immunologically distinguishable from dengue virus serotype 2.

"Virus strain" refers to a genetic variant or subtype of a virus species or serotype. It will be generally understood that strains may have similar or different phenotypes, including but not limited to virulence, rate of growth and infectivity.

"Dengue virus" refers to a small, enveloped, positive-stranded RNA virus that belongs to the Flavivirus genus of the Flaviviridae family. There are four dengue virus serotypes: dengue-1 (DENV-1 or D1), dengue-2 (DENV-2 or D2), dengue-3 (DENV-3 or D3), and dengue-4 (DENV-4 or D4). Each one of these subtypes forms an antigenically distinct subgroup within the flavivirus family.

"Zika virus" refers to a positive-stranded RNA virus that belongs to the Flavivirus genus of the Flaviviridae family. At present, one Zika virus (ZIKV) serotype has been identified. Strains of ZIKV can be grouped into two distinct genetic lineages, African and Asian.

It will be generally understood that the term "immunogenicity" of a virus refers to the propensity of a virus to trigger the immune response of a host cell or organism. Immunogenicity may be measured by the expression or upregulation of the expression of markers associated with the immune response.

It will be generally understood that the expression or upregulation of the expression markers may be determined by assays routine in the art, including but not limited to gene expression assays and protein assays. Gene expression assays include but are not limited to polymerase chain reaction (PCR) and microarray. It will be understood that PCR includes real time PCR, quantitative and semi-quantitative PCR. The expression or upregulation of the expression of markers may also be determined by protein assays including but not limited to Western blotting and ELISA.

It will be generally understood that "virus uptake" refers to the infectivity of a virus. Virus uptake may be determined by measuring the amount of viral specific nucleic acid sequences or protein within the host cell or host organism.

"Sterilizing immunity" refers to an immune status wherein infection of a host by a virus is prevented as a result of vaccination. Sterilizing immunity may be indicated by undetectable levels of viremia in a host.

"Subject" refers to an animal or plant. Examples of animals include but are not limited to a primate, a mouse, a rat, a guinea pig, a rabbit or a dog. In a preferred embodiment, the subject is a human.

The invention illustratively described herein may suitably be practised in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE PRESENT INVENTION

Figure 1:
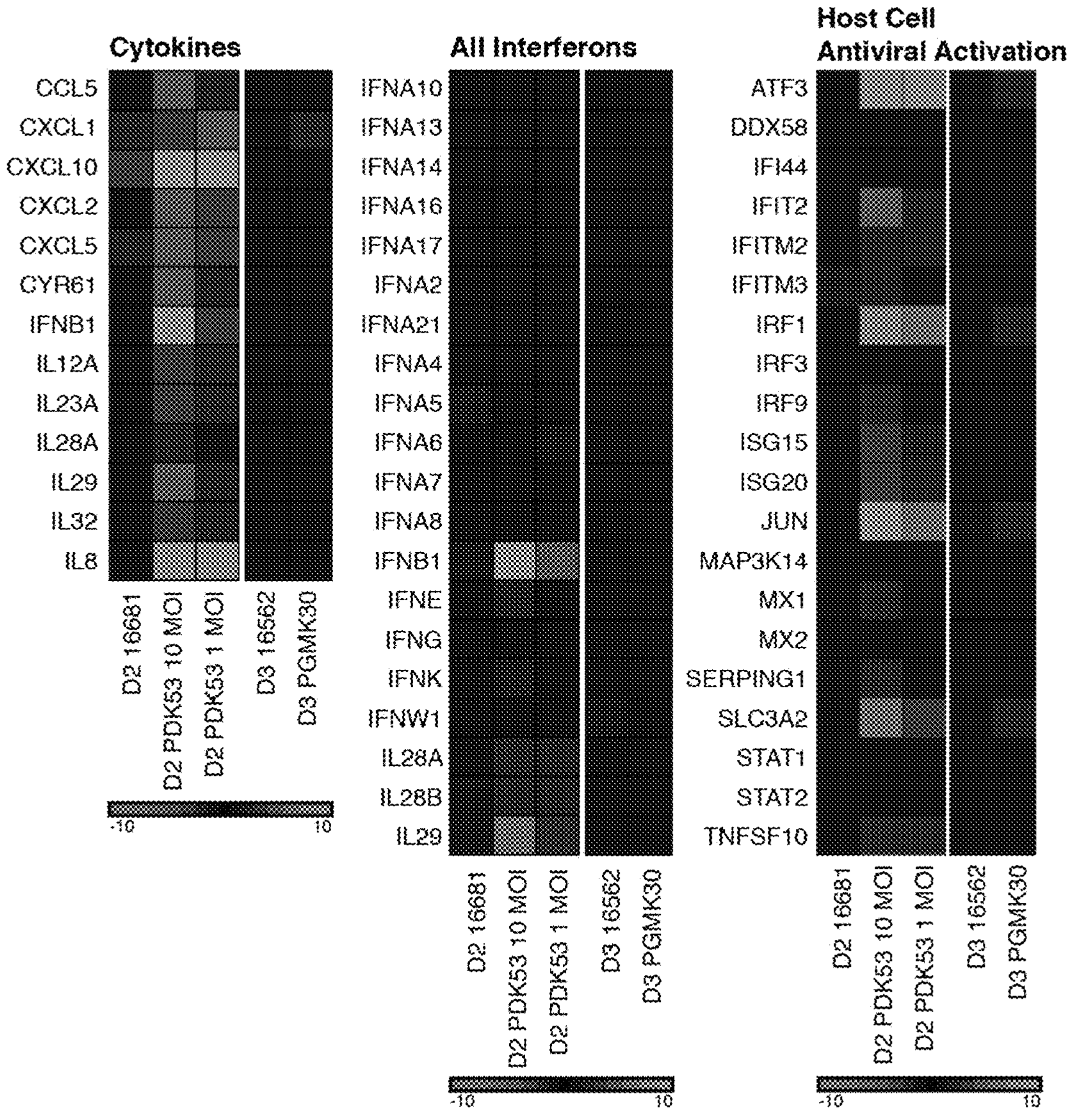
FIG. 1 is a heat map of innate immune genes and antiviral proteins in cells infected with each DENV strain relative to uninfected cells and shows that DENV-2 PDK53 infection strongly up-regulates host immune response. Whole genome microarray analysis was performed on Human hepatoma-7 (HuH-7) cells infected with DENV-2 and DENV-3 vaccine and wild-type strains at 10 multiplicity of infection (MOI) for 24 hours. Additionally DENV-2 PDK53 infection was performed at 1 MOI for 24 hours. Expression levels of innate immune genes including cytokines, interferon and other related antiviral proteins, relative to cells infected with each DENV strain relative to uninfected cells, are shown.

In a first aspect the present invention refers to a method of generating a live attenuated vaccine (LAV) comprising the steps of:

a) modifying an original virus to generate at least one genetically distinct maladapted virus;
b) infecting a host cell with said at least one maladapted virus;
c) selecting a host cell that displays a preselected phenotype in response to said infection with said at least one maladapted virus and isolating the viral nucleic acid of said maladapted virus from the host cell;
d) sequencing the isolated viral nucleic acid of said maladapted virus and comparing this to the nucleic acid sequence of an original virus;
e) reconstructing the maladapted virus from the original virus to produce a candidate live attenuated vaccine; and
f) screening said candidate live attenuated vaccine for a predetermined phenotype.

A virus may be modified to generate one or more genetically distinct maladapted viruses by any means that introduces mutations in the genome of the virus. For example, modification of a virus may be achieved by passaging the virus at least once in a cell or cell line that is of a species distinct from the intended recipient of the LAV. Advantageously, passaging the virus in a cell that is of a species other than the intended host prevents the virus from adapting to the host's innate immunity.

A suitable cell that may be used to modify a virus may be one that is obtained from a primary cell culture or a continuous cell line. The cell culture may be an adherent cell culture or a suspension cell culture. The cell may be from a human, a bovine, a canine, a murine, a rat, a fish, an insect, a rabbit or monkey cell culture line, provided the cell is of a distinct species from the intended host.

Suitable examples of cells that may be used include but are not limited to the human hepatoma cell line HuH-7, the human embryonic kidney cell line HEK293T, human embryonic diploid cells (e.g. human lung fibroblast cells WI-38 and MRCS), C6/36 mosquito cell line, Vero cells, MDCK cells and primary green monkey kidney cells. In a preferred embodiment, the cell used to maladapt a virus for subsequent selection for human vaccine applications is a MDCK cell. In yet another embodiment, the cell used to modify a virus for subsequent selection for human vaccine applications is a primary monkey kidney cell. In a further preferred embodiment, the cell used to modify a virus for subsequent selection for human vaccine applications is a C6/36 mosquito cell. In a further preferred embodiment, the cell used to modify a virus for subsequent selection for human vaccine applications is a Vero mosquito cell.

Modification of a virus may also be achieved by culturing a cell or cell line that has been infected with the virus under sub-optimal conditions. It will generally be understood that sub-optimal conditions refer to conditions under which growth of a cell or cell line is hampered. Sub-optimal conditions may include culturing a cell or cell line at a temperature that is lower or higher than 37° C., passaging the cell or cell line at a density that is too low, passaging the cell or cell line in the suboptimal cell culture medium or exposing the cell to a pH that is lower or higher than 7. In a preferred embodiment, modification of a virus may be achieved by culturing a cell infected with the virus at a temperature that is lower than 37° C.

Another method of modification of a virus may also be achieved by exposure to a chemical compound. For example, the chemical compound may be a chemically derived mutagen, such as ribavirin and 5-fluorouracil. The virus may be exposed to the mutagen once or may be subjected to continuous or repeated exposure. It will generally be understood, and appreciated by those of skill in the art, that the chemical compound used as well as the length of exposure to the chemical compound in order to achieve modification would vary depending on the type of virus or virus strain.

Another possible method of modifying a virus may be by random mutation of the viral genome. Random mutagenesis may be achieved by error prone polymerase chain reaction (PCR). Error prone PCR may utilize low fidelity or error prone DNA polymerase that does not have proof-reading capability. Error prone PCR may also utilize variations in reaction conditions of the PCR to introduce errors. For example, the concentration and components within the PCR reaction buffer may be varied. Thermal cycling conditions may also be varied. An example of an error prone DNA polymerase is error prone Taq DNA polymerase which has an error rate of $2.2\times10^{-5}$ errors per nucleotide per cycle.

Subsequent to error prone PCR, PCR products may be gel purified and assembled to obtain an infectious clone. In one embodiment, assembly of PCR products may be by Gibson assembly.

It will generally be understood that modification of a virus may take place via one or more of the methods described herein, either alone or in combination.

In one embodiment, the maladapted virus may be generated by exposure of cells, infected with a virus, to 5-fluorouracil during cell culture. In another embodiment, the maladapted virus may be generated by exposure of cells, infected with a virus, to ribavirin during cell culture. In yet another embodiment, the maladapted virus may be generated by exposure of cells, infected with a virus, to 5-fluorouracil and ribavirin during cell culture.

The concentration of mutagen used may range from about 10 μM to about 10 mM, from about 50 μM to about 5 mM, from about 100 μM to about 3 mM, from about 100 μM to about 2 mM, from about 100 μM to about 1 mM, from about 200 μM to about 900 μM, from about 300 μM to about 800 μM, from about 400 μM to about 700 μM or from about 500 μM to about 600 μM. In a preferred embodiment, the concentration of 5-fluorouracil is about 100 μM to about 1 mM.

Cells infected with a virus may also be exposed to one or more mutagens for at least 1 day, at least 2 days, at least 3 days, at least 4 days, at least 5 days, at least 6 days or at least 1 week. In a preferred embodiment, cells are exposed to one or more mutagens for 5 days.

The virus may be passaged one or more times in a cell either in the presence or absence of a chemical mutagen. For example, a cell infected with the virus may be passaged 1, 2, 3, 4, 5, 6, 7, 8, 9, 10, 11, 12, 13, 14, 15, 16, 17, 18, 19 or 20 times. In a preferred embodiment, a virus may be passaged in a cell no more than 10 times, or no more than 5 times. In a further preferred embodiment, a virus may be passaged in a cell no more than 5 times. In a preferred embodiment, the virus may be passaged once in the presence of a chemical mutagen. The cells may be exposed to a chemical mutagen at every passage. The cells may also be exposed to a chemical mutagen at every second passage. Variation in the exposure of cells to a chemical mutagen and/or number of passages performed will be understood to be routine in the art.

In one embodiment, the virus to be modified is derived from a clinical isolate. A clinical isolate may include but is not limited to blood, blood plasma, serum, buccal smear, amniotic fluid, prenatal tissue, sweat, nasal swab, urine, organs, tissues, fractions, and cells isolated from mammals including humans. Clinical isolates also may include sections of the biological sample including tissues (for example, sectional portions of an organ or tissue). Clinical isolates may also include extracts from a biological sample, for example, an antigen from a biological fluid (for example, blood or urine). In a preferred embodiment, a clinical isolate is a virus strain isolated from blood or serum.

In one embodiment, the maladapted virus generated as described herein is then isolated, using standard methods known in the art, and used to infect a host cell, at step b) of the method as described herein. Advantageously, this host cell may also be used to select for a specific maladapted virus that induces a preselected phenotype in the host cell. For example, the host cell may comprise an inducible reporter gene, operably linked to at least one promoter associated with innate immunity to at least one virus, and the host cell may then be used to select for a specific maladapted virus with a propensity to activate, for example, a type I interferon response. Typically, when using a host cell to select for a specific maladapted virus of interest, a host cell that is of the same species as the intended vaccine is used. In one embodiment, the host cell used to select for a specific maladapted virus that induces a predetermined phenotype in the host cell is a cell of human origin. For example, a suitable host cell is a cell of a human hepatoma cell line or a human kidney cell line. In one embodiment, the host cell used to select for specific maladapted viruses that induce a predetermined phenotype in the host cell is a HEK293T cell. In a preferred embodiment, the host cell used to select for a specific virus that induces a predetermined phenotype in the host cell is a HuH-7 cell.

It will be appreciated that inducible reporter genes are well known in the art and are typically expressed under the control of a promoter. Suitable examples of reporter genes include but are not limited to green fluorescent protein (GFP), red fluorescent protein (RFP), yellow fluorescent protein (YFP), β-galactosidase and luciferase. In a preferred embodiment, the inducible reporter is green fluorescent protein (GFP).

The promoter element of an inducible reporter gene may be activated by one or more markers. A marker may provide an indication of a physiological state, based on its presence or absence or based on its relative levels in a cell or organism. In some embodiments the one or more markers may comprise a nucleic acid, a protein or a chemical. In yet another embodiment, a marker may be a protein or a compound associated with a biochemical pathway or with the innate immune response. Suitable examples of markers associated with innate immunity include proteins and/or genes of, or associated with, the interferon and inflammatory response pathways, such as type I interferon; an interferon-stimulated gene (ISG); Signal Transducer and Activator of Transcription 1 (STAT1); interferon regulatory factors, for example IRF3, IRF7 or IRF9; and Nuclear Factor Kappa-Light Chain-Enhancer of Activated B cells (NF-κB). Type I interferons may include IFN-α (alpha), IFN-β (beta), IFN-κ (kappa), IFN-δ (delta), IFN-ε (epsilon), IFN-τ (tau), IFN-ω (omega), and IFN-ζ (zeta).

In one embodiment, the inducible reporter gene may be operably linked to at least one promoter associated with innate immunity; for example, an interferon stimulated response element (ISRE). In a preferred embodiment, the inducible reporter comprises an ISRE operably linked to a green fluorescent protein (GFP) gene. In a more preferred embodiment the ISRE is associated with an IRF3-mediated response.

Selection of host cells expressing a reporter gene may be done by flow cytometry, fluorescence activated cell sorting (FACS), magnetic activated cell sorting (MACS) or laser capture microdissection. In a preferred embodiment, the host cell may be selected and isolated by FACS.

In another example, a preselected phenotype may be plaque size in a plaque assay. Plaque assays are generally understood in the art to be used for purifying or isolating a clonal population of virus or to determine viral titer. Plaque sizes may be compared relative to another plaque within the same assay or within the same plate, or relative to another plaque in a separate assay or on a separate plate. A plaque of interest may then be selected by picking the plaque from the assay or plate for subsequent applications. In a preferred embodiment, the preselected phenotype may be small plaque size relative to a host cell that has been infected with the original virus. In another embodiment, the preselected phenotype may be small plaque size relative to another plaque within the same assay or plate.

The selected host cell is then treated with general methods well known in the art to isolate the nucleic acid of the maladapted virus from the host cell.

The isolated nucleic acid of the maladapted virus from step c) is then sequenced (step d). In one embodiment, sequencing may be by Sanger sequencing or Next-Generation Sequencing. It will be appreciated by those of skill in the art that Next-Generation Sequencing encompasses a wide variety of sequencing methods including, but not limited to, whole genome sequencing, transcriptome sequencing and epigenome sequencing. In one embodiment, the Next-Generation Sequencing platform used is Deep Sequencing.

The sequence of the isolated nucleic acid of the maladapted virus is then compared to the nucleic acid sequence of the original virus. In one embodiment, the viral nucleic acid sequence of one or more maladapted viruses is compared to the nucleic acid sequence of the original virus to identify mutations that occur in more than a threshold percentage of the isolated maladapted virus sequences; for example, one or more mutations that occur in, for example, over 50% of isolated sequences. In one embodiment, the threshold percentage is at least 10% of the viral nucleic acid sequences isolated from step c). In some embodiments, the threshold percentage is at least 20%, at least 30%, at least 40%, at least 50%, at least 60%, at least 70%, at least 80%, at least 90% or 100% of the viral nucleic acid sequences isolated from step c). It will be understood that a consensus nucleic acid sequence may be determined using the threshold percentage. For example, for a given nucleic acid position, if 40% of analyzed sequences have an adenine (A), 30% of analyzed sequences have a cytosine (C), and 30% of analyzed sequences have a guanine (G), the consensus nucleic acid at this given position would be adenine (A). A consensus nucleic acid sequence may be obtained by comparing the viral nucleic acid sequence of at least 2 maladapted viruses to the nucleic acid sequence of the original virus.

Comparison of the sequence of the isolated nucleic acid of the maladapted virus to the nucleic acid sequence of the original virus from which the maladapted virus is derived may include the use of bioinformatics tools to assemble and analyze the sequences of the isolated and original viral nucleic acid. For example, sequences may be aligned to a reference genome using Burrows-Wheeler Aligner (BWA) and its variants, for example, BWA-MEM; Clustal and its variants, for example, ClustalW; or MUSCLE. SAMtools may also be used to manage and convert alignment files. A consensus sequence may also be obtained with SAMtools. Variants in nucleic acid sequence from a reference genome can also be derived with SAMtools or other programs such as LoFreq, Geneious, Unipro UGENE and the like. It will be appreciated by those of skill in the art that one, or a combination, of the tools described herein may be utilized for purposes of analyzing sequencing results.

Accordingly, it will be generally understood that the nucleic acid sequence of the maladapted virus from step c) can be obtained by Sanger sequencing or Next-Generation Sequencing (e.g. Deep sequencing), by determining a consensus sequence using a threshold percentage, by using bioinformatics tools, or combinations thereof.

In some embodiments, the maladapted virus is mutated at one or more positions within a consensus nucleic acid sequence. In other embodiments, the maladapted virus sequence is mutated at one or more positions in the maladapted virus sequence with respect to the nucleic acid sequence of the original virus. In yet another embodiment, the maladapted virus is mutated at position 876 from thymine (T) to cytosine (C), or at position 2925 from adenine (A) to guanine (G) or both.

Using the results of the sequence comparison from step d), the maladapted virus may then be reconstructed from the original virus (step e). In one embodiment, reconstruction of the maladapted virus in step e) comprises performing site directed mutagenesis on the nucleic acid sequence of the original virus to conform said original viral nucleic acid sequence to the nucleic acid sequence of the maladapted virus.

It will generally be understood that reconstruction of the maladapted virus involves standard methods known in the art. Briefly, an infectious clone of the original virus is generated. Mutations that were identified in step d) that occur in more than a threshold percentage of the isolated maladapted virus sequences are introduced into the infectious clone either by site-directed mutagenesis and/or by excision or insertion of segments of nucleic acids to replicate the genetic changes identified in the maladapted virus. The reconstructed virus may then be packaged using methods known in the art to generate a candidate live attenuated vaccine.

It will be generally understood that vaccine candidates may be screened in vitro and/or in vivo for a predetermined phenotype. A predetermined phenotype may provide an indication of the suitability and safety of the vaccine.

In one embodiment, the screening in step f) may be performed in vitro and/or in vivo. In vitro and in vivo screening may be performed sequentially or simultaneously. In vitro screening may include, but is not limited to, analysis of the growth or replication rate of the candidate live attenuated vaccine; the infectivity or uptake of the candidate live attenuated vaccine; the ability of the candidate live attenuated vaccine to trigger or induce the innate immune response in the host cell and plaque size formation. In one embodiment, in vitro screening may involve measuring: one or more of increased growth rate, immunogenicity, generation of small plaques in plaque assays and increased rate of virus uptake, relative to at least one other candidate vaccine.

The growth or replication rate of a candidate live attenuated vaccine may be determined by measuring the levels of a specific nucleic acid in a host cell that has been infected. For example, the growth rate of the candidate live attenuated dengue vaccine may be measured using the specific viral DENV E protein or nucleic acid. Growth or replication rate may also be measured at predetermined time intervals, for example, at 6-hour, 12-hour, 24-hour and 36-hour intervals. In one embodiment, measurement of growth or replication rate may be determined at 24-hour intervals.

It will be understood that prior to measuring the growth rate of the candidate live attenuated vaccine, the host cell may be infected for a preselected period of time. For example, the host cell may be infected for 1 hour, 2 hours, 3 hours, 4 hours, 5 hours, 6 hours, 12 hours, 24 hours or 36 hours prior to the levels of a specific viral nucleic acid in a host cell being measured. In a preferred embodiment, the host cell is infected for 2 hours prior to measurement.

In addition to growth and replication rate of a candidate live attenuated vaccine, another factor that contributes to the suitability of a candidate as a live attenuated vaccine is its immunogenicity. Immunogenicity may be determined for example by measuring virus uptake in the host cell. Virus uptake may be determined by measuring the amount of viral-specific nucleic acid sequences or protein within the host cell or host organism. In one embodiment, the viral-specific nucleic acid is a DENV specific cross-serotype sequence. It will be generally understood that amounts of viral nucleic acids for all DENV serotypes can be determined by measuring the amounts or expression levels of nucleic acids using conserved sequences (i.e. cross-serotype/pan-serotype sequences) between the various serotypes.

In vivo screening may include, but is not limited to, exposing an animal to the candidate live attenuated vaccine and analyzing the safety and potency of the candidate. Suitable animals may include mouse or non-human primate animal models. In some embodiments, such models may be inoculated with a vaccine candidate and then infected with a virus, for example dengue virus or Zika virus, and monitored for viremia, disease, weight loss, sterilizing immunity or mortality.

It will be appreciated by those of skill in the art that the present invention applies to viruses in general. Examples of viruses include but are not limited to dengue virus, Zika virus, yellow fever virus, respiratory syncytial virus, cytomegalovirus, Kaposi's sarcoma-associated herpes virus, Epstein-Barr virus, Human papillomavirus and Japanese encephalitis virus. In one embodiment, the virus is a virus of the Flaviviridae family. In another embodiment, the virus is selected from a dengue virus, a yellow fever virus, human immunodeficiency virus (HIV), Zika virus or a Japanese encephalitis virus. In a preferred embodiment, the virus is selected from the *Aedes* mosquito-borne group of flaviviruses, in particular DENV-1, DENV-2. DENV-3, DENV-4 and Zika. In yet another preferred embodiment, the virus is DENV-2 or DENV-3.

Examples of virus strains include, but are not limited to, strains derived from a clinical isolate. For example, a virus strain may be a strain derived by exposure of a clinical isolate to a chemical mutagen and/or multiple passaging. In one embodiment, a virus strain is DENV-2 PDK53 or DENV-2 16681. In another embodiment, a virus strain is DENV-3 PGMK30 or DENV-3 16562. In another embodiment, a virus strain is a French Polynesian strain of Zika virus (ZIKV). In a preferred embodiment, the ZIKV strain is PF13/251013-18.

The vaccine disclosed in the present invention will be generally understood as being administered to a subject in need thereof either in a single dose or in multiple doses. In one embodiment, the vaccine may be administered in a single dose. In another embodiment, the vaccine may be administered in two or more doses. The vaccine disclosed in the present invention may be administered alone or in combination with a buffer. An example of a suitable buffer is phosphate buffered saline. The vaccine of the present invention may be in lyophilized or aqueous form, with or without stabilizers in the final formulation. It will generally be understood by one of skill in the art that a lyophilized vaccine must be reconstituted in a suitable medium prior to administration to a subject.

Suitable routes of administration of the pharmaceutical composition or vaccine described herein, to a subject, in particular to a human subject, may include, without limitation, oral, rectal, transmucosal or intestinal administration or intramuscular, subcutaneous, intramedullary, intrathecal, direct intraventricular, intravenous, intravitreal, intraperitoneal, intranasal, intradermal or intraocular injections. In a preferred embodiment, the route of administration is by intradermal or subcutaneous injection.

In another embodiment, there is provided a live attenuated vaccine produced according to the method as described herein.

EXPERIMENTAL SECTION

Background

DENV-2 PDK53 and DENV-3 PGMK30, which are two DENV LAVs that had been previously used in a clinical trial, were studied. DENV-2 PDK53 was generated from the wild-type strain DENV-2 16681 while DENV-3 PGMK30 was generated from the wild-type strain DENV-3 16562. In the trial, DENV-2 PDK53 was well tolerated and induced protective immune responses, whilst DENV-3 PGMK30 caused dengue-like syndrome in vaccinees. Both strains were developed using the same attenuation process, which involved serial passaging of clinical isolates in primary mammalian cells with periodic selection for viral clones that displayed small plaque phenotype. Until now, it has been believed that viruses which produce smaller plaques are less fit and are, hence, attenuated. Although the preparation of both attenuated strains was guided by the same selection guidelines, the disparate clinical results suggest a fundamental difference in the cellular events leading to the same outcome in this empirically defined criterion.

Accordingly, by studying the differences in the various attributes of DENV infection that are thought to influence plaque sizes, the present study investigated whether DENV-2 PDK53 and DENV-3 PGMK30 produced smaller plaques compared to their respective parental clinical isolates due to distinct mechanisms.

The present study also used a novel method for generating a candidate LAV.

Materials and Methods

General materials and methods used in the study are provided below.

Cells, Viruses and Reagents

Vero, HuH-7 and Raji cells stably expressing dendritic cell-specific intercellular adhesion molecule-3-grabbing non-integrin (DC-SIGN) receptor were cultured in Dulbecco's Modified Essential Medium (DMEM) while human monocytic cells THP-1, BHK21 cells and C6/36 cells were cultured in RPMI Medium 1640 (Gibco) supplemented with 10% foetal calf serum. Primary human monocytes were derived from blood obtained from a donor wherein whole blood was spun down in a Ficoll gradient to isolate peripheral blood mononuclear cells (PBMCs). The PBMCs were then allowed to adhere to plastic tissue culture flasks for 48 hours. Non-adherent cells were washed off with sterile PBS, leaving behind cells enriched for primary human monocytes. DENV strains of the original Mahidol stocks (DENV-2 16681, DENV-2 PDK53, DENV-3 16562 and DENV-3 PGMK30FRhL3) were obtained from Dr Claire Huang (Centres for Disease Control and Prevention, USA) and were passaged three times in C6/36 cells. To achieve sufficiently high titres for subsequent experiments, supernatant of PDK53 cultures were concentrated by high-speed centrifugation and reconstituted in 1/100 of its original culture volume. Viral genome sequences were uploaded to GenBank with the accession numbers listed in Table 1. Yellow fever YF-17D was commercially obtained (Sanofi Pasteur).

TABLE 1

Dengue and Zika genome sequences.

| Virus Strain | GenBank Accession Number |
|---|---|
| DENV-2 16681 | KU725663 |
| DENV-2 PDK53 | KU725664 |
| DENV-3 16562 | KU725665 |
| DENV-3 PGMK30FRhL3 | KU725666 |

Random Mutagenesis by PCR

Six PCR products derived from DENV2 strain were generated by 6 sets of primer pairs that are routinely used in the laboratory for Gibson assembly (Table 7). For this PCR reaction, high fidelity Q5® High-Fidelity DNA polymerase (New England BioLabs) is used. To introduce random mutagenesis to each of these fragments, Taq DNA polymerase was used instead for PCR amplification of each fragments. The PCR products are gel purified and assembled by Gibson assembly to obtain infectious clone which will then be transfected into HEK293T cells. Supernatant was plagued to observe for different plaque size. Small plaque phenotype were individually picked and expanded for sequencing analysis.

TABLE 2

Primers used for Gibson assembly for ZIKV

| | |
|---|---|
| Fragment 1 (2137 bp) | |
| PF13 F1 Fwd | AGAGCTCGTTTAGTGAACCGAGTTGTTGATCTG (SEQ ID NO: 1) |
| PF13 F1 Rev | GTGGATCAAGTTCCAGCATCATCTTAGAGTTCTCAGTGC (SEQ ID NO: 2) |
| Fragment 2 (2316 bp) | |
| PF13 F2 Fwd | GCACTGAGAACTCTAAGATGATGCTGGAACTTGATCCAC (SEQ ID NO: 3) |
| PF13 F2 Rev | CACCTGCTCTTTCAATGTACATGTCCACACTCTTTCCTGA (SEQ ID NO: 4) |
| Fragment 3 (1832 bp) | |
| PF13 F3 Fwd | TCAGGAAAGAGTGTGGACATGTACATTGAAAGAGCAGGTG (SEQ ID NO: 5) |
| PF13 F3 Rev | CTAAGCTTGAACTCTCCCTCAATGGCTGCTACTTTGTCG (SEQ ID NO: 6) |
| Fragment 4 (2570 bp) | |
| PF13 F4 Fwd | CGACAAAGTAGCAGCCATTGAGGGAGAGTTCAAGCTTAG (SEQ ID NO: 7) |
| PF13 F4 Rev | CATACGGTGTGGTGTCGGTCATGGCTATTCCTGTGACTCC (SEQ ID NO: 8) |
| Fragment 5 (2145 bp) | |
| PF13 F5 Fwd | GGAGTCACAGGAATAGCCATGACCGACACCACACCGTATG (SEQ ID NO: 9) |
| PF13 F5 Rev | ATGCCATGCCGACCCAGACCCATGGATTTCCCCACACCGG (SEQ ID NO: 10) |

TABLE 2-continued

| Primers used for Gibson assembly for ZIKV | |
|---|---|
| Vector Amplification | |
| PF13 Vector Fwd | TGGGGAAATCCATGGGTCTGGGTCGGCATGGCATCTCCAC (SEQ ID NO: 11) |
| PF13 Vector Rev | CACAGATCAACAACTCGGTTCACTAAACGAGCTCTGCT (SEQ ID NO: 12) |

Plaque Purification

BHK-21 was seeded in a 6-well plate 2 days before it was infected with approximately 15 plaque-forming units of PF13/251013-18 per well. After 1-hour adsorption of inoculum at 37° C., inoculum was removed and overlaid with maintenance media containing 0.9% agarose. Plaques that have big or small plaques were isolated for Sanger sequencing and also passaging in Vero for verification of plaque size by plaque assay.

Infectious Clone Generation

Genomic RNA of PF13/251013-18 and DV2-3295 were extracted using QIAamp Viral RNA Mini Kit (Qiagen) and cDNA synthesized using SuperScript III First-Strand Synthesis Kit (Invitrogen) before PCR amplification as 5 fragments for PF13/251013-18 and 6 fragments for DV2-3295 (primers in Tables 2 and 7 respectively) using Q5® High-Fidelity 2× Master Mix (New England BioLabs). TA cloning of these fragments into pGEMT® vector (Promega) was performed to generate individual plasmids for each fragment. Site-directed mutagenesis on relevant plasmids was performed to generate specific mutations identified for DN-1, DN-2, DN-3, DN-4, D2-A and D2-B using QuikChange II Site-Directed Mutagenesis Kit (Agilent). Infectious clones for the different mutant were generated using Gibson assembly with NEBuilder® HiFi DNA Assembly Master Mix (New England BioLabs) to assemble their genomes into a vector containing a constitutive CMV immediate-early promoter.

Mutant Virus Production

Assembled infectious clones of DN-1, DN-2, DN-3, DN-4, DV2-3295, D2-A and D2-B were transfected into HEK293T cells using Lipofectamine 2000 as per manufacturer's instructions and viruses produced from these cells were harvested 48 hours post-transfection. Virus progeny was amplified in Vero cells up to 2 passages to generate working viral stocks.

Infection of A129 Mice

Virus stocks for animal infection were diluted in sterile PBS and titers determined prior to injection. Male A129 mice between 11 to 14 weeks old were injected intraperitoneally with 200 μL of inoculum corresponding to intended number of pfu per dose. Daily weight of mice was measured and serum samples for viremia studies were collected by submandibular bleeding on Days 1 to 4, 6, 8, 10, 12, 15 and 21 post-infection and/or post-challenge.

Quantification of Viral Load by Quantitative PCR (qPCR)

Serum viral RNA was extracted using QIAamp Viral RNA Mini Kit (Qiagen) according to manufacturer's instructions. qPCR was performed using qScript One-Step qRT-PCR kit (Quanta) using ZIKV 1086 and ZIKV 1162c primers and ZIKV 1107-FAM probe. In vitro transcribed RNA containing the target region for primer and probe set was used to generate a standard curve for quantification of serum viral RNA copy number (Table 3).

TABLE 3

Primers used for quantification of viral load

| Primer | Sequence |
|---|---|
| ZIKV 1086 | YCGYTGCCCAACACAAG (SEQ ID NO: 13) |
| ZIKV 1162c | CCACTAAYGTTCTTTTGCAGACAT (SEQ ID NO: 14) |
| ZIKV 1107-FAM | AGCCTACCTTGACAAGCARTCAGACACTCAA (SEQ ID NO: 15) |

Animal Models

C57BL/6 mice were purchased from InVivos (Singapore). The SingHealth Institutional Animal Care and Use Committee approved all mouse experiments. Mice were infected by injecting 100 μL of $1\times10^6$ pfu/mL DENV subcutaneously into the hind footpads. Draining popliteal lymph nodes were collected 24 hours post-infection, snap frozen in O.C.T. Compound (Tissue-Tek), then cryosectioned (10 μm thick sections). Sections were fixed with acetone at 4° C. then stained using J2 anti-dsRNA antibody (English and Scientific Consulting) and FITC-conjugated anti-mouse antibody (Jackson ImmunoResearch). Slides were imaged by confocal microscopy. Images were prepared using ImageJ (National Institutes of Health, USA).

Example 1

Investigation of Factors Contributing to the Limitation of Plaque Sizes.

A major contributing factor to the limitation of plaque sizes is the antiviral response triggered by the innate immune function of host cells used in the assay. It is a cascade of cellular events initiated by infected cells, which releases cellular products such as cytokines that activate antiviral responses in surrounding uninfected cells to prevent infection.

To investigate the antiviral response triggered by the innate immune function of the host cells to each of the viral strains, HuH-7 cells seeded in a confluent monolayer were infected with 10 multiplicity of infection (MOI) of DENV-2 16681 or the DENV-3 strains; or 1MOI and 10MOI of DENV-2 PDK53. At 24 hours post-infection, total cellular RNA was extracted using the RNEasy Mini kit (Qiagen) and then analysed on the Illumina HumanHT-12 v4 Expression Beadchip (Illumina). Results were analysed using Partek Genomics Suite v6.6 ©2014 (Partek). Pathway analysis was done using Gene Set Enrichment Analysis (Broad Institute, USA).

The data in this study showed that DENV-2 PDK53 infection induced a significantly stronger innate immune response in host cells compared to its parental strain DENV-2 16681, while DENV-3 PGMK30 and its parental strain DENV-3 16562 were similarly weakly immunogenic (FIG. 1). Human hepatoma cell line, HuH-7, was infected with the DENV-2 and DENV-3 vaccine and parental strains for 24 h and subsequently subjected to genome-wide microarray screens. At equal amounts of virus inoculum, DENV-2 PDK53 induced stronger up-regulation of innate immune genes, such as inflammatory cytokines and interferons, compared to DENV-2 16681. This difference continued to be observed when DENV-2 PDK53 inoculum was one-tenth of DENV-2 16681 at 1 MOI, thus demonstrating the strong immunogenic property of the former. Conversely, both DENV-3 PGMK30 and DENV-3 16562 displayed weak up-regulation of innate genes compared to DENV-2 PDK53.

Figure 2:
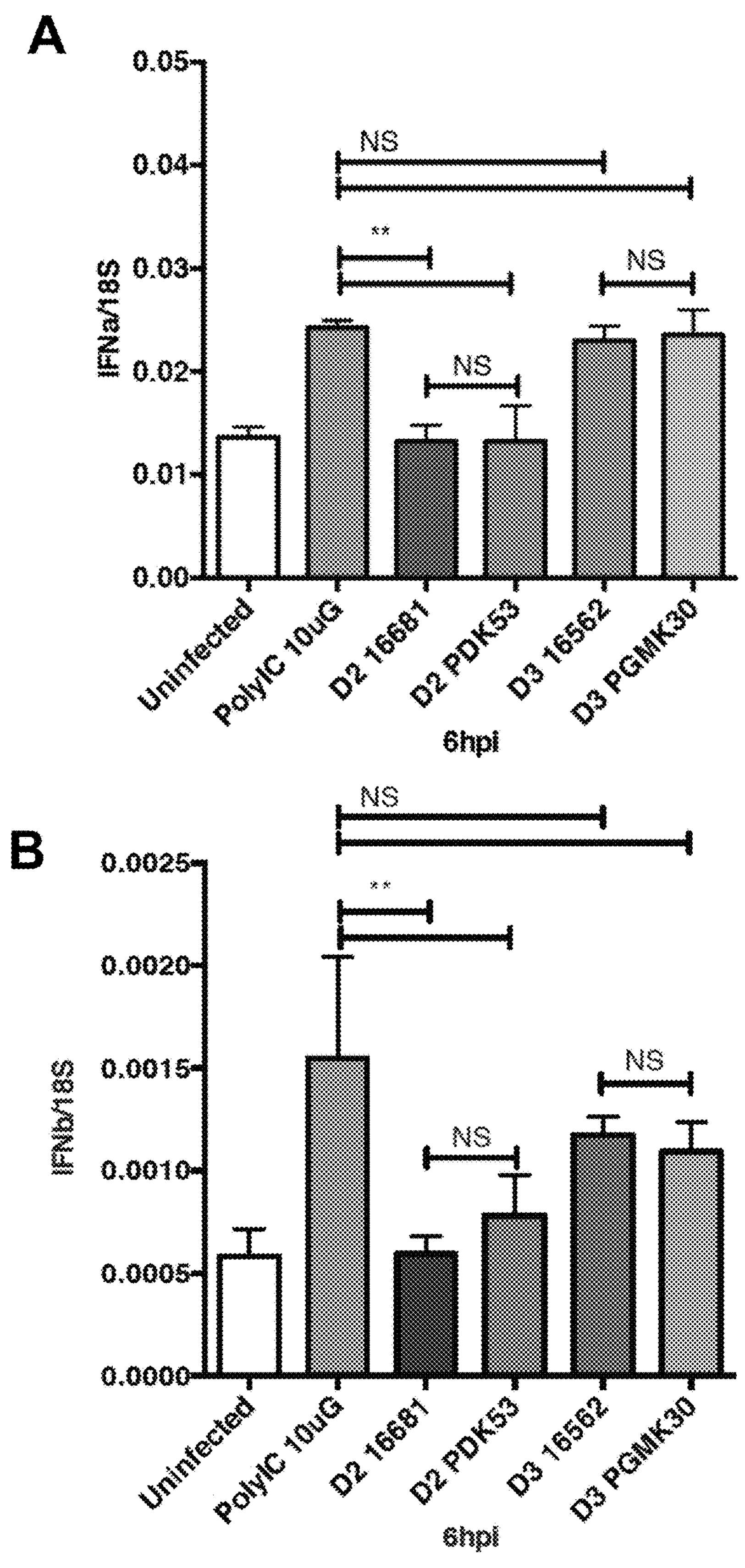
FIG. 2 are bar graphs of gene expression levels of (A) IFNα and (B) IFNβ in Madin Darby Canine Kidney (MDCK) cells and shows that DENV-2 PDK53 but not DENV-3 PGMK30 blocks the antiviral response in each case. MDCK cells were stimulated with Polyinosinic-polycytidylic acid (poly (I:C)) (10 μg/ml) or infected with DENV-2 PDK53, DENV-2 16681, DENV-3 PGMK30 and DENV-3 16562 at 10 or 1 MOI and were evaluated for their expression levels of IFNα and IFNβ using real-time PCR. ** and NS denote p<0.01 and not significant, respectively.

A possible explanation for this difference in the immunogenicity of DENV-2 PDK53 and DENV-3 PGMK30 in HuH-7 cells could be the difference in cell line through which the viruses were generated: primary dog kidney and primary green monkey kidney cells, respectively. As observed in FIG. 2, DENV-2 PDK53 is less immunogenic in MDCK cells compared to DENV-3 PGMK30 and DENV-3 16562, as indicated by the IFNα and IFNβ responses. It was reasoned that the generation of DENV-2 PDK53 from canine cells had conferred on it resistance to canine-specific host innate immune responses. For the same reason, DENV-3 PGMK30 is resistant to primate-specific innate immune responses in HuH-7 cells. Taken together, results here indicate that the successfully attenuated vaccine strain DENV-2 PDK53 had raised its immunogenicity in cells other than those of canine origins during the attenuation process.

Example 2

Investigation of Effective Spreading of Antiviral Responses Due to Superior Immunogenic Properties as a Contributing Factor to the Formation of Smaller Plaques in DENV-2 PDK53.

Next, the possibility that effective spreading of antiviral responses due to superior immunogenic properties could be a contributing factor to the formation of smaller plaques in DENV-2 PDK53 was investigated. This was studied by detecting the migration of phosphorylated STAT1 (pSTAT1), which is a marker of STAT1 activation resulting from interferon activation, in uninfected cells surrounding infected foci.

BHK-21 cells in a confluent monolayer on glass coverslips were infected with 30 plaque-forming units (pfu) of virus and incubated for 72 hours at 37° C. IFNα (Abcam) was used as a positive control. The cells were fixed and permeabilised with 3% paraformaldehyde and 0.1% saponin, then stained with anti-phospho-STAT1 (Y701) rabbit polyclonal IgG (R&D Systems), J2 anti-dsRNA mouse antibody, DAPI, AlexaFluor488 anti-rabbit, and AlexaFluor594 anti-mouse secondary antibodies (Invitrogen). Coverslips were affixed onto glass slides using Mowiol 4-88 (Sigma-Aldrich) and imaged using an LSM 710 confocal microscope (Carl Zeiss).

Figure 3:
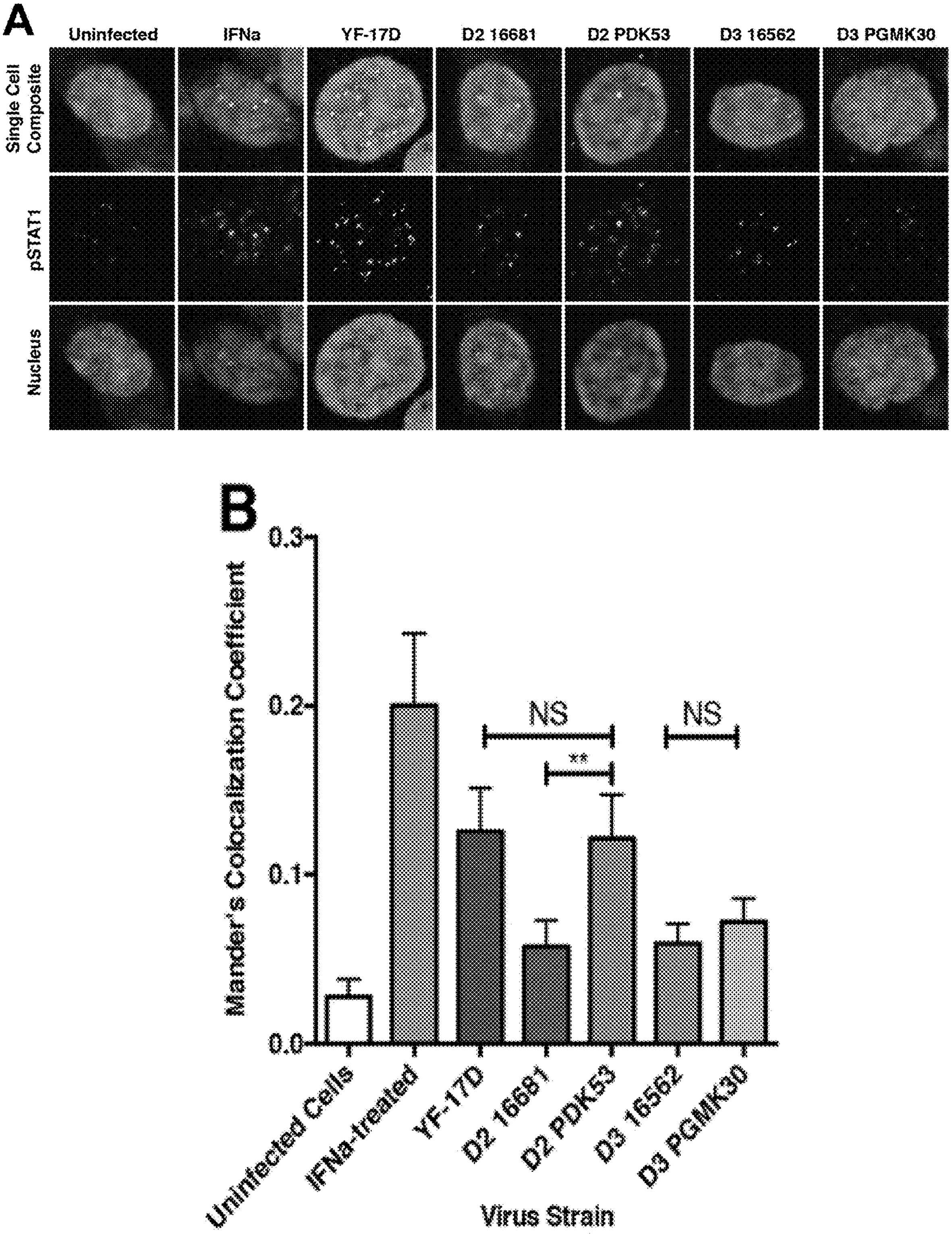
FIG. 3 shows confocal images of cells that were uninfected and untreated (negative control), interferon-treated (positive control), surrounding YF-17D or DENV focus of infection and corresponding Mander's co-localisation coefficient measurements for STAT1 activation in baby hamster kidney BHK-21 cells. A) shows representative confocal microscopy images of cells-Top row shows single cell nucleus composite image of an uninfected cell, near the focus of infection; Second and Third rows show single-channel images of the same cell showing pSTAT1 or cell nucleus, respectively. (B) shows Mander's co-localisation coefficient measurements for nuclear-translocated pSTAT1 measured in uninfected cells in the periphery of viral foci. Levels of nuclear translocated pSTAT1 were similar for PDK53 and YF-17D, both of which were significantly higher compared to 16681, 16562 and PGMK30. P-values were calculated using a two-tailed t-test; ** indicates p<0.01.

As expected, there were greater levels of STAT1 activation in cells surrounding foci of DENV-2 PDK53 infection compared to DENV-2 16681 (FIG. 3), while DENV-3 PGMK30 and DENV-3 16562 remained the same. This increase in STAT1 activation could prepare cells against viral invasion by increasing the expression of interferon-stimulated genes (ISGs), hence limiting the spread of infection and ultimately contain plaque sizes.

Figure 4:
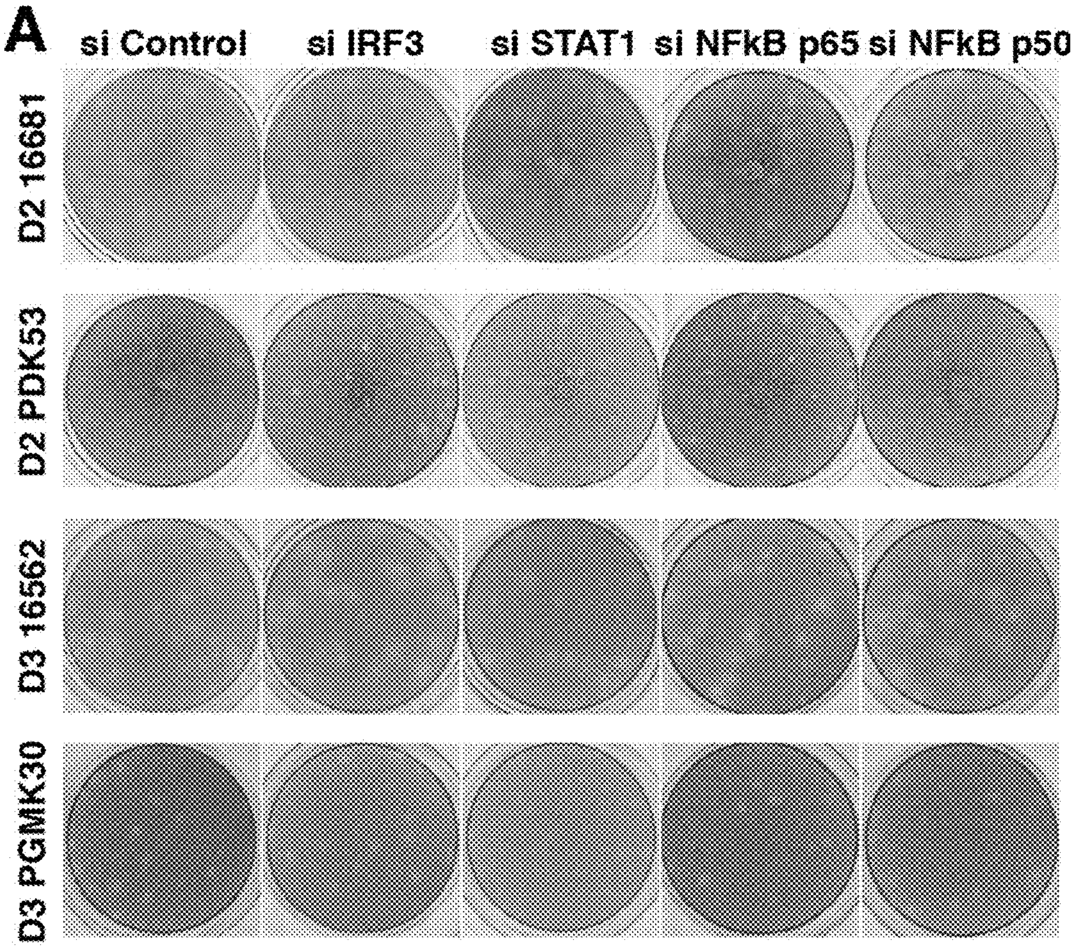
FIG. 4 are the results of plaque assays on cells silenced of major transcription factors for interferon and inflammatory responses and shows that DENV-2 PDK53 infection prevents viral spreading through the induction of innate immune responses. DENV-2 and DENV-3 vaccine and wild-type strains plaque assays at 1 MOI were performed on IRF3-, STAT1-, NF-κB p65- and NF-κB p50-silenced BHK21 cells. (A) Shows photographs of representative plaque assays for each of the viruses and knockdowns. (B) Shows plaque counts (per well of a 24-well plate) for each of the viruses and knockdowns. (C) Shows plaque size distributions of the four virus strains for control and IRF3 knockdown, along with corresponding Bayesian Information Criterion (BIC) scores for unimodal or bimodal distribution. Lower BIC scores indicate better fit for a given type of distribution if the difference is greater than or equal to 10. None of the four control siRNA treatments yielded clear-bimodal plaque size distributions. Of the four IRF3 knockdowns, the best fit for bimodal distribution is shown by PDK53 plaques with IRF3 knockdown, while plaques of the other three viruses better fit a unimodal distribution or were neither clearly unimodal nor bimodal.
Figure 4:
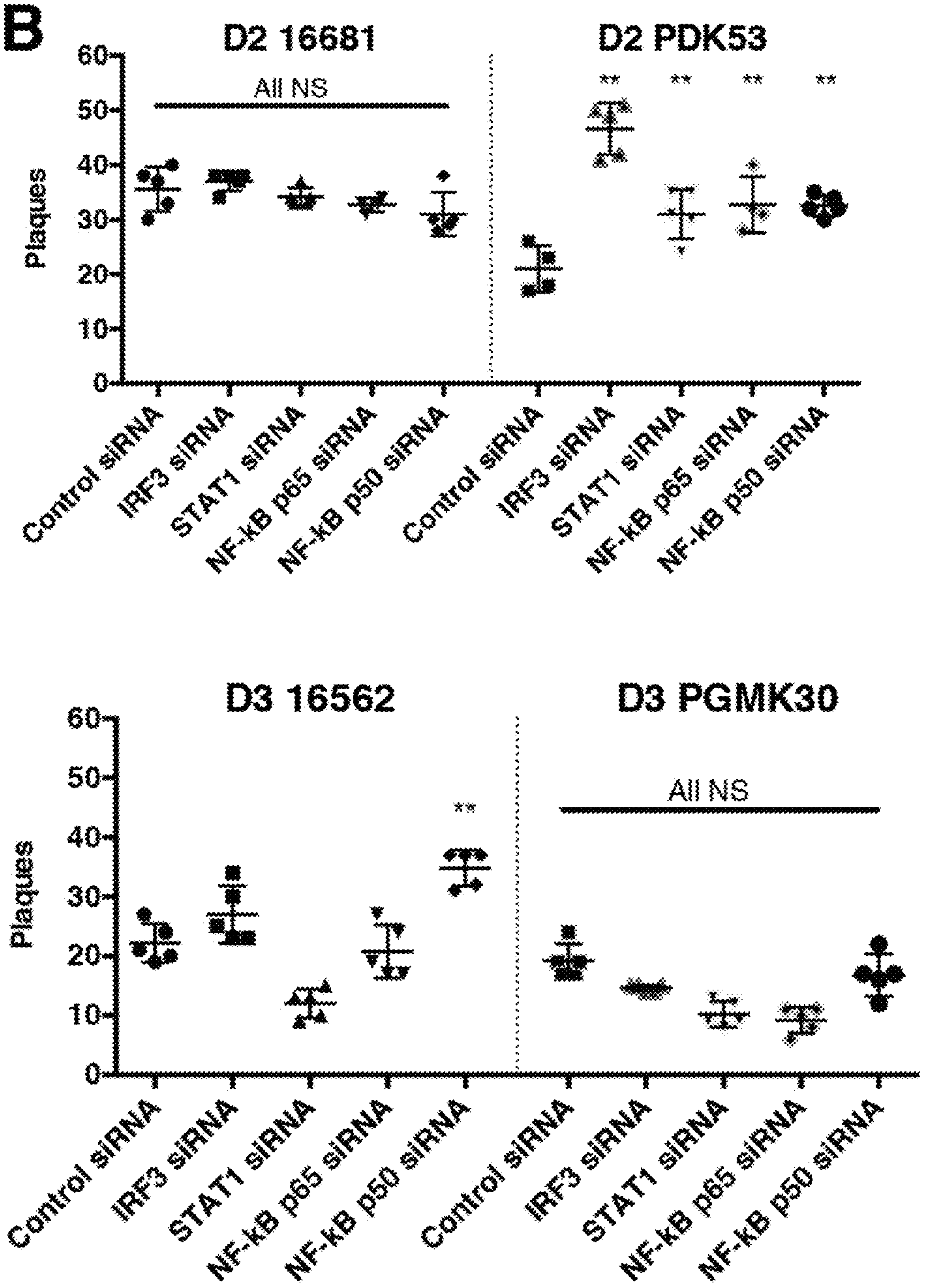
Figure 4:
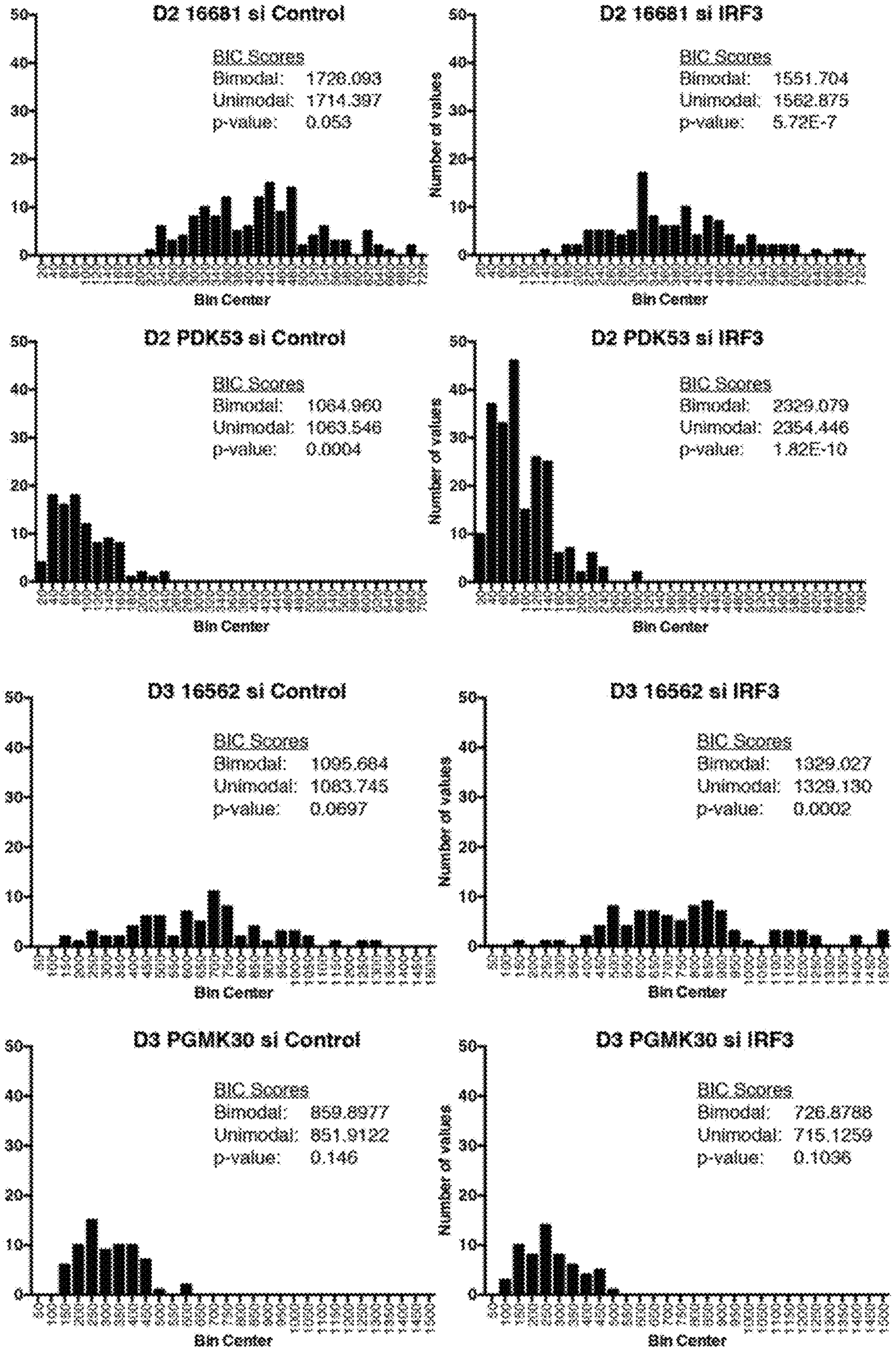

To confirm this observation, plaque assays were performed on BHK-21 cells silenced of major transcription factors for interferon and inflammatory responses; namely: IRF3, STAT1 and NF-kB (p65 and p50) (FIGS. 4A and 4B). To silence the transcription factors, BHK-21 cells seeded in a confluent monolayer were treated with the specified hamster-specific siRNA at 100 nM final concentration complexed with Dharmafect 4 (GE Healthcare) for 48 hours. siRNA sequences used are listed in Table 4. Following siRNA knockdown, each well was infected with 30 pfu of virus, and cultures for plaque assays were incubated for 6 days at 37° C., fixed with 20% formaldehyde and stained with 1% crystal violet (Sigma-Aldrich) to visualize plaques. Cultures for focus forming assay were incubated for 3 days at 37° C., then fixed with 3% paraformaldehyde, permeabilised with 0.1% saponin, then stained with mouse 4G2 monoclonal antibody and anti-mouse horseradish peroxidase antibody. Viral foci were stained with 3-3'-diaminobenzidine (DAB Chromogen) (Dako) and enumerated visually. Resultant plaques were photographed using an EOS 5D digital SLR camera (Canon) at a fixed distance. Plaque sizes were measured in pixels using ImageJ.

TABLE 4

BHK21 siRNA Sequences (*Mesocricetus auratus*)

| Gene Target | siRNA Sequence |
|---|---|
| IRF3 | Sense: GGAACAAUGGGAGUUCGAAdTdT (SEQ ID NO: 16)<br>Antisense: UUCGAACUCCCAUUGUUCCdTdT (SEQ ID NO: 17) |
| STAT1 | Sense: CCGUUUCCAUGACCUCCUUdTdT (SEQ ID NO: 18)<br>Antisense: AAGGAGGUCAUGGAAACGGdTdT (SEQ ID NO: 19) |
| NF-kB p65 | Sense: GCAUCCAGACCAACAAUAAdTdT (SEQ ID NO: 20)<br>Antisense: UUAUUGUUGGUCUGGAUGCdTdT (SEQ ID NO: 21) |
| NF-kB p50 | Sense: CCUCAUGUUCACCGCCUUUdTdT (SEQ ID NO: 22)<br>Antisense: AAAGGCGGUGAACAUGAGGdTdT (SEQ ID NO: 23) |

It was found that DENV-2 PDK53 formed greater number of plaques across all knocked-down (KD) cells, with differences in IRF3 being most significant (FIGS. 4A and 4B). DENV-2 16681, DENV-3 PGMK30 and DENV-3 16562 did not show an increase in plaque numbers for all the KD cells, only D316562 in the presence of NF-κB p50-siRNA showed any significant increase. Importantly, differences in the morphology of plaques induced by DENV-2 PDK53, but not other DENV strains, on IRF3 knockdown cells (FIG. 4C) were also observed. There was an increase in visually smaller atypical plaques such that, when analysis of the plaque size distribution was performed, DENV-2 PDK53 displayed a bimodal curve as opposed to a unimodal curve adopted by DENV-2 16681. This formation of smaller plaques demonstrates that the strong immunogenic property of the successfully attenuated virus does indeed influence plaque formation. In to, results here indicate that the immunogenicity of the virus could be a contributing factor to the formation of small plaques for DENV-2 PDK53, but not DENV-3 PGMK30.

Example 3

Investigation of Virus Infectivity as a Factor that Determines Plaque Size.

With the revelation that plaque formation is strongly influenced by the immunogenicity of the virus, the possibility that infectivity of the virus could be another factor that determines plaque sizes was investigated. The uptake of viruses into cells in vitro was determined by measuring the amounts of specific viral RNA sequences through real-time PCR.

To measure total viral RNA, total cellular RNA was extracted using the RNEasy Mini kit (Qiagen), and complementary DNA synthesized using the iScript cDNA Synthesis kit (Bio-Rad). To measure total viral RNA, quantitative real-time PCR was done using a primer pair targeting a highly conserved region of the 3' UTR common to all four serotypes of dengue; inter-sample normalization was done using GAPDH as a control. Primer sequences are listed in Table 5. Pronase (Roche) was used at a concentration of 1 mg/mL and incubated with infected cells for five minutes on ice, before washing with ice cold PBS. Total cellular RNA was then extracted from the cell pellets in the manner described above.

TABLE 5

PCR primer sequences.

| Gene Target | Primer Sequence |
|---|---|
| DENV LYL 3'UTR | Forward: TTGAGTAAACYRTGCTGCCTGTA TGCC (SEQ ID NO: 24) Reverse: GAGACAGCAGGATCTCTGGTCTY TC (SEQ ID NO: 25) |
| GAPDH (Human) | Forward: GAGTCAACGGATTTGGTCGT (SEQ ID NO: 26) Reverse: TTGATTTTGGAGGGATCTCG (SEQ ID NO: 27) |
| CXCL10 (Human) | Forward: GGTGAGAAGAGATGTCTGAATCC (SEQ ID NO: 28) Reverse: GTCCATCCTTGGAAGCACTGCA (SEQ ID NO: 29) |
| ISG20 (Human) | Forward: ACACGTCCACTGACAGGCTGTT (SEQ ID NO: 30) Reverse: ATCTTCCACCGAGCTGTGTCCA (SEQ ID NO: 31) |
| IFIT2 (Human) | Forward: GAAGAGGAAGATTTCTGAAG (SEQ ID NO: 32) Reverse: CATTTTAGTTGCCGTAGG (SEQ ID NO: 33) |
| IFNα (Canine) | Forward: GCTCTTGTGACCACTACACCA (SEQ ID NO: 34) Reverse: AAGACCTTCTGGGTCATCACG (SEQ ID NO: 35) |
| IFNβ (Canine) | Forward: GGATGGAATGAGACCACTGTCG (SEQ ID NO: 36) Reverse: ACGTCCTCCAGGATTATCTCCA (SEQ ID NO: 37) |

The proportion of infected cells was assessed by flow cytometry. Cells were fixed and permeabilised with 3% paraformaldehyde and 0.1% saponin, respectively. DENV envelope (E) protein was stained with mouse monoclonal 4G2 antibody (ATCC) and AlexaFluor488 anti-mouse secondary antibody. Flow cytometry analysis was done on a BD FACS Canto II (BD Bioscience).

Figure 5:
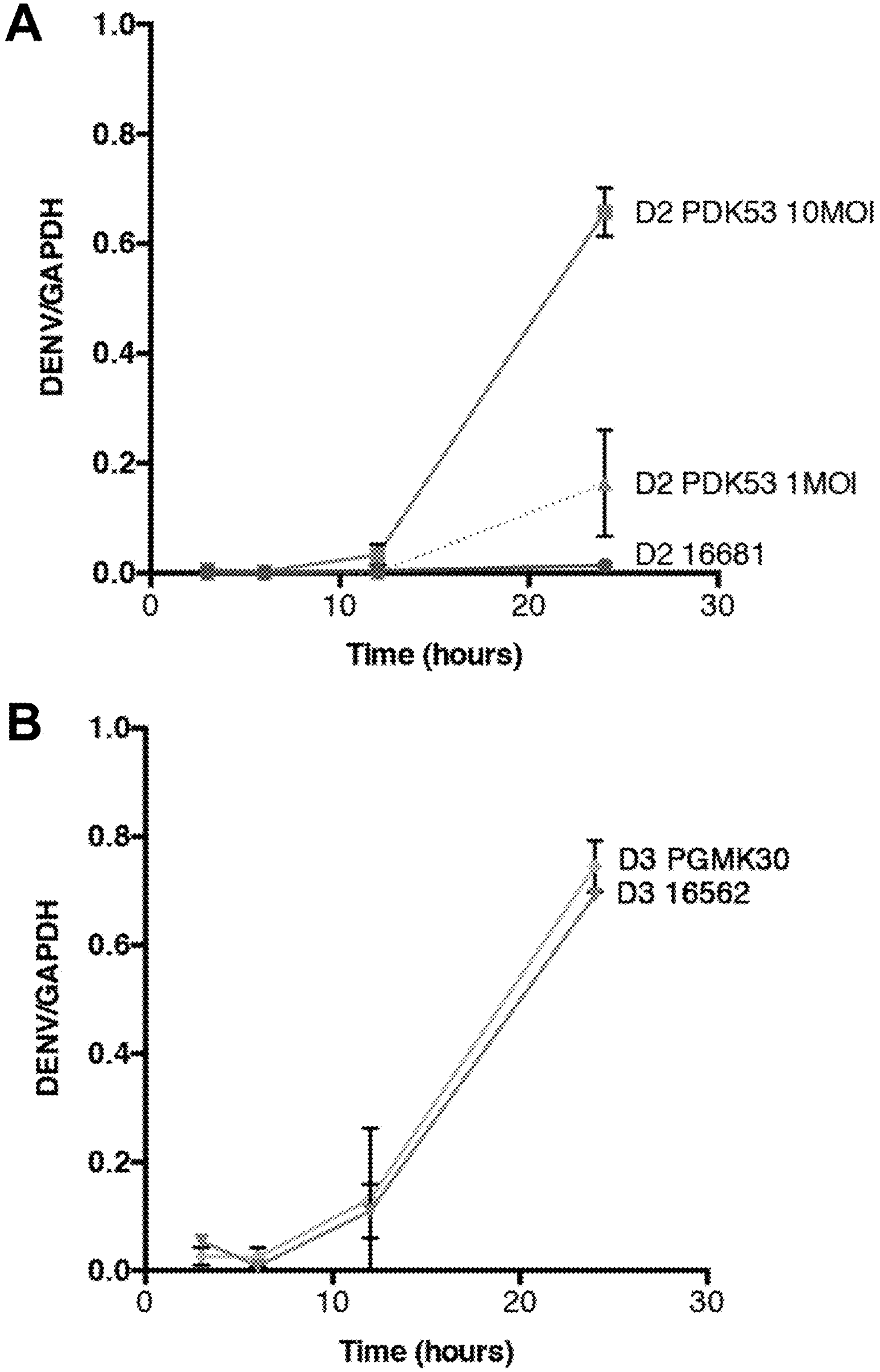
FIG. 5 are line graphs of the rate of viral uptake in Human hepatoma-7 (HuH-7) cells infected with various strains of dengue virus. (A) shows that DENV-2 PDK53 infection in HuH-7 cells has a higher rate of viral uptake compared to DENV-2 16681, while (B) shows no difference in viral uptake between DENV-3 16562 and DENV-3 PGMK30. All viruses were infected at 10 MOI, and DENV-2 PDK53 was infected at 10 MOI and at 10× dilution (1 MOI). Rate of viral replication at 10 or 1 MOI over 24 hours was determined by real-time PCR detection of DENV-specific cross-serotype sequences.
Figure 6:
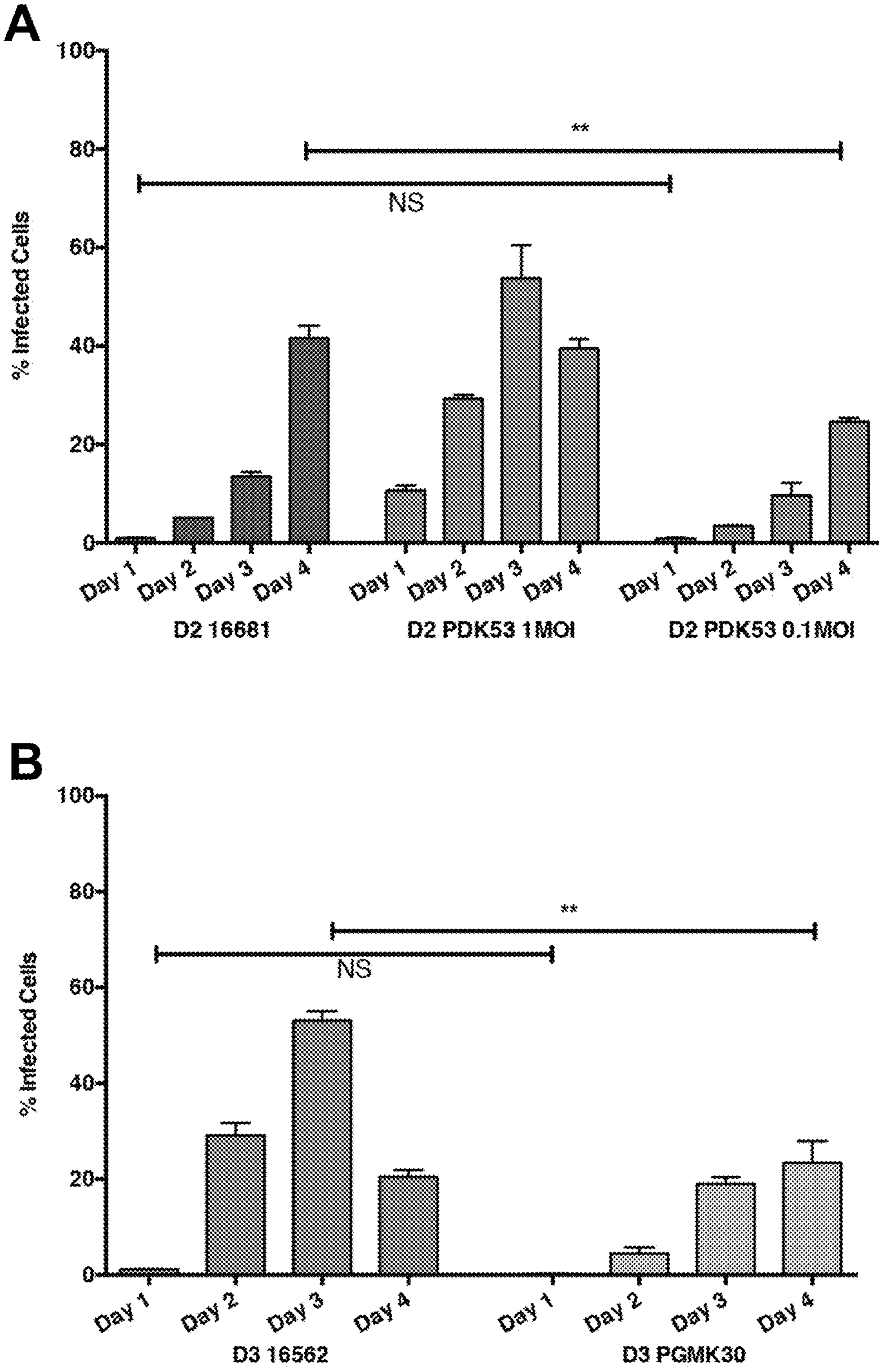
FIG. 6 are bar graphs of viral replication rate in HuH-7 cells infected with various dengue virus strains and shows that DENV-2 PDK53 infection in HuH-7 cells has a higher viral spreading compared to DENV-2 16681, DENV-3 16562 and DENV-3 PGMK30. A, B, HuH-7 cells were infected with (A) DENV-2 and (B) DENV-3 vaccine and wild-type strains, at 1 or 0.1 MOI as indicated, for 24 hours. Significant differences in percentage-infected cells were found between day 4 with DENV-2 16681 and DENV2-PDK53 and day 3 with DENV-3 16562 and DENV3 PGMK30. Viral spreading, as implied by the percentage of infection, was measured by detecting DENV E protein using flow cytometry. ** and NS denote p<0.01 and not significant, respectively.

Unexpectedly, despite DENV-2 PDK53 inducing stronger antiviral immune responses, it had higher rates of uptake by HuH-7 cells compared to DENV-2 16681 (FIG. 5). This difference continued to be observed when DENV-2 PDK53 inoculum was reduced 10-fold. In contrast, DENV-3 PGMK30 and its parental strain DENV-3 16562 displayed the same rate of viral uptake in host cells. Furthermore, DENV-2 PDK53 showed a higher viral replication rate compared to DENV-2 16681. This was determined by measuring the percentage of cells that harbored DENV E-protein, detected using flow cytometry. DENV-2 PDK53 showed a higher percentage of infected cells compared to DENV-2 16681 at the same amount of MOI from Day 1 to 3 (FIG. 6). In contrast, DENV-3 PGMK30 showed a reverse trend and displayed lower percentage of infected cells compared to DENV-3 16562. Results here show that successfully attenuated vaccines, as exemplified by DENV-2 PDK53, have greater uptake and replication rate.

Results above demonstrate that the DENV-2 PDK53 and DENV-3 PGMK30 are polarized in their properties that influence plaque morphologies. While both attenuated strains were selected for their formation of smaller plaques compared to their parental strains, the factors leading to this outcome are different between the two.

Accordingly, this study has demonstrated that successfully attenuated vaccines, as exemplified by DENV-2 PDK53 in this study, form smaller plaques due to induction of strong innate immune responses, which is triggered by fast viral uptake and spread of infection. In contrast, DENV-3 PGMK30 form smaller plaques due to its slower uptake and growth in host cells, which inadvertently causes lower up-regulation of the innate immune response.

Based on the results presented in the foregoing Examples, the present invention provides a new strategy to prepare a LAV, which expedites the production process and ensures the generation of effectively attenuated viruses fit for vaccine use.

Example 4

Strategy for Attenuating Viruses for Vaccine Applications

A description of the procedure and the amount of time required for each step is detailed in Table 6 below.

Table 6. Description of procedures and the estimated time required to achieve each of the steps in the proposed method of manufacturing attenuated vaccines.

| Steps | | Estimated shortest time required |
|---|---|---|
| 1. | Passaging of virus from clinical isolates in cultured cells distinct from intended host for no more than 5 passages, random mutagenesis, mutagenesis with a chemically-derived mutagen, culture at temperature lower than 37° C., or a combination thereof | 2 weeks |
| 2. | Infecting intended host cells, selecting a host cell displaying a preselected phenotype, isolating viral nucleic acid from the selected host cell | 1 week |
| 3. | Sequencing of virus from single/pooled selected cells | 2 weeks |
| 4. | Reconstruction of candidate live attenuated vaccines in infectious clones | 2-3 weeks |
| 5. | Production of candidate live attenuated vaccines | 1 week |
| 6. | In-vitro and/or in-vivo screening of candidate live attenuated vaccines for desired phenotypes | 2 weeks |

General Description of Steps in Table 6

The objective of step 1 is to generate a virus population with a diverse genetic makeup from clinical isolates. A cell or cell line from a species other than the intended vaccine is infected so that there is no adaptation of the virus to the innate immunity of the intended host. Mutagenesis of the virus may occur through serial passaging of the infected cell no more than 5 times, culture of the infected cell under sub-optimal conditions (e.g. at a temperature lower than 37° C.) or by random mutagenesis (e.g. error-prone PCR or using a mutagen). A chemically derived mutagen such as Ribavirin and 5-fluorouracil may be added to further enhance the mutagenesis of the virus. Alternatively, a chemically derived mutagen is used on its own to generate the population of genetically diverse virus. Generating a diverse population of viruses increases the chances of generating strains that fit the desired selection criteria (i.e.: fast growing and with strong immunogenic properties). After a short period of infection (e.g.: 24 hours), the virus is isolated and used in step 2.

The objective of step 2 is to select for specific viruses that induce a specific phenotype that may be indicative of viral infectivity and/or immunogenicity. A specific phenotype may be small plaque size relative to the original virus or the wild-type virus, or high ISRE responses, which is an indication of their propensity to activate type-I-interferon responses. Where the specific phenotype is plaque size, this is performed by infecting cells of the same species as the target vaccine with the viruses derived from step 1, collecting the supernatant and using the supernatant in a plaque assay. Plaques of interest are then selected and purified. Where the specific phenotype is the induction of ISRE response, this is performed by infecting cells of the same species as the target vaccinee that carry the ISRE-driven GFP reporter gene with the viruses derived from step 1. GFP expression in these cells indicates the activation of ISRE. Cells expressing high level of GFP fluorescence, which is indicative of high ISRE activation, are isolated through cell sorting by flow cytometry. Viruses extracted from these cells are therefore the specific ones that induce high ISRE responses and are assumed to exhibit the characteristics of fast viral entry and strong immunogenicity, which are the traits of successfully attenuated viruses.

The objective of step 3 is to characterize the virus that has been isolated from step 2, so that its genetic identity is known and a blueprint can therefore be created to make replicas of it. To characterize the virus, sequencing of its genetic make-up, through the use of various techniques such as Sanger sequencing or Next-Generation sequencing, is performed in conjunction with the use of other bioinformatics tools to assemble the whole viral genome.

The objective of step 4 is to reconstruct the identified virus after its genetic blue print from step 3 is obtained. To do this, mutagenesis of infectious clones that were generated from the initial input of clinical virus isolate is performed.

The objective of step 5 is the production of the reconstructed virus from step 4. Briefly, the infectious clone plasmids are linearized and in vitro transcribed to produce viral RNA, which is then introduced into host cells through electroporation or transfection. Replicas of these viruses are replicated and released from the host cells, which is harvested from the cell culture media. Alternatively, the infectious clone plasmids may contain a constitutive promoter that drives transcription of viral RNA. These infectious clone plasmids may be introduced into host cells through electroporation or transfection and the viral genome is transcribed to produce viral RNA, which serves as a template for viral protein synthesis and viral replication.

The objective of step 6 is to screen and assess if the resulting virus from step 5 is a fit candidate for live attenuated vaccine production. The virus may be assessed in vitro to determine if it possesses one or more of the desirable phenotypes displayed by successfully attenuated LAVs: rapid replication in host cells; ability to trigger robust host innate immune responses; and the generation of small plaques in plaque assays. With the completion of in vitro assessment of the LAV, in vivo assessment of protective efficacy on animal models, such as mice and macaques, may follow. Alternatively, the in vitro and in vivo screening steps may be performed independently or simultaneously.

Example 5

Generation of a Zika Virus LAV

Figure 8:
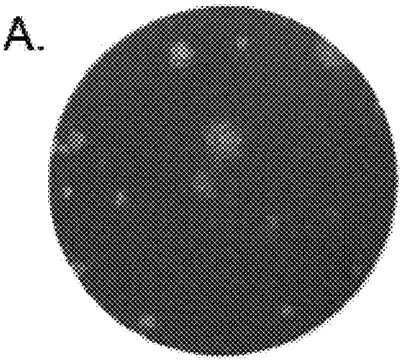
FIG. 8 shows plaque assays for PF13/251013-18 and identified mutants. (A) shows that laboratory stock of PF13/251013-18 produces plaques of varied sizes on plaque assay. (B) shows sequencing results of plaque-purified variants and demonstrates that the consensus sequence changes in the laboratory stock were also identified in the small-plaque variants. (C) shows the plaque phenotypes of infectious clone-derived viruses that were constructed based on sequences of small-plaque variants and their corresponding sequence changes. DN-1, DN-2 and DN-4 display small-plaque phenotypes on plaque assay.
Figure 8:
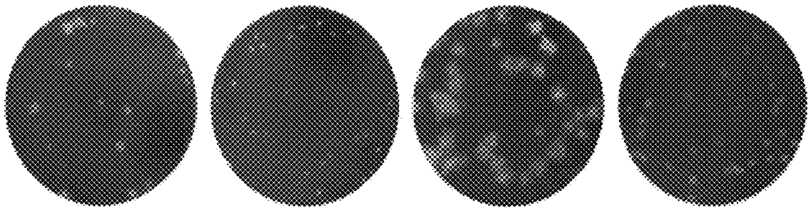

A French Polynesian strain of Zika virus (ZIKV), PF13/251013-18 (SEQ ID NO: 38), was passaged in Vero and C6/36. Following 4 rounds of passage in Vero and a single round passage in C6/36, next-generation sequencing (NGS) of PF13/251013-18 revealed 2 amino acid sequence changes as compared to its reference genome (GenBank ID KX369547). Furthermore, plaque assay of PF13/251013-18 also identified virus plaques of different sizes (FIG. 8A). Of interest, virus variants producing small plaques, which could serve as potential live attenuated vaccine (LAV) candidates were then plaque-purified, sequenced and confirmed to contain the 2 nucleic acid sequence changes that give rise to amino acid changes in the laboratory stocks of PF13/251013-18 (FIG. 8B). Infectious clones of PF13/251013-18 containing these mutations (hereafter referred to as DN-1) (SEQ ID NO: 39) and other mutations identified in the plaque-purified small plaque variants, DN-2 (SEQ ID NO: 40), DN-3 (SEQ ID NO: 41) and DN-4 (SEQ ID NO: 42) were generated using Gibson assembly. DN-1, DN-2 and DN-4 recovered from the infectious clones display small-plaque phenotypes on plaque assay (FIG. 8C).

Figure 9:
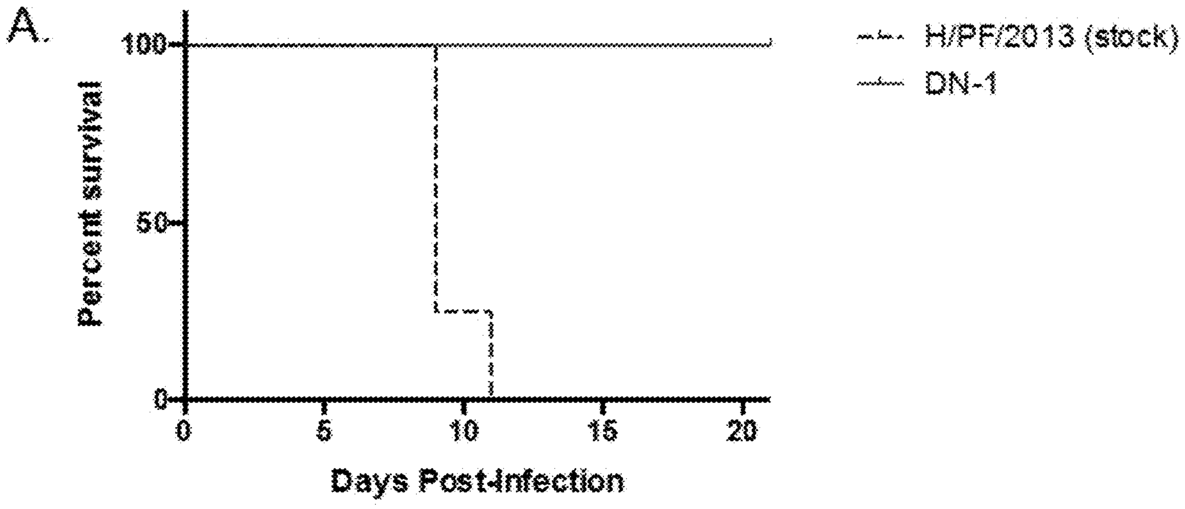
FIG. 9 shows in vivo safety results of the candidate LAV. Male A129 mice were injected intraperitoneally with $10^3$ pfu of DN-1 or H/PF/2013 (4 mice per group). (A) shows that whilst H/PF/2013 was lethal to A129 mice, all mice injected with DN-1 survived. (B) shows that this corresponds with about 2 logs lower viremia levels when infected with DN-1 as compared to the lethal H/PF/2013 strain. (C) shows that there was no significant weight change as compared to those that received PBS as mock immunization. At 21 days post-infection, mice that received immunization with DN-1 and PBS were challenged with 104 pfu of H/PF/2013. (D) shows that animals that received DN-1 were fully protected whilst those that received PBS showed 60% mortality. DN-1 immunization also prevented (E) weight loss in recipient animals and (F) provided sterilizing immunity against the challenge infection whereby there was undetectable viremia.
Figure 9:
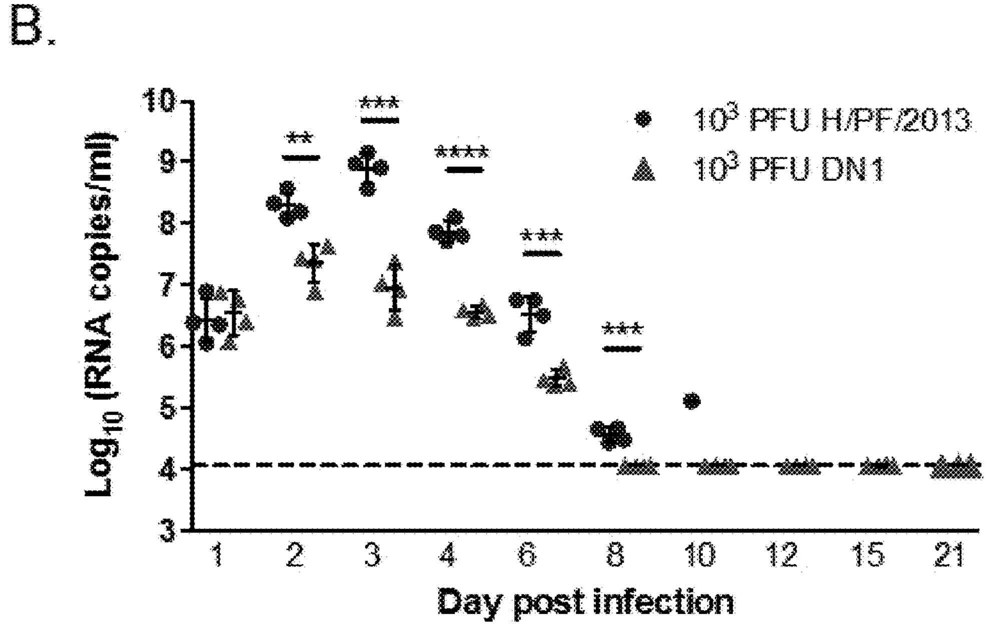
Figure 9:
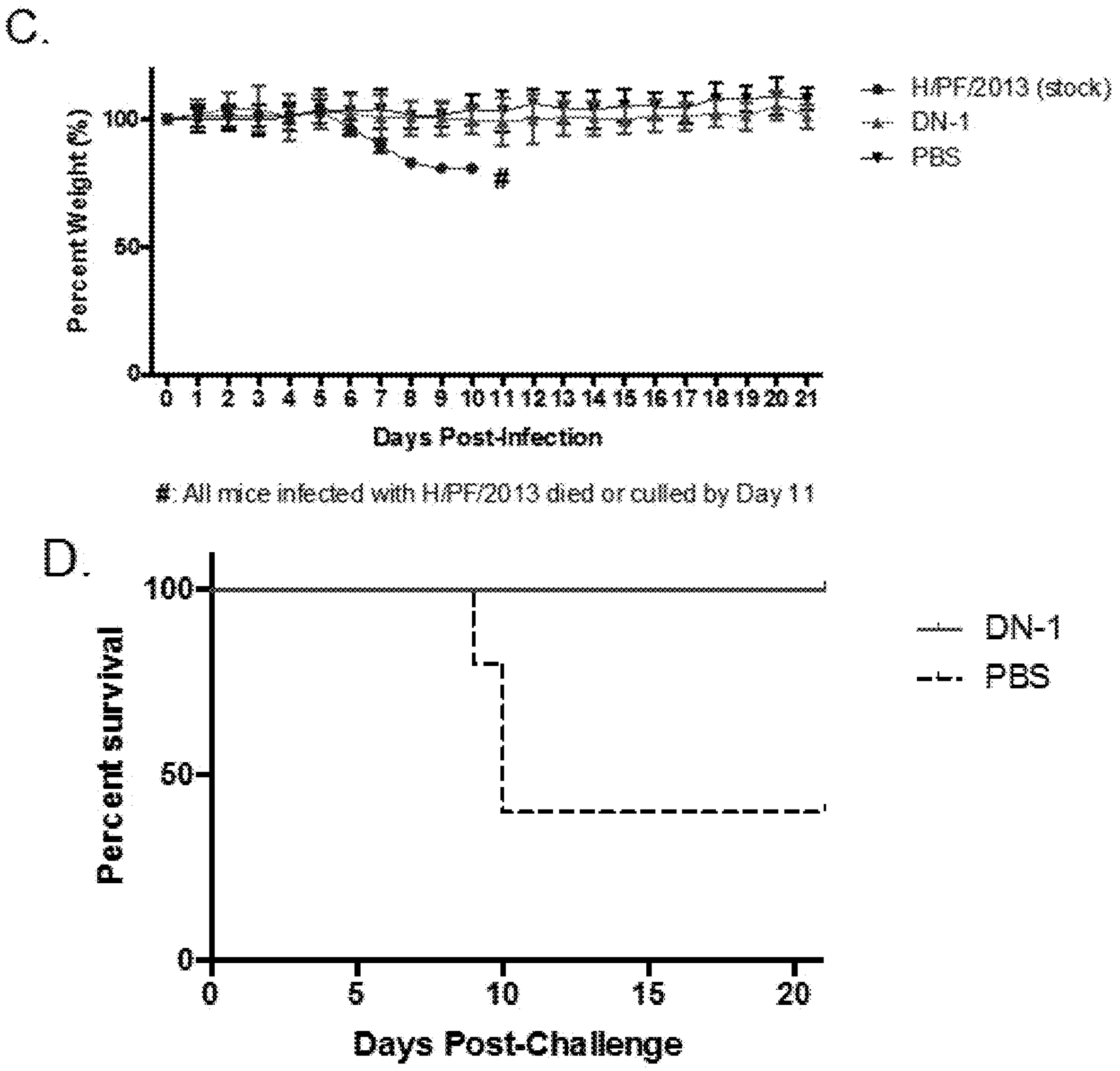
Figure 9:
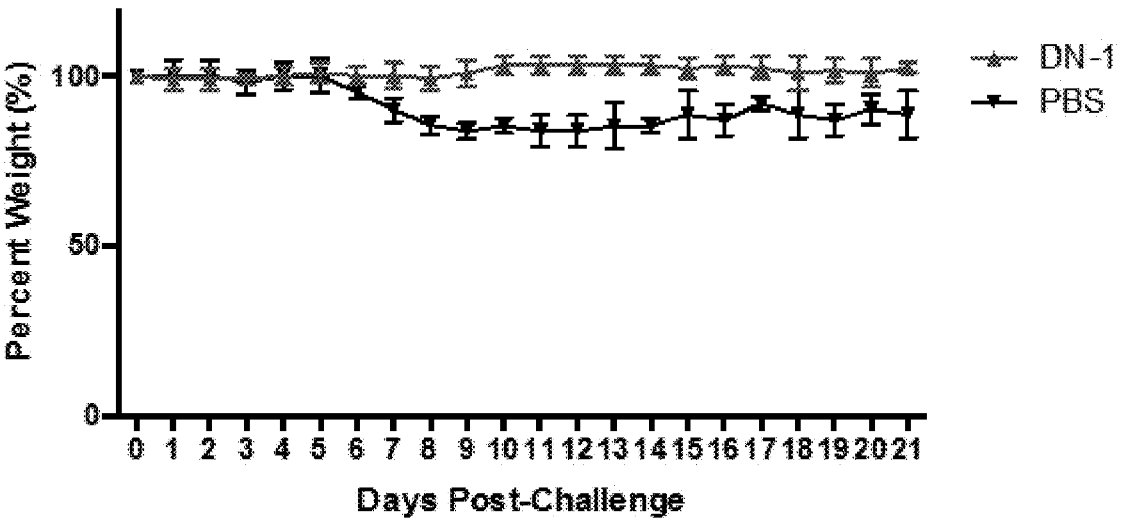
Figure 9:
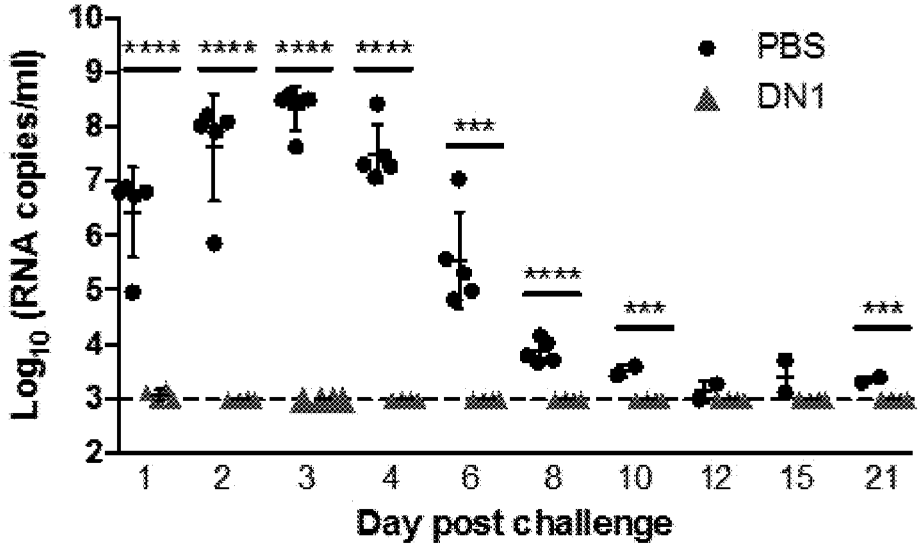

DN-1 was tested in a Type I interferon receptor-deficient mouse model, A129. $10^3$ plaque-forming units (pfu) of DN-1 were injected through the intraperitoneal route into male A129 mice. As compared to another French Polynesian ZIKV strain, H/PF/2013, which was lethal in the A129 mouse model, mice that received DN-1 showed 100% survival rate in contrast to H/PF/2013 where the survival rate was 0% (FIG. 9A). The viremia of DN-1 was almost 2 logs lower than that of H/PF/2013 on day 3 post infection (FIG. 9B). There was also no significant weight loss compared to mice injected with PBS (FIG. 9C). The utility of DN-1 as a LAV candidate was next tested by challenging mice injected with DN-1 at 21 days post-immunization with 104 pfu of H/PF/2013. DN-1 provided complete protection against the challenge virus while animals that received phosphate-buffered saline (PBS) mock immunization showed 60% mortality rate (FIG. 9D). Mice immunized with DN-1 not only showed no weight loss but also had undetectable viremia levels (FIG. 9E, 9F). These in vivo data demonstrate that DN-1 is an attractive LAV candidate that is able to elicit sterilizing immunity against a lethal dose of ZIKV in the A129 model, suggesting potential efficacy as a LAV for clinical development.

Example 6

Generation of a Dengue Virus LAV

Figure 7:
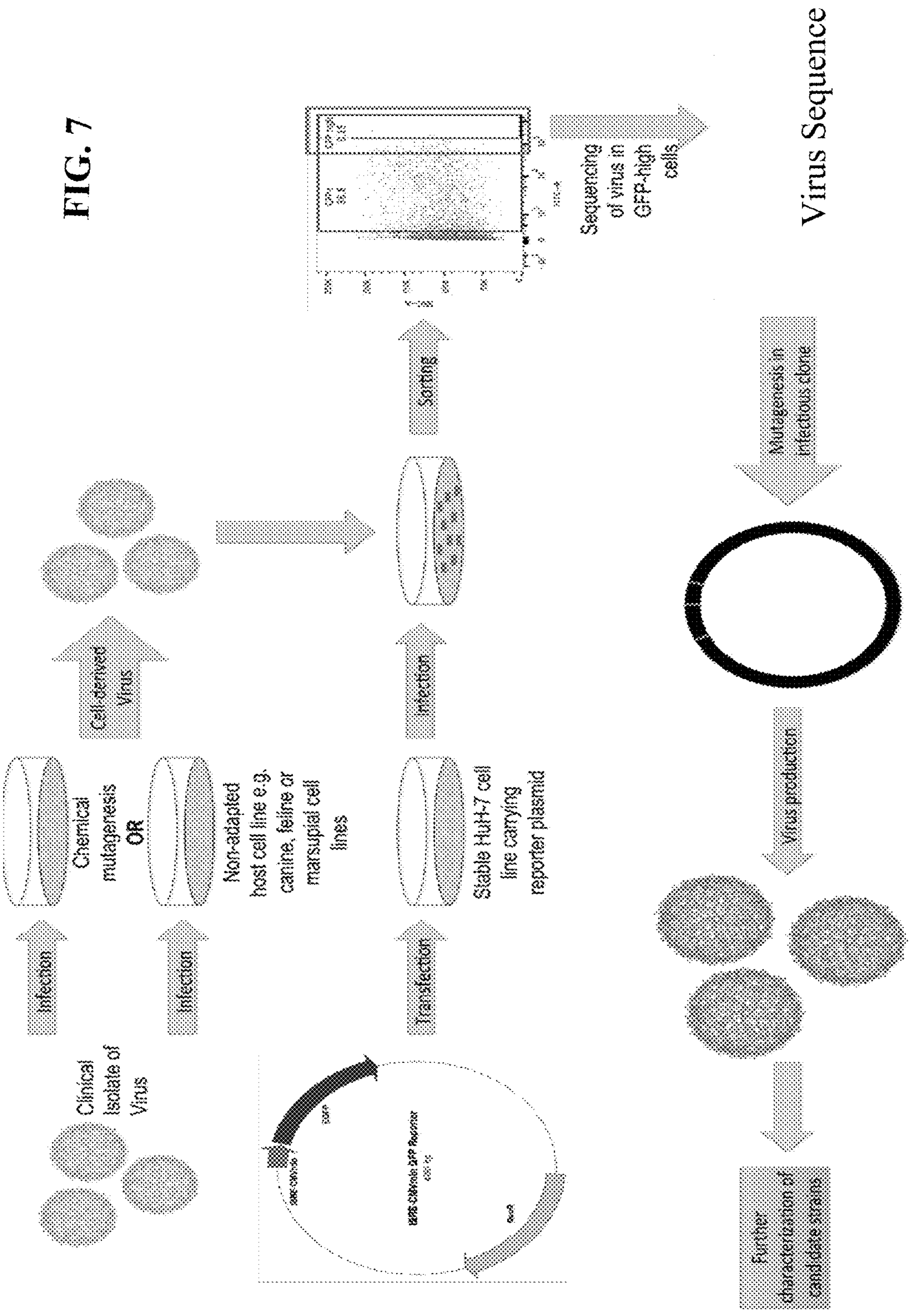
FIG. 7 shows a schematic describing the workflow in the generation of a live attenuated vaccine in the proposed method.

One strain each of DENV-2 (DV2-3295, GenBank ID: EU081177) and DENV-4 (DV4-2270, GenBank ID: GQ398256) were put through the workflow highlighted in FIG. 7. Briefly, $3\times10^6$ cells per T25 flask were infected at MOI 10 with either DV2-3295 or DV4-2270. DV2-3295-infected cells were mutagenized for 4 hours with 600 μM 5-fluorouracil (5-FU) before changing to maintenance media and virus supernatant was harvested at day 3. DV4-2270-infected cells were mutagenized with 600 μM 5-FU for 3 days. The virus supernatants were used to infect IFNβ-promoter-driven GFP reporter HuH-7 cells seeded in 6-well plates. After 48 hours, the infected cells were trypsinized off the plates for FACS sorting on BD FACSAria™ (BD Biosciences) for GFP-positive cells. RNA was extracted from GFP-positive cells using RNeasy Micro Kit (QIA- GEN). cDNA was synthesized using SuperScript III First-Strand Synthesis Kit (Invitrogen).

Figure 10:
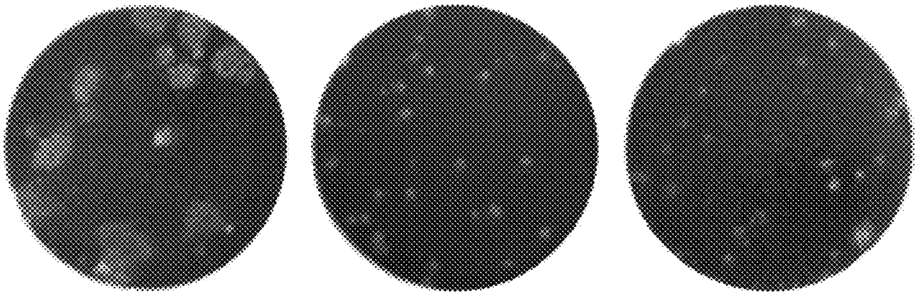
FIG. 10 shows mutations identified for DV2-3295 and DV4-2270 after following proposed workflow. (A) shows the mutations identified from DV2-3295. Plaque assay with viruses recovered from infectious clones for DV2-3295, D2-A and D2-B demonstrated that D2-A and D2-B produce small plaques as compared to DV2-3295. (B) shows that four mutations were identified from DV4-2270.

Sanger sequencing was then performed to identify mutations present in sorted cells and the mutations are shown in FIG. 10. Using the 2 mutations identified for DV2-3295, infectious clones for D2-A (SEQ ID NO: 57) and D2-B (SEQ ID NO: 58) were constructed using Gibson assembly and the primers in Table 7. Viruses were recovered as per the ZIKV mutants. Plaque assay demonstrated that they produce small plaques (FIG. 10A).

Four mutations were identified from the sorted GFP-positive cells infected with mutagenized DV4-2270 infection (FIG. 10B).

TABLE 7

Gibson Assembly Primers for DENV2

| Primer Name | Sequence |
|---|---|
| Fragment 1 (2212 bp) | |
| D2-F1 | AGAGCTCGTTTAGTGAACCGAGTTGTTAGTCTACGTGGACCGAC (SEQ ID NO: 43) |
| D2-R1 | GCTGTGTCACCTAAAATGGCCATTCTCTTC (SEQ ID NO: 44) |
| Fragment 2 (1370 bp) | |
| D2-F2 | GAAGAGAATGGCCATTTTAGGTGACACAGC (SEQ ID NO: 45) |
| D2-R2 | GGAACAATGCCATTCCCAAGACTCCTAGTG (SEQ ID NO: 46) |
| Fragment 3 (1432 bp) | |
| D2-F3 | CACTAGGAGTCTTGGGAATGGCATTGTTCC (SEQ ID NO: 47) |
| D2-R3 | GGAGATCCTGACGTTCCAGGAGAAAAGTCC (SEQ ID NO: 48) |

TABLE 7-continued

Gibson Assembly Primers for DENV2

| Primer Name | Sequence |
|---|---|
| Fragment 4 (2098 bp) | |
| D2-F4 | GGACTTTTCTCCTGGAACGTCAGGATCTCC (SEQ ID NO: 49) |
| D2-R4 | GGAATTTTCAATGCTATGTCTCAACATTGGTG (SEQ ID NO: 50) |
| Fragment 5 (1632 bp) | |
| D2-F5 | CACCAATGTTGAGACATAGCATTGAAAATTCC (SEQ ID NO: 51) |
| D2-R5 | CTGTCATTGCCATCTGTGTCACCATGGG (SEQ ID NO: 52) |
| Fragment 6 (2165 bp) | |
| D2-F6 | CCCATGGTGACACAGATGGCAATGACAG (SEQ ID NO: 53) |
| D2-R6 | GATGCCATGCCGACCCAGAACCTGTTGATTCAACAGCACC (SEQ ID NO: 54) |
| Vector Amplification | |
| D2-F7 | GGTGCTGTTGAATCAACAGGTTCTGGGTCGGCATGGCATCTCCAC (SEQ ID NO: 55) |
| D2-R7 | GTCGGTCCACGTAGACTAACAACTCGGTTCACTAAACGAGCTCT (SEQ ID NO: 56) |

The present invention is based on novel procedures that identify and select for a virus that exhibits susceptibility to a host defense mechanism in order to generate a live attenuated vaccine. Advantageously, mutations of the coding regions of the virus that confer virulence in order to weaken or attenuate the virus are not necessary.

The invention claimed is:

1. A vaccine comprising a nucleic acid sequence encoding the genome of a maladapted Zika virus, wherein the nucleic acid sequence comprises a sequence selected from the group consisting of SEQ NO: 39, SEQ ID NO: 40, SEQ ID NO: 41, and SEQ ID NO: 42.

2. The vaccine of claim 1, wherein the nucleic acid sequence is a DNA sequence or a messenger RNA (mRNA) sequence.

3. The vaccine of claim 1, wherein the nucleic acid sequence is SEQ ID NO: 40.

4. The vaccine of claim 1, wherein the maladapted Zika virus is generated by passaging a Zika virus at least once in a cell or cell line that is of a species distinct from the intended recipient of the vaccine.

5. The vaccine of claim 1, wherein the maladapted Zika virus is generated by passaging a Zika virus for four rounds in Vero cells, followed by passaging for a single round in C6/36 cells.

6. The vaccine of claim 5, wherein the Zika virus is a French Polynesian strain of Zika virus.

7. The vaccine of claim 6, wherein the Zika virus strain is PF13/251013-18.

8. The vaccine of claim 1, wherein the vaccine is capable of eliciting sterilizing immunity in a subject.

9. The vaccine of claim 1, wherein the vaccine is a live attenuated vaccine.

10. A method of preventing or treating a Zika infection in a subject comprising administering to the subject an effective amount of the vaccine of claim 1.

11. The method of claim 10, wherein the administering comprises intradermal, intramuscular or subcutaneous injection.

12. The method of claim 10, wherein the vaccine is administered alone or in combination with a buffer.

13. The method of claim 10, wherein the vaccine is administered to the subject in a single dose or in multiple doses.

14. A method of inducing sterilizing immunity to a Zika infection in a subject comprising administering to the subject an effective amount of the vaccine of claim 1.

15. The method of claim 14, wherein the administering comprises intradermal, intramuscular or subcutaneous injection.

16. The method of claim 14, wherein the vaccine is administered alone or in combination with a buffer.

17. The method of claim 14, wherein the vaccine is administered to the subject in a single dose or in multiple doses.

* * * * *